United States Patent
Yasuda et al.

(10) Patent No.: US 9,733,564 B2
(45) Date of Patent: Aug. 15, 2017

(54) COPOLYMERS FOR LITHOGRAPHY AND METHOD FOR PRODUCING SAME, RESIST COMPOSITION, METHOD FOR PRODUCING SUBSTRATE WITH PATTERN FORMED THEREUPON, METHOD FOR EVALUATING COPOLYMERS, AND METHOD FOR ANALYZING COPOLYMER COMPOSITIONS

(75) Inventors: Atsushi Yasuda, Yokohama (JP);
Tomoya Oshikiri, Yokohama (JP);
Hikaru Momose, Otake (JP)

(73) Assignee: Mitsubishi Chemical Corporation, Tokyo (JP)

( * ) Notice: Subject to any disclaimer, the term of this patent is extended or adjusted under 35 U.S.C. 154(b) by 39 days.

(21) Appl. No.: 13/879,737

(22) PCT Filed: Oct. 14, 2011

(86) PCT No.: PCT/JP2011/073623
§ 371 (c)(1),
(2), (4) Date: Apr. 16, 2013

(87) PCT Pub. No.: WO2012/053434
PCT Pub. Date: Apr. 26, 2012

(65) Prior Publication Data
US 2013/0224654 A1    Aug. 29, 2013

(30) Foreign Application Priority Data

Oct. 18, 2010  (JP) .................................. 2010-233754
Oct. 18, 2010  (JP) .................................. 2010-233884

(51) Int. Cl.
*G03F 7/004*    (2006.01)
*G03F 7/20*    (2006.01)
(Continued)

(52) U.S. Cl.
CPC ............... *G03F 7/004* (2013.01); *C08F 2/00* (2013.01); *C08F 120/28* (2013.01);
(Continued)

(58) Field of Classification Search
CPC ........ C08F 212/14; C08F 220/18; C08F 2/04; C08F 2/00; C08F 2/001; B01J 2219/00186; G03F 7/0392
(Continued)

(56) References Cited

U.S. PATENT DOCUMENTS 3,716,524 A * 2/1973 Cenci ............................ 528/376
4,663,268 A * 5/1987 Turner et al. .............. 430/270.1
(Continued)

FOREIGN PATENT DOCUMENTS

JP    57-120931 A    7/1982
JP    10-7703 A      1/1998
(Continued)

OTHER PUBLICATIONS

English translation of JP2003-246825 a, A (2003) from machine translation from AIPN Japan Patent Office National Center for Industrial Property Information and Training, generated Oct. 2, 2014, 21 pages.*

(Continued)

*Primary Examiner* — Cynthia Hamilton
(74) *Attorney, Agent, or Firm* — Oblon, McClelland, Maier & Neustadt, L.L.P.

(57) ABSTRACT

A target variable analysis unit (11) calculates the triad fractions of monomer units in the composition of a known polymer sample from the copolymerization reactivity ratios of the monomer units to obtain a target variable. A waveform processing unit (12) processes NMR measurements, signals, etc. An explanatory variable analysis unit (13) obtains explanatory variables from the amount of chemical shift and
(Continued)

signal strength in the NMR measurements of the known sample. A model generation unit (14) determines the regression equation of the regression model of the target variable and the explanatory variables by partial least squares regression, and obtains regression model coefficients. A sample analysis unit (15) uses the regression model to calculate the triad fractions for an unknown copolymer sample from the amount of chemical shift and signal strength in the NMR measurements of the unknown copolymer sample. By using a copolymer for lithography in which the total of the triad fractions obtained in this way is not more than 20 mole % in the copolymer, a resist composition with excellent solubility and sensitivity can be manufactured.

6 Claims, 11 Drawing Sheets

(51) Int. Cl.

| | | |
|---|---|---|
| *C08F 2/00* | (2006.01) | |
| *G01N 24/08* | (2006.01) | |
| *C08F 120/28* | (2006.01) | |
| *C08F 220/28* | (2006.01) | |
| *G03F 7/038* | (2006.01) | |
| *G03F 7/039* | (2006.01) | |
| *C08F 220/18* | (2006.01) | |
| *C08F 220/20* | (2006.01) | |

(52) U.S. Cl.
CPC ......... *C08F 220/28* (2013.01); *G01N 24/085* (2013.01); *G03F 7/0382* (2013.01); *G03F 7/0392* (2013.01); *G03F 7/0397* (2013.01); *G03F 7/20* (2013.01); *C08F 220/18* (2013.01); *C08F 220/20* (2013.01); *C08F 2220/283* (2013.01); *C08F 2400/02* (2013.01)

(58) Field of Classification Search
USPC .................................................. 430/269–331
See application file for complete search history.

(56) References Cited

U.S. PATENT DOCUMENTS

| | | | | |
|---|---|---|---|---|
| 5,444,140 | A * | 8/1995 | Paine et al. | 526/346 |
| 6,841,331 | B2 * | 1/2005 | Barclay et al. | 430/270.1 |
| 2008/0063974 | A1 * | 3/2008 | Shimizu | G03F 7/0397 430/270.1 |
| 2010/0222526 | A1 * | 9/2010 | Oikawa et al. | 526/60 |
| 2012/0111099 | A1 * | 5/2012 | Katou | G03F 7/0392 73/64.56 |
| 2012/0115086 | A1 * | 5/2012 | Yasuda et al. | 430/285.1 |

FOREIGN PATENT DOCUMENTS

| | | | |
|---|---|---|---|
| JP | 2001-201856 A | | 7/2001 |
| JP | 2002-90299 A | | 3/2002 |
| JP | 2002-145955 A | | 5/2002 |
| JP | 2002-340792 A | | 11/2002 |
| JP | 2003-246825 A | * | 9/2003 |
| JP | 2004-231950 A | | 8/2004 |
| JP | 2007-99839 A | | 4/2007 |
| JP | 2008-239889 A | | 10/2008 |
| JP | 2008-248244 A | | 10/2008 |
| JP | 2010-202699 A | | 9/2010 |
| JP | WO 2011/004787 A1 | * | 1/2011 |
| JP | 2011-247630 A | | 12/2011 |
| WO | WO-2011/004840 A1 | * | 1/2011 |
| WO | WO 2012/053434 A1 | | 4/2012 |

OTHER PUBLICATIONS

International Search Report dated Dec. 27, 2011 in PCT/JP2011/073623 with English Translation.
Shimpan Koubunshi Bunseki Handobukku [Polymer Analysis Handbook, New Edition] (Edited by Research Committee of Polymer Analysis, The Japan Society for Analytical Chemistry, Kinokuniya Company, 1995,pp. 185-, 233-, 694-, and the like), (with Partial English Translation).
Office Action issued Jun. 10, 2014 in Japanese Patent Application No. 2010-233753 (with English language translation).

* cited by examiner ic COPOLYMERS FOR LITHOGRAPHY AND METHOD FOR PRODUCING SAME, RESIST COMPOSITION, METHOD FOR PRODUCING SUBSTRATE WITH PATTERN FORMED THEREUPON, METHOD FOR EVALUATING COPOLYMERS, AND METHOD FOR ANALYZING COPOLYMER COMPOSITIONS

CROSS REFERENCE TO RELATED APPLICATIONS

The present application is a 35 U.S.C. §371 national stage patent application of International patent application PCT/JP11/73623, filed on Oct. 14, 2011, the text of which is incorporated by reference, and claims the benefit of the filing dates of Japanese Application No. 2010-233754, filed on Oct. 18, 2010, and Japanese Application No. 2010-233884, filed on Oct. 18, 2010, the text of which are also incorporated by reference.

TECHNICAL FIELD

The present invention relates to a copolymer for lithography and a method for producing the same, a resist composition, a method for producing a substrate with a pattern formed thereon, a method for evaluating a copolymer, and a method for analyzing a copolymer composition.

This application is based on and claims the benefit of priority from Japanese Patent Applications Nos. 2010-233754 and 2010-233884, filed on Oct. 18, 2010, the content of which is incorporated herein by reference.

BACKGROUND ART

Generally, in a polymerization reactor system, in order to measure the properties of a polymer, especially a copolymer, and control a polymerization reaction online, the properties thus measured must be analyzed.

An example of such a case is a property evaluation of a resist (composition for a resist), a type of copolymer, which is a composition for lithography used in a manufacturing process of a semiconductor element.

In recent years, in processes for manufacturing semiconductors, liquid crystal devices, and the like, rapid progress has been made in formation of a finer pattern using lithography. Examples of technology for formation of a finer pattern include a technology using shorter wave radiation on the resist upon pattern formation.

In recent years, KrF excimer laser (wavelength: 248 nm) lithographic technology has been introduced. Also, ArF excimer laser (wavelength: 193 nm) lithographic technology and EUV (wavelength: 13.5 nm) lithographic technology, which are intended to use shorter wavelengths, have been investigated.

Furthermore, for example, a so-called chemical amplification type resist has been proposed as a resist compound suitably applicable to shorten the wavelength of irradiation light and to pattern microfabrication. Such a chemical amplification type resist includes a polymer, which becomes soluble in alkali when an acid-eliminable group is dissociated by the action of an acid, and a photoacid generator. The resist composition has been further developed and improved.

An acrylic type polymer transparent to light with a wavelength of 193 nm has attracted attention as a chemical amplification resist polymer used in ArF excimer laser lithography.

As such an acrylic type polymer, copolymers for resist that are produced using, as monomers, (A) a (meth)acrylate to which an aliphatic hydrocarbon having a lactone ring is ester-bonded, (B) a (meth)acrylate to which a group dissociable by the action of an acid is ester-bonded, and (C) a (meth)acrylate to which a hydrocarbon group or an oxygen atom-containing heterocyclic group having a polar substituent is ester-bonded are disclosed (for example, refer to Patent Document 1).

Incidentally, a (meth)acrylate polymer is obtained by radical polymerization.

In a multi-component polymer produced from at least two types of monomers, the monomers have their respective copolymerization reaction rates. Thus, the copolymer composition ratio of the polymer in the early stage is different from that in the later polymerization stage. Namely, the resulting polymer has a composition distribution.

When a polymer has variations in the composition ratio of monomer units, the solubility of the copolymer tends to be less in a solvent. Thus, the preparation of a resist composition may be affected. For example, preparation of a resist composition takes a long time to dissolve the copolymer in a solvent, and causes an increase in the number of production steps due to generation of an insoluble substance. Also, the obtained resist composition tends to have insufficient sensitivity.

In addition, generally in a multi-component polymer, a chain order varies depending on the polymerization reaction rate between monomers. Since a copolymer having a large number of chains in which the monomer units are arranged successively tends to deteriorate resist performance, a copolymer with a reduced number of chains in which the monomer units are arranged successively has been desired.

On the other hand, for example, a method for obtaining a polymer having a narrow copolymer composition distribution has been disclosed that makes a difference between the feed rate of a monomer having a relatively higher polymerization rate to a monomer having a lower polymerization rate in the front end of the process and that in the back end of the process to obtain a resist having high resolution (for example, refer to Patent Documents 2 and 3).

In a copolymer for resist produced by a method of Patent Documents 2 and 3, a bias of monomer units incorporated into the copolymer is reduced and a proportion of the chain in which monomer units are arranged successively is smaller than in a method of simultaneously adding the above-described monomer, a polymerization solvent, a polymerization initiator, and a chain transfer agent in some cases into a polymerization apparatus, and therefore such a copolymer is superior in solubility in resist solvent and flatness of resist pattern sidewall.

However, with the methods described in the above Patent Documents 2 and 3, improvement in the solubility of a copolymer for lithography or the sensitivity of a resist composition may be insufficient.

With progress of formation of a finer pattern using lithography, there is a need for a copolymer for resist that is: lower in a proportion of chains in which monomer units (monomers of the same type) are arranged successively and/or smaller in variation in the composition ratio of the monomer units; industrially higher in resist sensitivity and/or in resolution; and superior in solubility in the resist solvent, than a conventional copolymer.

In general, the chain structure of a copolymer is determined from intensity of signals unique to factors, such as signals found in signals obtained by: a spectrochemical analysis method such as a nuclear magnetic resonance (NMR) method and an infrared absorption (IR) method; a separating analysis method such as a pyrolysis gas chromatography (PyGC) method; or a mass spectroscopic analysis (MS) method (for example, refer to Non-Patent Document 1).

However, there may be a case in which the signals obtained from the measurement result cannot clearly be separated, due to the increased number of constitutional units in a copolymer, due to overlap between characterizing signals of factors even if the number of constitutional units is small, or the like. In addition, precision may be low due to: time-consuming analysis of data obtained by the measurement; and likelihood of quantitative values obtained from the result of analysis.

Therefore, the result obtained may not be used effectively in quality management of copolymers and the like.

Meanwhile, in recent years, analysis called multivariate analysis or chemometrics that uses a method aimed at maximization of chemical information acquired from chemical data such as spectra and chromatograms obtained by various measurements by applying mathematical or statistical technique has been practiced. Examples of such analysis include a method of identifying a polymer material from a near-infrared spectrum and a method of measuring density (for example, refer to Patent Documents 4 and 5).

CITATION LIST

Patent Literature

Patent Document 1: Japanese Unexamined Patent Application, Publication No. 2002-145955
Patent Document 2: Japanese Unexamined Patent Application, Publication No. 2001-201856
Patent Document 3: Japanese Unexamined Patent Application, Publication No. S57-120931
Patent Document 4: Japanese Unexamined Patent Application, Publication No. 2002-90299
Patent Document 5: Japanese Unexamined Patent Application, Publication No. 2002-340792

Non-Patent Literature

Non-Patent Document 1: Shimpan Koubunshi Bunseki Handobukku [Polymer Analysis Handbook, New Edition] (Edited by Research Committee of Polymer Analysis, The Japan Society for Analytical Chemistry, Kinokuniya Company, pages 185-, 233-, 694-, and the like)

DISCLOSURE OF THE INVENTION

Problems to be Solved by the Invention

Using the analysis method of Patent Documents 4 and 5, in evaluation of a copolymer for resist, it is no longer required to prepare a composition for resist by actually using the produced copolymer for resist and other additives and then irradiate the composition for resist (resist for actual use) with light to develop, for evaluating properties of the resist.

As described above, the analysis method of Patent Documents 4 and 5 can evaluate performance of a copolymer for resist being produced in a simple way and can eliminate influence of a component other than the copolymer for resist. Therefore, the analysis method is effective for evaluation of properties of the copolymer for resist itself (lithography characteristics including photosensitivity in exposure, solubility in a solvent in development and the like) used in a resist composition.

In addition, in a lithography process in production of integrated circuit, evaluation of a composition for lithography other than the composition for resist, the composition for lithography used for formation of an antireflection film, a gap-fill film, a topcoat film and the like formed on a topside or a backside of the composition for resist applied on a semiconductor material, is as important as the composition for resist.

In other words, also in a composition for lithography containing a copolymer for lithography, it is important whether properties for microfabrication of high precision (lithography characteristics) are provided.

Also for the composition for lithography, evaluation of the lithography characteristics must be possible without actually performing a lithography process using the composition for lithography prepared by using the copolymer for lithography, as in the evaluation of the composition for resist.

The antireflection film is a composition for lithography formed on the backside of the film of the composition for resist, used for precision improvement of exposure of the composition for resist by suppressing reflection from the semiconductor material. The gap-fill film is a composition for lithography formed on the backside of the film of the composition for resist, used for precision improvement of exposure of the composition for resist by flattening unevenness of the semiconductor material. The topcoat film is a composition for lithography formed on the topside of the film of the composition for resist, used for protection of a surface of the composition for resist. The antireflection film, the gap-fill film, and the topcoat film are structures required for precision improvement of exposure of the lithography configuration in production of an integrated circuit and are indispensable in formation of finer pattern on the integrated circuit.

However, in Patent Document 4, Patent Document 5, Non-patent Document 1 and the like, since the quantitative determination of composition is an estimation using the PyGC method (pyrolysis chromatography), there may be a practical problem of the need for correction coefficient and a three dimensional plot, because pyrolysis efficiency may be different between types of the monomer units in the copolymer; pyrolysis products that reflect the monomer units cannot be obtained quantitatively; or the like.

The present invention has been made in view of the abovementioned problems, and an object thereof is to solve at least one of the following (1) to (5).
(1) To provide a copolymer for lithography that can improve the solubility in a solvent and the sensitivity of a resist composition when used therein.
(2) To provide a copolymer for lithography that can improve variations in the content ratio of monomer units in the copolymer, solubility in solvent, and the sensitivity of a resist composition when used therein, and a method for production thereof.
(3) To provide a resist composition using the copolymer for lithography, and a method for producing a substrate with a pattern formed thereon using the resist composition.
(4) To provide a method for evaluating a copolymer that simply evaluates a chain structure of the copolymer.
(5) To provide a method for analyzing a copolymer composition that analyzes an alignment state of monomer units in the copolymer.

Means for Solving the Problems

The abovementioned problems are solved by the following <1> to <12> of the present invention.

<1> A copolymer for lithography obtained by polymerizing at least two monomers $\alpha_1$ to $\alpha_n$ (n denoting an integer of at least 2) the copolymer for lithography being composed of monomer units $\alpha'_1$ to $\alpha'_n$ derived respectively from the monomers $\alpha_1$ to $\alpha_n$, wherein dimethyl-2,2'-azobisisobutylate is used to produce the copolymer for lithography as a polymerization initiator at the polymerization process, a total of triad fractions of the monomer units that are calculated by a copolymer evaluation method that calculates a triad fraction, which indicates a proportion of a triad of the monomer units of the same type in an entire composition in a copolymer composed of a plurality of monomer units, is no greater than 13 mol % of the copolymer, the copolymer evaluation method comprising the following processes (I) to (IV):

(I) a target variable analysis process of calculating the triad fraction of the monomer units of the same type in the composition of a polymer, which is a known sample, from the copolymerization reactivity ratio of the monomer unit using the following equation H;

(II) an explanatory variable analysis process of outputting an explanatory variable from an amount of chemical shift and signal strength in NMR measurements of the copolymer of the known sample;

(III) a model generation process of determining a regression equation of a regression model of the target variable and the explanatory variable by partial least squares regression, and generating a regression model coefficient; and (IV) a sample analysis process of using the regression model to calculate the triad fraction for the monomer units of the same type in an unknown copolymer sample, from the amount of chemical shift and signal strength in the NMR measurements of the unknown copolymer sample.

$$P\{jjj\}(\%) = 100 \times [M'_j] \times P_{jj} \times P_{jj} \quad (H)$$

$$P_{jj} = \frac{[M_j]}{\sum_{h=1}^{n} \frac{[M_h]}{r_{jh}}}$$

([$M'_j$] denoting a molar fraction of a monomer unit j in a copolymer; $P_{jj}$ denoting probability of reaction with the monomer (unit) j, j denoting a monomer unit of a growing end of the copolymer; [$M_j$] and [$M_h$] denoting molar fractions of monomer units j, h in a reaction system; and $r_{jh}$ denoting a copolymerization reactivity ratio of a reaction from the monomer (unit) j to the monomer (unit) h)

<2> A copolymer for lithography obtained by polymerizing at least two monomers $\alpha_1$ to $\alpha_n$ (n denoting an integer of at least 2) the copolymer for lithography being composed of monomer units $\alpha'_1$ to $\alpha'_n$ derived respectively from the monomers $\alpha_1$ to $\alpha_n$, wherein a large amount of a polymerization initiator to be fed during an early stage of a polymerization process is used to produce the copolymer for lithography, a total of triad fractions of the monomer units that are calculated by a copolymer evaluation method that calculates a triad fraction, which indicates a proportion of a triad of the monomer units of the same type in an entire composition in a copolymer composed of a plurality of monomer units, is no greater than 20 mol % of the copolymer, the copolymer evaluation method comprising the following processes (I) to (IV):

(I) a target variable analysis process of calculating the triad fraction of the monomer units of the same type in the composition of a polymer, which is a known sample, from the copolymerization reactivity ratio of the monomer unit using the following equation H;

(II) an explanatory variable analysis process of outputting an explanatory variable from an amount of chemical shift and signal strength in NMR measurements of the copolymer of the known sample;

(III) a model generation process of determining a regression equation of a regression model of the target variable and the explanatory variable by partial least squares regression, and generating a regression model coefficient; and (IV) a sample analysis process of using the regression model to calculate the triad fraction for the monomer units of the same type in an unknown copolymer sample, from the amount of chemical shift and signal strength in the NMR measurements of the unknown copolymer sample.

[Formula 1]

$$P\{jjj\}(\%) = 100 \times [M'_j] \times P_{jj} \times P_{jj} \quad (H)$$

$$P_{jj} = \frac{[M_j]}{\sum_{h=1}^{n} \frac{[M_h]}{r_{jh}}}$$

([$M'_j$] denoting a molar fraction of a monomer unit j in a copolymer; $P_{jj}$ denoting probability of reaction with the monomer (unit) j, j denoting a monomer unit of a growing end of the copolymer; [$M_j$] and [$M_h$] denoting molar fractions of monomer units j, h in a reaction system; and $r_{jh}$ denoting a copolymerization reactivity ratio of a reaction from the monomer (unit) j to the monomer (unit) h)

<3> A method for producing a polymer for lithography comprising a polymerization step of adding monomers and a polymerization initiator into a reactor dropwise to polymerize at least two monomers $\alpha_1$ to $\alpha_n$ (n denoting an integer of at least 2) in the reactor, thereby obtaining a polymer (P) composed of monomer units $\alpha'_1$ to $\alpha'_n$ ($\alpha'_1$ to $\alpha'_n$ denoting monomer units derived respectively from the monomers $\alpha_1$ to $\alpha_n$), solutions Sa (a being 1 to d, d denoting an integer of at least 1), Tb (b being 1 to e, e denoting an integer of at least 1), and Uc (c being 1 to f, f denoting an integer of at least 1) containing the monomers are used; and the polymerization step includes a main step of feeding the solutions Sa and Tb into the reactor and a later step of feeding the solution Uc into the reactor after completion of the main step, wherein, during the main step: feed of the solution Sa containing the monomers $\alpha_1$ to $\alpha_n$ in a first composition ratio into the reactor is started before or simultaneously with start of dropwise addition of the polymerization initiator into the reactor; and dropwise addition of the solution Tb containing the monomers $\alpha_1$ to $\alpha_n$ in a second composition ratio into the reactor is started after or simultaneously with start of feed of the solution Sa into the reactor, and the feed of the solution Sa is completed before completion of dropwise addition of the solution Tb, and wherein, given a target composition (unit: mol %) indicating a content ratio of the monomer units $\alpha'_1$ to $\alpha'_n$ in the polymer (P) to be obtained being $\alpha'_1:\alpha'_2: \ldots :\alpha'_n$, the second composition ratio, which is a composition ratio of the monomers in each of the solutions T1 to Te is the same as the target composition;

the composition ratio of the monomers in each of the solutions S1 to Sd is different from the target composition;

in the first composition ratio, which is a composition ratio of the monomers in a total of the solutions S1 to Sd, a proportion of a monomer having the lowest copolymerization reaction rate among the monomers $\alpha_1$ to $\alpha_n$ is greater than in the target composition;

in the later step, the composition ratio of the monomers in each of the solutions U1 to Uf is different from the target composition; and in the third composition, which is a composition ratio of the monomers in a total of the solutions U1 to Uf, a proportion of the monomer having the lowest copolymerization reaction rate among the monomers $\alpha_1$ to $\alpha_n$ is smaller than in the target composition.

<4> The method for producing a polymer for lithography according to the above <3>, in which, given a target composition (unit: mol %) indicating a content ratio of the monomer units $\alpha'_1$ to $\alpha'_n$ in the polymer (P) to be obtained being $\alpha'_1:\alpha'_2: \ldots :\alpha'_n$, content ratios of the monomer units in the first composition ratio, which is a composition ratio of the monomers in a total of the solutions S1 to Sd, are within a range of 0.8 to 1.2 times of respective values of the content ratios of the monomer units in S'a obtained by the following methods (1) to (4); and a total amount of the monomers contained in a total of the solutions U1 to Uf is 0.1 to 10 mass % of a total feed amount of the monomers.

(1) first, a dropping solution containing: 100 mass parts of a monomer mixture with the same monomer composition ratio as the target composition $\alpha'_1:\alpha'_2: \ldots :\alpha'_n$; a polymerization initiator; and a solvent is added dropwise at a constant rate into a reactor containing only the solvent, compositions $M_1:M_2: \ldots :M_n$ (unit: mol %) of the monomers $\alpha_1$ to $\alpha_n$ remaining in the reactor after respective passages of time from the start of the dropwise addition $t_1$, $t_2$, $t_3$ . . . , and a ratio (unit: mol %) $P_1:P_2: \ldots :P_n$ of the monomer units $\alpha'_1$ to $\alpha'_n$ in polymers respectively formed between $t_1$ and $t_2$, between $t_2$ and $t_3$, . . . is obtained;

(2) a time zone from $t_m$ to $t_{m+1}$ (m denoting an integer of at least 1) in which the ratio $P_1:P_2: \ldots :P_n$ is closest to the target composition $\alpha'_1:\alpha'_2: \ldots :\alpha'_n$ is determined;

(3) factors $F_1$, $F_2$ . . . $F_n$ are obtained from a value of $P_1:P_2: \ldots :P_n$ in the time zone from $t_m$ to $t_{m+1}$ and a value of $M_1:M_2: \ldots :M_n$ at the passage of time $t_m$, using the following equation $$F_1=P_1/M_1, F_2=P_2/M_2, \ldots F_n=P_n/M_n;$$

(4) composition of S'a (unit: mol %) is represented by $\alpha_{11}:\alpha_{12}: \ldots :\alpha_{1n}$ and the factors obtained in the above (3) are represented by $F_1$, $F_2$ . . . $F_n$, wherein $\alpha_{11}=a'_1/F_1$, $\alpha_{12}=\alpha'_2/F_2, \ldots \alpha_{1n}=\alpha'_n/F_n$.

<5> The method for producing a polymer for lithography according to the above <3> or <4>, in which, given a target composition (unit: mol %) indicating a content ratio of the monomer units $\alpha'_1$ to $\alpha'_n$ in the polymer (P) to be obtained being $\alpha'_1:\alpha'_2: \ldots :\alpha'_n$, content ratios of the monomer units in the third composition, which is a composition ratio of the monomers in a total of the solutions U1 to Uf, are within a range of 0.8 to 1.2 times of respective values of the content ratios of the monomer units in U'c obtained by the following methods (5) to (8).

(5) a dropping solution containing: 100 mass parts of a monomer mixture with the same monomer composition ratio as the target composition $\alpha'_1:\alpha'_2: \ldots :\alpha'_n$; a polymerization initiator; and a solvent, is added dropwise at a constant rate into a reactor containing only the solvent, compositions $M_1:M_2: \ldots :M_n$ (unit: mol %) of the monomers $\alpha_1$ to $\alpha_n$ remaining in the reactor after respective passages of time from the start of the dropwise addition $t_1$, $t_2$, $t_3$ . . . , and a ratio (unit: mol %) $P_1:P_2: \ldots :P_n$ of the monomer units $\alpha'_1$ to $\alpha'_n$ in polymers respectively formed between $t_1$ and $t_2$, between $t_2$ and $t_3$, . . . is obtained;

(6) a time zone from $t_m$ to $t_{m+1}$ (m denoting an integer of at least 1) in which the ratio $P_1:P_2: \ldots :P_n$ is closest to the target composition $\alpha'_1:\alpha'_2: \ldots :\alpha'_n$ is determined;

(7) factors $F_1$, $F_2$ . . . $F_n$ are obtained from a value of $P_1:P_2: \ldots :P_n$ in the time zone from $t_m$ to $t_{m+1}$ and a value of $M_1:M_2: \ldots :M_n$ at the passage of time $t_m$, using the following equation $$F_1=P_1/M_1, F_2=P_2/M_2, \ldots F_n=P_n/M_n;$$

(8) compositions of U'c (unit: mol %) are represented by $\alpha_{31}:\alpha_{32}: \ldots :\alpha_{3n}$ and the factors obtained in the above (7) are represented by $F_1$, $F_2$ . . . $F_n$ (the smallest factor among $F_1$ to $F_n$ is substituted by 0), wherein $\alpha_{31}=\alpha'_1 \times F_1/(\alpha'_1 \times F_1 + \alpha'_2 \times F_2 + \ldots + \alpha'_n \times F_n)$, $\alpha_{32}=\alpha'_2 \times F_2/(\alpha'_1 \times F_1 + \alpha'_2 \times F_2 + \ldots + \alpha'_n \times F_n)$, . . . $\alpha_{3n}=\alpha'_n \times F_n/(\alpha'_1 \times F_1 + \alpha'_2 \times F_2 + \ldots + \alpha'_n \times F_n)$.

<6> A polymer for lithography, wherein the polymer is obtained by the method according to the above <1> or <2>.

<7> A resist composition, comprising: the polymer for lithography according to the above <1> or <2>; and a compound that generates an acid when irradiated with active rays or radial rays.

<8> A method for producing a substrate with a pattern formed thereon, the method comprising: applying the resist composition according to the above <7> to a working surface of a substrate to form a resist film; exposing the resist film to light to form an exposed resist film; and developing the exposed resist film with a developing solution.

<9> A copolymer evaluation method that calculates a triad fraction, which indicates a proportion of a triad of the monomer units of the same type in an entire composition in a composition of copolymer composed of at least two types of monomer units, comprising:

a target variable analysis process in which a target variable analysis unit calculates the triad fraction of the monomer units of the same type in the composition of a polymer, which is a known sample, from the copolymerization reactivity ratio of the monomer unit using the following equation H;

an explanatory variable analysis process in which an explanatory variable analysis unit outputs an explanatory variable from an amount of chemical shift and signal strength in NMR measurements of the copolymer of the known sample;

a model generation process in which a model generation unit determines a regression equation of a regression model of the target variable and the explanatory variable by partial least squares regression, and generating a regression model coefficient; and a sample analysis process in which a sample analysis unit uses the regression model to calculate the triad fraction for the monomer units of the same type in an unknown copolymer sample, from the amount of chemical shift and signal strength in the NMR measurements of the unknown copolymer sample.

[Formula 2]

$$P\{jjj\}(\%) = 100 \times [M'_j] \times P_{jj} \times P_{jj} \quad (H)$$

$$P_{jj} = \frac{[M_j]}{\sum_{h=1}^{n} \frac{[M_h]}{r_{jh}}}$$

([M'$_j$] denoting a molar fraction of a monomer unit j in a copolymer; P$_{jj}$ denoting probability of reaction with the monomer (unit) j, j denoting a monomer unit of a growing end of the copolymer; [M$_j$] and [M$_h$] denoting molar fractions of monomer units j, h in a reaction system; and r$_{jh}$ denoting a copolymerization reactivity ratio of a reaction from the monomer (unit) j to the monomer (unit) h)

<10> A method for analyzing a copolymer composition in terms of an alignment state of monomer units in a copolymer, comprising:

a data extraction process in which a measurement data extraction unit extracts an NMR spectrum of a range including wavelengths of the monomers constituting the copolymer from the NMR spectrum of the copolymer as copolymer measurement data;

a principal component analysis process in which a principal component analysis unit performs a principal component analysis with respect to the chemical shift between the copolymer measurement data and monomer measurement data of the NMR spectra of the monomers as well as spectral intensity, with regard to first to n-th principal components corresponding to the number n of the monomers (n denoting an integer of at least 2);

a distance calculation process in which, in a principal component space of n-th dimension composed of principal component axes of the first principal component to the n-th principal component, a numerical value conversion unit obtains an evaluation distance between a comparison space of (n−1)-th dimension including all the coordinate points corresponding to principal component scores of the monomers on the principal component axes and a target coordinate point corresponding to a principal component score of the copolymer; and a property evaluation process in which a property evaluation unit evaluates properties of the copolymer based on the evaluation distance.

<11> A method for producing a copolymer comprising: a step of polymerizing at least two monomers to obtain a copolymer; and a step of evaluating the copolymer thus obtained by the copolymer evaluation method according to the above <9>.

<12> A method for producing a copolymer comprising: a step of polymerizing at least two monomers to obtain a copolymer; and a step of analyzing the copolymer thus obtained by the method for analyzing a copolymer according to the above <10>.

Effects of the Invention

According to the present invention, the triad fraction of the monomer units of the same type in a copolymer is reduced and a copolymer for lithography having superior solubility in solvent and high sensitivity when used in a resist composition can be obtained.

According to the present invention, the variation in the content ratio of monomer units and a variation in molecular weight are improved. In addition, a copolymer for lithography having superior solubility in solvent and high sensitivity when used in a resist composition can be obtained.

According to the present invention, a chemical amplification type resist composition having superior solubility in a resist solvent and high sensitivity can be obtained.

According to the present invention, a substrate with a high-precision fine resist pattern formed thereon can be stably formed.

According to the present invention, a copolymer chain of a copolymer can be simply evaluated, and characteristics of a composition obtained by using the copolymer can be evaluated without actually producing the composition.

According to the present invention, the randomness of a chain structure of a copolymer can be simply estimated, and characteristics of a composition obtained by using the copolymer can be evaluated without actually producing the composition.

Given this, in composition of a copolymer (copolymer for resist and copolymer for lithography), the randomness of a chain of monomers in the copolymer can be simply estimated, and characteristics of a composition (composition for resist and composition for lithography) containing the copolymer can be evaluated using the copolymer, without actually producing the composition.

In other words, in an embodiment of the method for analyzing a copolymer composition, using the NMR spectrum obtained by the NMR measurement, a comparison distance between a comparison space including coordinate points of homopolymers of all the monomers used and coordinate points of copolymer to be evaluated is obtained in a principal component space; the randomness of monomer arrangement in a chain structure of the copolymer is determined based on the comparison distance; and characteristics of a composition prepared by using the copolymer are evaluated based on the randomness, allowing a more simple evaluation of the composition than in conventional arts.

In the embodiment of the method for analyzing a copolymer composition, upon estimation of quantitative determination or chain distribution of the monomers in the polymer, since high heat is not used for preparation of a measurement sample, measurement deviation due to: a difference in pyrolisys efficiency of a sample depending on the temperature of heat processing; or difficulty in quantitatively obtaining pyrolysis products that reflect the constitutional units, is not caused, unlike in the conventional arts. In addition, a large number of samples is therefore not necessary for correction processing and the like, allowing a simple evaluation of a composition prepared with the copolymer.

As used herein, the "randomness" indicates that adjacent monomers are of different types, in other words characteristics of a chain state in which there are few blocks in which a plurality of same monomers are bound to each other in the chain structure.

MODE FOR CARRYING OUT THE INVENTION

Figure 1:
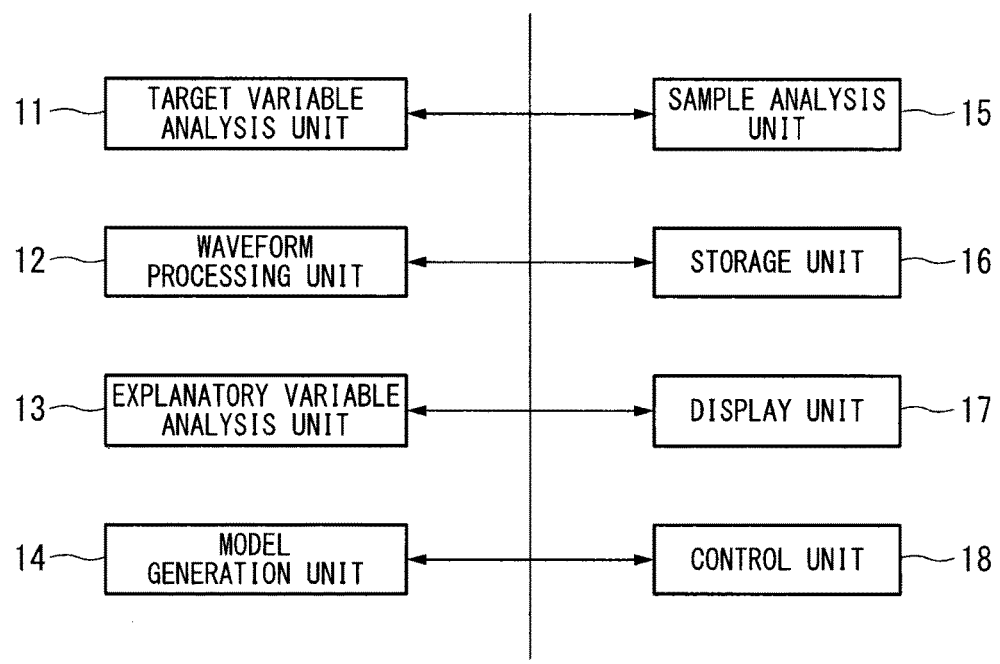
FIG. 1 is a block diagram illustrating a configuration example of a copolymer evaluation apparatus that evaluates a copolymer by a method for evaluating a copolymer according to an embodiment of the present invention.

As used herein, the "monomer unit" is a compositional unit in a copolymer, derived from each monomer. The monomer unit is also referred to as a constitutional unit. Meanwhile, simply "monomer" indicates a monomer before forming a copolymer.

In this specification, the term "(meth)acrylic acid" means acrylic acid or methacrylic acid. The term "(meth)acryloyloxy" means acryloyloxy or methacryloyloxy. In this specification, the weight-average molecular weight (Mw) and molecular weight distribution (Mw/Mn) of polymer are those in terms of polystyrene measured by gel permeation chromatography.

Production of Copolymer (Polymer (P))

The copolymer (also referred to as polymer (P)) in the embodiment of the present invention is composed of constitutional units $\alpha'_1$ to $\alpha'_n$ (wherein $\alpha'_1$ to $\alpha'_n$ represent constitutional units derived from the monomers $\alpha_1$ to $\alpha_n$, n denoting an integer of at least 2).

Here, n is preferably 6 or less from the point that the advantageous effects of the present invention can be easily obtained.

n is more preferably no greater than 5 and even more preferably no greater than 4 when the polymer (P) is a copolymer for semiconductor lithography (e.g. copolymer for resist).

When, for example, n=3, the polymer (P) is a ternary polymer P ($\alpha'_1/\alpha'_2/\alpha'_3$) constituted of monomer units $\alpha'_1$, $\alpha'_2$ and $\alpha'_3$. When n=4, the polymer (P) is a quaternary polymer P ($\alpha'_1/\alpha'_2/\alpha'_3/\alpha'_4$) constituted of monomer units $\alpha'_3$ and $\alpha'_4$.

There is no particular limitation to the use of the polymer (P). For example, the polymer (P) is preferably a polymer for lithography that is used in a lithographic step. Examples of the copolymer for lithography include a resist polymer, copolymer for an antireflection film that is used for forming an antireflection film (TARO) formed on the topside of a resist film or antireflection film (BARC) formed on the backside of a resist film, copolymer for a gap-fill film used for forming a gap-fill film, and copolymer for a topcoat film used for forming a topcoat film.

The weight-average molecular weight (Mw) of the copolymer for lithography is preferably 1,000 to 200,000, and more preferably 2,000 to 40,000. The distribution of molecular weight (Mw/Mn) is preferably 1.0 to 10.0 and more preferably 1.1 to 4.0.

There is no particular limitation to the monomer unit of the polymer (P) and the monomer unit is suitably selected according to use and characteristic requirements.

The copolymer for resist preferably has a monomer unit having an acid-dissociable group and a monomer unit having a polar group. The copolymer for resist may also have known constitutional units as necessary.

The weight-average molecular weight (Mw) of the copolymer for resist is preferably 1,000 to 100,000 and more preferably 3,000 to 30,000. The distribution of molecular weight (Mw/Mn) is preferably 1.0 to 3.0 and more preferably 1.1 to 2.5.

The copolymer for an antireflection film preferably has a monomer unit having, for example, a light-absorbing group. This copolymer preferably has a monomer unit having a functional group that is curable by reaction with a curing agent and the like to avoid mixing of the resist film with the copolymer for an antireflection film. Examples of this reactive functional group include an amino group, an amide group, a hydroxyl group, and an epoxy group.

The light-absorbing group is a group having high ability to absorb light that can sensitize light-sensitive components in the resist composition and has a wavelength falling in a prescribed wavelength range. Specific examples of the light-absorbing group include a group having a ring structure (may have optional substituents) such as an anthracene ring, a naphthalene ring, a benzene ring, a quinoline ring, a quinoxaline ring, and a thiazole ring. When KrF laser light is used as the radiation light, the light-absorbing group is preferably an anthracene ring or anthracene rings having optional substituents. When ArF laser light is used as the radiation light, the light-absorbing group is preferably a benzene ring or benzene rings having optional substituents.

Examples of the above optional substituent include a phenolic hydroxyl group, alcoholic hydroxyl group, carboxyl group, carbonyl group, ester group, amino group, or amide group.

Examples of the monomer providing monomer units having such a light-absorbing group may include styrenes such as styrene, α-methylstyrene, p-methylstyrene, p-hydroxystyrene, and m-hydroxystyrene and their derivatives, and aromatic group-containing esters having an ethylenic double bond such as substituted or unsubstituted phenyl (meth)acrylates, substituted or unsubstituted naphthalene (meth)acrylates, and substituted or unsubstituted anthracenemethyl(meth)acrylate.

Particularly, a copolymer for an antireflection film which contains a protective or non-protective phenolic hydroxyl group as this substituent is preferable from the viewpoint of obtaining superior developing characteristics and high resolution.

Examples of the monomer unit/monomer having the above light-absorbing group include benzyl(meth)acrylate (m-6 in Examples) and p-hydroxyphenyl(meth)acrylate.

The proportion of the monomer unit having the light-absorbing group to all monomer units (100 mol %) is preferably 10 to 100 mol %.

The copolymer for a gap-fill film preferably has a suitable viscosity allowing it to flow into a narrow gap. Moreover, the copolymer for a gap-fill film preferably has a monomer unit having a reactive functional group that is curable by reacting with a curing agent to avoid the mixing of the gap-fill film copolymer with the resist film or antireflection film.

Specific examples of the polymer for a gap-fill film include copolymers of hydroxystyrene and monomers such as styrene, alkyl(meth)acrylate and hydroxyalkyl(meth)acrylate.

Examples of the copolymer for a topcoat film that is used for immersion lithography include copolymers containing a monomer unit having a carboxyl group and copolymers containing a monomer unit having a fluorine-containing group substituted with a hydroxyl group.

Monomer Unit/Monomer

The polymer (P) is obtained by polymerizing monomers $\alpha_1$ to $\alpha_n$ corresponding to monomer units $\alpha'_1$ to $\alpha'_n$. The monomer is preferably a compound having a vinyl group. The monomer is preferably a compound that is radically polymerized with ease. Particularly, (meth)acrylate has high transparency to exposure light having a wavelength of 250 nm or less.

Hereinafter, monomer units and monomers corresponding to the monomer units when the polymer (P) is a copolymer for resist are described.

(Monomer Unit/Monomer Having Acid-Eliminable Group)

The copolymer for resist preferably has an acid-eliminable group. The term "acid-eliminable group" used herein is a group having a bond cleaved by the action of an acid. Some or all of the acid-eliminable groups are eliminated from the main chain of the polymer by cleavage of the bond.

In the composition for a resist, the polymer having a monomer unit having an acid-eliminable group reacts with an acid component to be soluble in an alkaline solution, thereby allowing the formation of a resist pattern.

As a monomer unit having an acid-eliminable group, a monomer unit derived from a known monomer having an acid-eliminable group can be exemplified.

The proportion of the monomer unit having an acid-eliminable group to all monomer unit (100 mol %) constituting the polymer is preferably at least 20 mol % and more preferably at least 25 mol %, from the viewpoint of sensitivity and resolution. This proportion is preferably 60 mol % or less, more preferably 55 mol % or less, and even more preferably 50 mol % or less from the viewpoint of adhesion to a substrate or the like.

Any monomer may be used as the monomer having an acid-eliminable group as long as it has an acid-eliminable group and a polymerizable multiple bond. A known compound may be used as the monomer having an acid-eliminable group. The polymerizable multiple bond means a multiple bond which is cleaved in a polymerization reaction to form a copolymer chain. The polymerizable multiple bond is preferably an ethylenic double bond.

Specific examples of the monomer having an acid-eliminable group include (meth)acrylates having an aliphatic hydrocarbon group having 6 to 20 carbon atoms and an acid-dissociable group. The aliphatic hydrocarbon group may be connected to an oxygen atom constituting the ester bond of the (meth)acrylate either directly or through a connecting group such as an alkylene group.

The (meth)acrylate has, for example, an aliphatic hydrocarbon group having 6 to 20 carbon atoms. Also, the (meth)acrylate is, for example, a (meth)acrylate having a tertiary carbon atom at the position where it is bonded with an oxygen atom constituting an ester bond, or a (meth)acrylate containing an aliphatic hydrocarbon group having 6 to 20 carbon atoms which is bonded to a —COOR group (R represents a tertiary hydrocarbon group, a tetrahydrofuranyl group, a tetrahydropyranyl group, or an oxepanyl group, which may have a substituent) directly or through a connecting group.

When, particularly, a resist composition to be applied to a pattern formation method using light having a wavelength of no higher than 250 nm to expose is produced, preferable examples of the monomer containing an acid-eliminable group include 2-methyl-2-adamantyl(meth)acrylate, 2-ethyl-2-adamantyl(meth)acrylate, 2-isopropyl-2-adamantyl(meth)acrylate, 1-(1'-adamantyl)-1-methylethyl(meth)acrylate, 1-methylcyclohexyl(meth)acrylate, 1-ethylcyclohexyl(meth)acrylate, 1-methylcyclopentyl(meth)acrylate, 1-ethylcyclopentyl(meth)acrylate, and 1-ethylcyclooctyl(meth)acrylate.

Among these compounds, 1-ethylcyclohexylmethacrylate (m-2 in Examples), 2-ethyl-2-adamantylmethacrylate (m-5 in Examples), 2-methyl-2-adamantylmethacrylate (m-11 in Examples), 1-ethylcyclopentylmethacrylate and 2-isopropyl-2-adamantyl(meth)acrylate are more preferable.

The constitutional unit having an acid-eliminable group may be used singly or in combination of at least two, as necessary.

(Monomer Unit/Monomer Having Polar Group)

Specific examples of the "polar group" include a hydroxy group, a cyano group, an alkoxy group, a carboxyl group, an amino group, a carbonyl group, a fluorine atom-containing group, a sulfur atom-containing group, a lactone skeleton-containing group, an acetal structure-containing group, and an ether bond-containing group.

Among these groups, the copolymer for resist to be applied to a pattern formation method using light having a wavelength of no greater than 250 nm to expose preferably has a monomer unit having a lactone skeleton. Moreover, the copolymer for resist preferably has a monomer unit having a hydrophilic group that will be described later.

(Monomer Unit/Monomer Having Lactone Skeleton)

Examples of the lactone skeleton include lactone skeletons having about a 4- to 20-membered ring. The lactone skeleton may be a single ring only containing a lactone ring or may contain a lactone ring and an aliphatic or aromatic carbon ring or hetero-ring condensed with the lactone ring.

In a case in which the copolymer contains a monomer unit having a lactone skeleton, the content of the monomer unit is preferably at least 20 mol %, and more preferably at least 35 mol %, of all monomer units (100 mol %) from the viewpoint of adhesion to, for example, the substrate. Also, the content is preferably 60 mol % or less, more preferably 55 mol % or less and even more preferably 50 mol % or less from the viewpoint of sensitivity and resolution.

As a monomer unit having a lactone skeleton, a monomer unit derived from a monomer having a lactone skeleton can be exemplified.

The monomer having a lactone skeleton is preferably at least one type selected from the group consisting of methacrylates having a substituted or unsubstituted δ-valerolactone and monomers having a substituted or unsubstituted γ-butyrolactone ring, and more preferably a monomer having an unsubstituted γ-butyrolactone ring.

Specific examples of the monomer having a lactone skeleton include β-(meth)acryloyloxy-β-methyl-δ-valerolactone, 4,4-dimethyl-2-methylene-γ-butyrolactone, β-(meth)acryloyloxy-γ-butyrolactone, β-(meth)acryloyloxy-β-methyl-γ-butyrolactone, α-(meth)acryloyloxy-γ-butyrolactone, 2-(1-(meth)acryloyloxy)ethyl-4-butanolide, pantoyllactone (meth)acrylate, 5-(meth)acryloyloxy-2,6-norbornanecarbolactone, 8-methacryloxy-4-oxatricyclo[5.2.1.0$^{2,6}$]decan-3-one, and 9-methacryloxy-4-oxatricyclo[5.2.1.0$^{2,6}$]decan-3-one. Also, examples of a monomer having an analogous structure include methacryloyloxysuccinic acid anhydride.

Among these compounds, α-methacryloyloxy-γ-butyrolactone (m-1 in Examples), α-acryloyloxy-γ-butyrolactone (m-4 in Examples), 5-metacryloyloxy-2,6-norbornanecarbolactone, and 8-methacryloxy-4-oxatricylo[5.2.1.0$^{2,6}$]decan-3-one are more preferable.

One type of monomer having a lactone skeleton may be singly used. At least two types of monomers having a lactone skeleton may be combined upon use.

(Monomer Unit/Monomer Having Hydrophillic Group)

The term "hydrophilic group" in this specification means at least one type among —C(CF$_3$)$_2$—OH, hydroxy group, cyano group, methoxy group, carboxyl group, and amino group.

Among these groups, the copolymer for resist which is applied to the pattern formation method using light having a wavelength of no greater than 250 nm to expose preferably has a hydroxy group or cyano group as the hydrophilic group.

The content of the monomer unit having a hydrophilic group in the copolymer to all monomer units (100 mol %) from the viewpoint of the rectangularity of a resist pattern is preferably 5 to 40 mol %. The upper limit is more preferably no greater than 35 mol %, even more preferably no greater than 30 mol %, and particularly preferably no greater than 25 mol %. The lower limit is more preferably at least 10 mol %.

Examples of the monomer having a hydrophilic group include: (meth)acrylates having a terminal hydroxy group; derivatives having a substituent, such as an alkyl group, a hydroxy group, or a carboxyl group, on a hydrophilic group of a monomer;

and monomers having a cyclic hydrocarbon group (for example, cyclohexyl(meth)acrylate, 1-isobornyl(meth)acrylate, adamantyl(meth)acrylate, tricyclodecanyl(meth)acrylate, dicyclopentyl(meth)acrylate, 2-methyl-2-adamantyl (meth)acrylate, 2-ethyl-2-adamantyl(meth)acrylate, styrene, vinylnaphthalene, naphthyl(meth)acrylate, benzyl(meth) acrylate, phenyl(meth)acrylate and the like) and having a hydrophilc group such as a hydroxy group or a carboxyl group, as a substituent.

Specific examples of the monomer having a hydrophilic group include a (meth)acrylic acid (m-10 in Examples), 2-hydroxyethyl(meth)acrylate (m-7 in Examples), 3-hydroxypropyl(meth)acrylate, 2-hydroxy-n-propyl(meth)acrylate, 4-hydroxybutyl(meth)acrylate, 3-hydroxyadamantyl(meth)acrylate, 2- or 3-cyano-5-norbornyl(meth)acrylate, 2-cyanomethyl-2-adamantyl(meth)acrylate, hydroxystyrene, and hydroxyvinylnaphthalene. Among them, 3-hydroxyadamantyl(meth)acrylate, 2- or 3-cyano-5-norbornyl (meth)acrylate, and 2-cyanomethyl-2-adamantyl(meth) acrylate are preferable from the viewpoint of adhesion to, for example, a substrate.

Among these compounds, 3-hydroxyadamantyl(meth) acrylate (m-3 in Examples), 2-cyanomethyl-2-adamantyl (meth)acrylate, hydroxystyrene, and hydroxyvinylnaphthalene (m-12 in Examples) are more preferable.

These monomers having a hydrophilic group may be used either singly or in combinations of at least two.

(Other Monomer Unit/Monomer)

The polymer (P) can contain a monomer unit derived from known monomers (other monomers) in addition to the above, as necessary. For example, the copolymer for resist which is applied to the pattern formation method using light having a wavelength of no greater than 250 nm to expose can contain a monomer unit derived from a monomer represented by the following formula (i) or (ii).

[Chemical Formula 1]

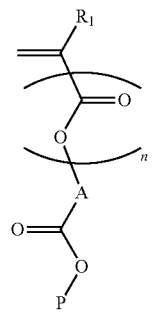

(i)

[Chemical Formula 2]

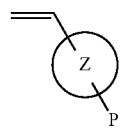

(ii)

In (i) and (ii), R$_1$ denotes H, F, methyl group, or trifluoromethyl group. n denotes an integer of 0 to 2. A denotes an alkyl group, alkenyl group, or oxoalkyl group; or an aryl group, aralkyl group, or aryl oxoalkyl group. P denotes a group producing an acid in response to active rays, radial rays, or heat. Z denotes a cyclic bivalent hydrocarbon group having 2 to 20 carbon atoms that may contain a hetero atom.

Specific examples of group P include sulfonium salt, iodonium salt skeleton.

In a copolymer containing a monomer unit derived from the monomer represented by the above formula (i) or (ii), a group (group P in the formula (i) or (ii)) that generates an acid when irradiated with active rays or radial rays is bound in the polymer chain. A composition containing such a copolymer has acid generation areas being uniformly dispersed and can provide superior sensitivity, resolution, pattern roughness and the like when used for a resist, and is therefore preferable.

Other examples of monomer include linear or branched (meth)acrylate, aromatic alkenyl compound, and anhydride of carboxylic acid.

Examples of the linear or branched (meth)acrylate include: methyl(meth)acrylate (m-8 in Examples); ethyl (meth)acrylate; 2-ethylhexyl(meth)acrylate; n-propyl(meth) acrylate; isopropyl(meth)acrylate; butyl(meth)acrylate; isobutyl(meth)acrylate; methoxymethyl(meth)acrylate; n-propoxyethyl(meth)acrylate; isopropoxyethyl(meth)acrylate; n-butoxyethyl(meth)acrylate; isobutoxyethyl(meth) acrylate; tert-butoxyethyl(meth)acrylate; 2-ethoxyethyl (meth)acrylate; 1-ethoxyethyl(meth)acrylate; 2,2,2- trifluoroethyl(meth)acrylate; 2,2,3,3-tetrafluoro-n-propyl (meth)acrylate; 2,2,3,3,3-pentafluoro-n-propyl(meth) acrylate; α-(tri)fluoromethyl methylacrylate; α-(tri) fluoromethyl ethylacrylate; α-(tri)fluoromethyl 2-ethylhexyl acrylate; α-(tri)fluoromethyl n-propyl acrylate; α-(tri)fluoromethyl isopropyl acrylate; α-(tri)fluoromethyl n-butyl acrylate; α-(tri)fluoromethyl isobutyl acrylate; α-(tri)fluoromethyl tert-butyl acrylate; α-(tri)fluoromethyl methoxymethyl acrylate; α-(tri)fluoromethyl ethoxyethyl acrylate; α-(tri)fluoromethyl n-propoxyethyl acrylate; α-(tri)fluoromethyl isopropoxyethyl acrylate; α-(tri)fluoromethyl n-butoxyethyl acrylate; α-(tri)fluoromethyl isobutoxyethyl acrylate; and α-(tri)fluoromethyl tert-butoxyethyl acrylate.

Examples of the aromatic alkenyl compound include styrene (m-9 in Examples), α-methylstyrene, vinyltoluene and the like.

Examples of the anhydride of carboxylic acid include maleic anhydride, itaconic acid anhydride and the like.

In addition, as other monomer units, ethylene, propylene, norbornene, tetrafluoroethylene, acrylamide, N-methylacrylamide, N,N-dimethylacrylamide, vinyl chloride, vinyl fluoride, vinylidene fluoride, vinylpyrrolidone can also be copolymerized.

Polymerization Initiator

Polymerization initiators, which are decomposed by heat to generate radicals efficiently, are preferable. It is also preferable to use a polymerization initiator having a ten-hour half-life temperature lower than the polymerization temperature. When, for example, a copolymer for lithography is produced, the polymerization temperature is preferably 50 to 150° C. Also, when a copolymer for lithography is produced, it is preferable to use a polymerization initiator having a ten-hour half-life temperature of 50 to 70° C. In order that the polymerization initiator be decomposed efficiently, the difference between the ten-hour half-life temperature and polymerization temperature of the polymerization initiator is preferably at least 10° C.

Examples of the polymerization initiator include azo compounds such as 2,2'-azobisisobutyronitrile, dimethyl-2,2'-azobisisobutylate, 2,2'-azobis(2,4-dimethylvaleronitrile), and 2,2'-azobis(2-(2-imidazoline-2-yl)propane and organic peroxides such as 2,5-dimethyl-2,5-bis(tert-butylperoxy) hexane, and di(4-tert-butylcyclohexyl)peroxydicarbonate. Azo compounds are more preferable.

These compounds are available as commercial products. For example, dimethyl-2,2'-azobisisobutylate (trade name: V601, manufactured by Wako Pure Chemical Industries Ltd., ten-hour half-life temperature: 66° C.) and 2,2'-azobis(2,4-dimethylvaleronitrile (trade name: V65, manufactured by Wako Pure Chemical Industries Ltd., ten-hour half-life temperature: 51° C.) may be preferably used.

Solvent

A polymerization solvent may be used in a polymerization process. For example, any one of the following polymerization solvents may be used.

Ethers: chain ether (for example, diethyl ether and propylene glycol monomethyl ether (hereinafter referred to as "PGME" where necessary)), cyclic ethers (for example, tetrahydrofuran (hereinafter referred to as "THF" where necessary), 1,4-dioxane and the like.

Esters: methyl acetate, ethyl acetate, butyl acetate, ethyl lactate, butyl lactate, propylene glycol monomethyl ether acetate (hereinafter referred to as "PGMEA" where necessary), γ-butyrolactone and the like.

Ketones: acetone, methyl ethyl ketone (hereinafter referred to as "MEK" where necessary), methyl isobutyl ketone (hereinafter referred to as "MIBK" where necessary) and the like.

Amides: N,N-dimethylacetamide, N,N-dimethylformamide and the like.

Sulfoxides: dimethylsulfoxide and the like.

Aromatic hydrocarbons: Benzene, toluene, xylene and the like.

Aliphatic hydrocarbons: hexane and the like.

Alicyclic hydrocarbons: cyclohexane and the like.

One type of polymerization solvent may be singly used. Also, at least two types of polymerization solvents may be combined prior to use.

The amount of the polymerization solvent is, for example, preferably such an amount that the solid content of a solution (polymerization reaction solution) in a reactor is about 20 to 40% by mass when the polymerization reaction is completed, though no particular limitation is imposed on the amount.

Polymerization Method

Examples of a polymerization method to produce the polymer (P) include the known polymerization methods such as a bulk polymerization method, a solution polymerization method, a suspension polymerization method, an emulsion polymerization method and the like. Among these, the solution polymerization method is desirable because light transmittance is not reduced, thereby facilitating a process of removing monomers remaining after polymerization reaction and making the molecular weight of the copolymer relatively low.

The solution polymerization method may be performed in such a way that a reactor is charged with a solvent and all monomers and reaction takes place (hereinafter referred to as a batch method); however, a dropping polymerization method, in which the monomers and the polymerization initiator are added dropwise to the reactor, is preferable because a copolymer having smaller triad fraction of monomer units of the same type can be produced more easily. The dropping polymerization method may be performed in such a way that all monomers used for forming a polymer are supplied dropwise to a solvent in the reactor (hereinafter also referred to as "total dropping method") or in such a way that a part of monomers is added to the reactor in advance and the rest of monomers are added dropwise thereto (hereinafter also referred to as "partial dropping method").

The following polymerization method (Z1) or (Z2) is particularly preferable. The polymerization method (Z1) controls in the early stage of a polymerization reaction so that the variation in monomer composition ratio in a resulting copolymer is reduced, and the polymerization method (Z2) controls in the early and later stages of a polymerization reaction so that the variation in monomer composition ratio in a resulting copolymer is reduced.

Polymerization Method (Z1)

The reactor is charged with a first solution containing monomers in a first composition ratio in advance. Then, the solution in the reactor is heated to a predetermined polymerization temperature, and then, at least one dropping solution containing the monomer is added in the reactor. The first solution can be fed gradually into the reactor, in a dropwise manner and the like.

If a solution having the same monomer composition ratio as the dropping solution is uniformly added dropwise for a predetermined time period, without charging the reactor with the monomer in advance, the monomer with a high consumption rate in the polymerization reaction is incorporated into a copolymer in the early stage of polymerization, in a proportion smaller than in a desired composition rate. This leads to variation in monomer composition ratio and chain structure.

Therefore, in the present method, it is preferable that the composition ratio (content ratio) of the monomer with a low monomer consumption rate is set to be greater in the first solution to charge the reactor in advance, than the composition ratio of said monomer in a total amount of solutions used for the polymerization reaction.

More specifically, a polymerization method in which at least two monomers $\alpha_1$ to $\alpha_n$ (n denoting an integer of at least 2) are polymerized in a reactor while the monomers and the polymerization initiator are added dropwise to the reactor, to obtain a polymer (P) comprising constitutional units $\alpha'_1$ to $\alpha'_n$ (wherein $\alpha'_1$ to $\alpha'_n$ represent constitutional units derived from the monomers $\alpha_1$ to $\alpha_n$), including the following steps (VI) and (VII), is preferable.
(VI) feeding a first solution containing the monomers $\alpha_1$ to $\alpha_n$ in a first composition ratio, which is a proportion allowing polymerization in a stationary state from the early stage according to reaction rates of the monomers, into the reactor, before or simultaneously with start of dropwise addition of the polymerization initiator into the reactor;
(VII) given a target composition (unit: mol %) indicating a content ratio of the monomer units $\alpha'_1$ to $\alpha'_n$ in the polymer (P) to be obtained being $\alpha'_1:\alpha'_2:\ldots:\alpha'_n$ feeding a second solution containing the monomers $\alpha_1$ to $\alpha_n$ in the same composition as the target composition to the reactor after or simultaneously with start of the feeding of the first solution to the reactor.

In this method, the first composition ratio is designed so that, when the ratio of the contents of the monomers existing in the reactor is the first composition ratio, the ratio of the contents of the composition units of a polymer molecule generated just after the above second solution is added dropwise to the reactor is equal to the target composition ratio.

In this case, the ratio of the contents of the constitutional units of a polymer molecule generated just after the above second solution is added dropwise is equal to the ratio of the contents (target composition ratio) of the monomers in the second solution to be added dropwise, and therefore, the content ratio of the monomers left in the reactor just after the dropwise addition is always fixed (first composition ratio). Therefore, when the second solution is successively added dropwise to such a reactor, a stationary state under which a polymer molecule having the target composition ratio is successively produced is obtained.

Polymerization Method (Z2)

Meanwhile, the monomer with a low consumption rate in the polymerization reaction is incorporated into a copolymer in the later stage of polymerization, in a proportion greater than in a desired composition rate.

This leads to variation in monomer composition ratio and chain structure. Given this, in this method, it is preferable to change the composition of the dropping solution between the early stage and the later stage of polymerization, by using at least two dropping solutions containing monomers to be fed into the reactor after heating the solution in the reactor up to a predetermined polymerization temperature, since it is easy to produce a copolymer with reduced variation in copolymer composition. For example, in the method using the first solution and the second solution (dropping solution), a dropping solution (third solution) that is different in composition from those solutions is added dropwise after completion of dropwise addition of the second solution.

The dropping solution added dropwise in the later stage of polymerization is preferably lower in proportion of monomer with the lowest consumption rate than the target composition, and more preferably free of the monomer with the lowest consumption rate. In addition, a total amount of monomers contained in the dropping solution to be added dropwise in the later stage of polymerization is 0.1 to 10 mass %, preferably 0.1 to 7.5 mass %, and more preferably 0.1 to 5 mass % of the total feed amount of monomers.

In the polymerization methods (Z1), (Z2), the polymerization initiator can either be contained in the dropping solution containing the monomers or be added dropwise to the reactor separately from the monomers.

A rate of dropwise addition can either be constant until the end of dropwise addition or be varied in multiple levels according to consumption of the monomers. The dropwise addition can be either consecutive or intermittent.

The polymerization temperature is preferably 50 to 150° C.

As a solvent for the first solution and the dropping solution, the above-exemplified polymerization solvent can be used.

Refining Method

A copolymer solution produced by the solution polymerization is diluted to an appropriate solution viscosity with a good solvent such as 1,4-dioxane, acetone, THF, MEK, MIBK, gamma-butyrolactone, PGMEA, PGME, and DMF as necessary, and then added dropwise into a large amount of poor solvent such as methanol, water, hexan, and heptane, thereby precipitating the copolymer. This process is generally referred to as reprecipitation, and is quite effective for removing unreacted monomers and the polymerization initiator remaining in a polymerization solution.

The unreacted substances remaining in the solution may impair the resist performance, and therefore it is preferable to remove the unreacted substances as much as possible. In some cases, the reprecipitation process may be unnecessary. Thereafter, the precipitate is filtered and dried, thereby obtaining a copolymer. Alternatively, after filtration, the copolymer can be used in a form of wet powder without drying.

Yet alternatively, the copolymer solution thus produced can be used as is, or after dilution with an appropriate solvent, as the resist composition. Here, an additive such as a preservation stabilizer can be added accordingly.

Embodiment of Method for Producing Copolymer for Lithography (Z2')

For producing a copolymer for lithography using the method that controls in the early and later stages of a polymerization reaction so that the variation in monomer composition ratio in a resulting copolymer is reduced (polymerization method (Z2)), the following method (an embodiment of a method for producing a copolymer for lithography (Z2')) is preferable.

A method for producing the copolymer of the present embodiment comprises a polymerization step in which at least two types of monomers $\alpha_1$ to $\alpha_n$ are polymerized while the monomers and a polymerization initiator are added dropwise to a reactor to obtain a polymer (P) constituted of monomer units $\alpha'_1$ to $\alpha'_n$.

The polymerization step is performed by the radical polymerization method. In the present embodiment, the dropping polymerization method is used in which the monomers are polymerized while the monomers and a polymerization initiator are added dropwise to a reactor.

In the present embodiment, solutions Sa (a being 1 to d, d denoting an integer of at least 1), Tb (b being 1 to e, e denoting an integer of at least 1), and Uc (c being 1 to f, f denoting an integer of at least 1) containing monomers are used.

The solutions Sa, Tb, and Uc preferably include a solvent. The polymerization step in the present embodiment includes a main step of feeding the solutions Sa and Tb into the reactor and a later step of feeding the solution Uc into the reactor after completion of feeding of the solutions Sa and Tb.

Main Step

First, the main step will be described below.

(Solution Tb)

The solution Tb is a collective designation of solutions T1, T2, . . . Te (e denoting an integer of at least 1) used in the main step. As the solution Tb, only one solution (only T1) may be used, or at least two solutions (T1, T2 . . . Te) may be used. The upper limit of e is not particularly limited; however, practically preferably no greater than 4, and more preferably no greater than 3, for avoiding complication of operation.

The ratio of the contents (second composition ratio) of the monomers in the solution Tb is equal to the target composition ratio showing the ratio of the contents of the monomer units $\alpha'_1$ to $\alpha'_n$ in the polymer (P) to be obtained.

In a case of using at least 2 solutions as the solution Tb, the second composition ratio of the solution Tb means composition ratio of monomers in each of T1 to Te. In other words, the monomer composition ratio of each of T1 to Te is the same as the target composition.

For example, when the polymer (P) is a ternary polymer obtained by copolymerizing monomers x, y and z and the target composition ratio (mol %, the same as follows) is x':y':z', the second composition ratio (mol %, the same as follows) x:y:z is equal to x':y':z'. It should be noted that, in the present embodiment, in order to obtain an intended effect, it is most preferable that the second composition ratio (mol %) is equal to the target composition (mol %); however, a difference from the target composition within a range of ±10%, preferably within a range of ±5%, is acceptable. In other words, with a difference within the abovementioned range, the second composition ratio is considered to be equal to the target composition.

The solution Tb is added dropwise to the reactor.

(Solution Sa)

The solution Sa is a collective designation of solutions S1, S2, . . . Sd (d denoting an integer of at least 1) used in the main step. As the solution Sa, only one solution (only S1) may be used, or at least two solutions (S1, S2 . . . Sd) may be used. The upper limit of d is not particularly limited; however, practically preferably no greater than 5, and more preferably no greater than 4, for avoiding complication of operation.

In a case of using at least 2 solutions as the solution Sa, the content ratio of monomers in the solution Sa (first composition ratio) means composition ratio of monomers in a total of S1 to Sd.

The composition ratios of monomers in the solutions S1 to Sd may be either the same or different from each other, and are different from the target composition. In the first composition ratio, a proportion of a monomer having the lowest copolymerization reaction rate among the monomers $\alpha_1$ to $\alpha_n$ is greater than in the target composition. The ratio of the contents (mol %) of the monomer having the lowest copolymerization reaction rate in the first composition ratio is preferably at least 1.1 times of the ratio of the contents (mol %) of the monomer having the lowest copolymerization reaction rate in the target composition.

The ratio of the contents (first composition ratio) of the monomers in the solution Sa is preferably determined in advance from the target composition ratio of the polymer (P) taking the reactivity of each monomer used in the polymerization into account.

More specifically, the first composition ratio of the solution Sa is preferably designed so that, when the ratio of the contents of the monomers existing in the reactor is the first composition ratio, the ratio of the contents of the composition units of a polymer molecule generated just after the solution Tb is added dropwise to the reactor is equal to the target composition ratio. In this case, the ratio of the contents of the monomer units of a copolymer molecule generated just after the solution Tb is added dropwise is equal to the ratio of the contents (target composition ratio) of the monomers in the solution Tb to be added dropwise, and therefore, the content ratio of the monomers left in the reactor just after the dropwise addition is always fixed (first composition ratio). Therefore, when the solution Tb is successively added dropwise to such a reactor, a stationary state under which a polymer molecule having the target composition ratio is successively produced is obtained.

There has been no information regarding a first composition ratio enabling such a stationary state prior to the present invention. This is a finding first obtained by the inventors of the present invention. A method of designing the first composition ratio will be described later.

The reactor may be charged with the solution Sa in advance. Also, the solution Sa may be gradually fed to the reactor by adding it dropwise or the like. Alternatively, these feed methods may be combined.

(Polymerization Initiator)

The polymerization initiator is added dropwise and fed to the reactor. The solution Tb may contain the polymerization initiator. For adding the solution Sa dropwise to the reactor, the solution Sa may contain the polymerization initiator. The polymerization initiator may be contained in the at least 2 solutions (Sa and/or Tb) to be added dropwise. A solution containing the polymerization initiator (polymerization initiator solution) may be added dropwise to the reactor separately from the solutions Sa and Tb. Alternatively, these solutions may be combined together.

The amount of the polymerization initiator to be used (the total amount in the main step) is designed on the basis of the type of polymerization initiator or according to the target value of the weight-average molecular weight of the polymer (P) to be obtained.

For example, when the polymer (P) in the present embodiment is a polymer for lithography, the amount of the polymerization initiator (the total amount to be fed in the main step) based on 100 mol % of the sum (the total amount to be fed in the main step) of the monomers fed to the reactor in the main step is preferably in a range from 1 to 25 mol % and more preferably in a range from 1.5 to 20 mol %.

(Content of Monomers in Solution Sa)

The total amount of monomers to be used in polymerization process (total feed amount of monomers) is the sum of the amount of the monomers contained in the solutions Sa, Tb, and Uc. The whole amount of the monomers to be fed is designed on the basis of the amount of the polymer (P) to be obtained.

When the ratio of the total amount of the monomers contained in the solution Sa in the total amount of the monomers is too small, the intended effect obtained by the use of the solution Sa is not sufficiently obtained. When the proportion is too large on the other hand, the molecular weight of the polymer produced in the early stage of the polymerization process becomes too large. Therefore, the total amount of the monomers contained in the solution Sa based on the total feed amount of monomers is preferably 3 to 40 mass % and more preferably 5 to 30 mass %.

(Feeding of Solutions Sa and Tb)

In the main step, it is necessary that the solution Sa exist in the reactor when the polymerization initiator is added dropwise to the reactor. Therefore, the feeding of the solution Sa to the reactor is started before the polymerization initiator is added dropwise to the reactor or simultaneously with the start of the dropwise addition of the polymerization initiator.

In addition, it is necessary that the solution Sa exist in the reactor when the solution Tb is added dropwise to the reactor. Therefore, the feeding of the solution Tb to the reactor is started after the feeding of the solution Sa to the reactor is started or simultaneously with the start of the feeding of the solution Sa. The dropwise addition of the solution Tb is preferably started simultaneously with the start of the dropwise addition of the polymerization initiator or after the start of the dropwise addition of the polymerization initiator.

The dropwise addition of the polymerization initiator and the dropwise addition of the solution Tb are preferably started simultaneously. The feeding of the solution Sa is completed before completion of the dropwise addition of the solution Tb.

The solution Tb may be added dropwise either continuously or intermittently and the solution Tb may be added dropwise at a varied rate. The solution may be preferably added dropwise continuously at a constant rate to stabilize the composition and molecular weight of the polymer to be produced.

When the solution Sa is fed by dropwise addition, it may be added dropwise either continuously or intermittently. Also, the solution Sa may be added dropwise at a varied rate. The solution may be preferably added dropwise continuously at a constant rate to stabilize the composition and molecular weight of the polymer to be produced.

The whole amount of the solution Sa is preferably fed in the early stage of the polymerization step. To describe in more detail, when the standard time is a time elapsed since the dropwise addition of the polymerization initiator is started until the dropwise addition of the solution Tb is completed, the feeding of the solution Sa is stopped before 20% of the above standard time is elapsed. When the standard time is, for example, 4 hours, the whole amount of the solution Sa is fed to the reactor before 48 minutes elapses after the start of the dropwise addition of the polymerization initiator.

The feeding of the solution Sa is completed before preferably 15% and more preferably 10% of the standard time elapses.

Also, the feeding of the whole amount of the solution Sa may be completed at 0% of the standard time. In other words, the reactor may be charged with the whole amount of the solution Sa before the start of the dropwise addition of the polymerization initiator.

(Feeding Rate of Polymerization Initiator)

The dropwise addition of the polymerization initiator in the main step can be either continued until, or completed before, the completion of the dropwise addition of the solution Tb. The dropwise addition of the polymerization initiator is preferably continued until the completion of the dropwise addition of the solution Tb.

The feeding rate of the polymerization initiator may be constant; however, by increasing the feeding amount thereof in the early stage of the polymerization process, generation of high-molecular-weight components (high polymer) in the early stage can be suppressed and, as a result, the variation in molecular weight in a polymer obtained after the polymerization process can be reduced. Such homogenization of molecular weight increases the solubility of the polymer for lithography in a resist solvent as well as in an alkali developing solution, leading to improvement of sensitivity of a resist composition.

The weight-average molecular weight of the polymer formed in the early stage of the polymerization step varies corresponding to the amount of the polymerization initiator to be fed during the early stage of the polymerization process. Therefore, the optimum amount of the polymerization initiator to be fed depends on the types of monomers, feed rate of the monomers, type of polymerization initiator and polymerization conditions. However, the optimum amount of the polymerization initiator is preferably set so that the weight-average molecular weight of the polymer formed particularly in the early stage of the polymerization step is close to the target value.

More specifically, it is preferable that, in the early stage before 5 to 20% of the above standard time has elapsed, 30 to 90% of the total feed amount of the polymerization initiator used in the main step is fed and thereafter the polymerization initiator is fed at a lower rate than in the early stage.

The early stage is preferably in a range from 5.5 to 17.5%, and more preferably 6 to 15%, of the standard time. The feed amount of the polymerization initiator is preferably 35 to 85 mass % and more preferably 40 to 80 mass % of the total feed amount of the polymerization initiator used in the main step.

Preferred Embodiment of the Main Step

Preferable modes of the main step include the following (a), (b) and (c).

(a) The reactor is charged with the entire amount of the solution Sa containing the monomers $\alpha_1$ to $\alpha_n$ in the first composition ratio in advance. Then, the solution in the reactor is heated to a predetermined polymerization temperature, and then, a polymerization initiator solution containing a part of the polymerization initiator to be fed in the main step and the solution Tb containing the monomers $\alpha_1$ to $\alpha_n$ in the second composition ratio and the rest of the polymerization initiator are respectively added in the reactor. The dropwise addition of the polymerization initiator solution and the dropwise addition of the solution Tb are started simultaneously or the dropwise addition of the polymerization initiator solution is started first. The dropwise addition of the polymerization initiator solution and the dropwise addition of the solution Tb are preferably started simultaneously. The time interval between the start of the dropwise addition of the polymerization initiator solution and the start of the dropwise addition of the solution Tb is preferably 0 to 10 minutes. The rates of dropwise additions of the solutions are each preferably fixed.

The dropwise addition of the polymerization initiator solution is completed before the dropwise addition of the solution Tb.

(b) The reactor is charged only with a solvent. Then, the solvent is heated to a predetermined polymerization temperature, and then, the solution Sa containing the monomers $\alpha_1$ to $\alpha_n$ in the first composition ratio and a part of the polymerization initiator and the solution Tb containing the monomers $\alpha_1$ to $\alpha_n$ in the second composition ratio and the rest of the polymerization initiator and the rest of the polymerization initiator are respectively added in the reactor. The dropwise additions of both solutions are started simultaneously or the dropwise addition of the solution Sa is started first. The time interval between the start of the dropwise addition of the solution Sa and the start of the dropwise addition of the solution Tb is preferably 0 to 10 minutes. The rates of dropwise additions of the solutions are each preferably fixed.

The dropwise addition of the solution Sa is completed before the dropwise addition of the solution Tb.

(c) The reactor is charged with a part of the solution Sa in advance. Then, the solution in the reactor is heated to a predetermined polymerization temperature, and then, a solution containing the rest of the solution Sa and a part of the polymerization initiator to be fed in the main step (hereinafter referred to as "the rest of solution Sa") and the solution Tb containing the monomers $\alpha_1$ to $\alpha_n$ in the second composition ratio and the rest of the polymerization initiator are respectively added in the reactor. The dropwise additions of the rest of solution Sa and the solution Tb are started simultaneously or the dropwise addition of the rest of solution Sa is started first. The dropwise addition of the polymerization initiator solution and the dropwise addition of the solution Tb are preferably started simultaneously. The time interval between the start of the dropwise addition of the rest of solution Sa and the start of the dropwise addition of the solution Tb is preferably 0 to 10 minutes. The rates of dropwise addition of the solutions are each preferably fixed.

The dropwise addition of the rest of solution Sa is completed before the dropwise addition of the solution Tb.

Method of Designing First Composition Ratio of Solution Sa

A preferred method of designing the first composition ratio will be described.

The composition ratio of monomers (ratio of contents of monomers) S'a is determined by the following methods (1) to (4).

When $\alpha'_1:\alpha'_2: \ldots :\alpha'_n$ is the content ratio (target composition ratio, unit: mol %) of the monomer units in the polymer (P) to be obtained, composition of S'a (unit: mol %) is represented by $\alpha_{11}:\alpha_{12}: \ldots :\alpha_{1n}$ and the factors obtained in the following procedures (1) to (3) are represented by $F_1$, $F_2 \ldots F_n$, wherein $\alpha_{11}=\alpha'_1/F_1$, $\alpha_{12}=\alpha'_2/F_2, \ldots \alpha_{1n}=\alpha'_n/F_n$.

The content ratio of each monomer in the first composition ratio of the solution Sa is preferably within a range of 0.8 to 1.2 times of respective values of the content ratios of the each monomer in S'a, more preferably within a range of 0.9 to 1.1 times, and even more preferable within a range of 0.95 to 1.05 times.

(1) First, a dropping solution containing 100 parts by mass of a monomer mixture having the same monomer composition ratio as the target composition ratio, $\alpha'_1:\alpha'_2: \ldots :\alpha'_n$, a polymerization initiator and a solvent is added dropwise to a reactor only containing a solvent at a fixed dropping rate. Then, the composition ratio (unit: mol %) $M_1:M_2: \ldots :M_n$, of the monomers $\alpha_1$ to $\alpha_n$ left in the reactor is determined at each of times $t_1$, $t_2$, $t_3$ . . . passed from the start of the dropwise addition. In addition, a ratio (mol %) of $P_1:P_2: \ldots :P_n$ of the constitutional units to $\alpha'_n$ in each of polymers which are produced between the time $t_1$ to the time $t_2$, between the time $t_2$ to the time $t_3$, . . . is calculated.

(2) a time zone from $t_m$ to $t_{m+1}$ (m denoting an integer of at least 1) in which the ratio $P_1:P_2: \ldots :P_n$ is closest to the target composition $\alpha'_1:\alpha'_2: \ldots :\alpha'_n$ is determined;

(3) factors $F_1$, $F_2 \ldots F_n$ are obtained from a value of $P_1:P_2: \ldots :P_n$ in the time zone from $t_m$ to $t_{m+1}$ and a value of $M_1:M_2: \ldots :M_n$ at the passage of time $t_m$, using the following equation $$F_1=P_1/M_1, F_2=P_2/M_2, \ldots F_n=P_n/M_n;$$

(4) composition of S'a (unit: mol %) is represented by $\alpha_{11}:\alpha_{12}: \ldots :\alpha_{1n}$, and the factors obtained in the above (3) are represented by $F_1$, $F_2 \ldots F_n$, wherein $\alpha_{11}=\alpha'_1/F_1$, $\alpha_{12}=\alpha'_2/F_2, \ldots \alpha_{1n}=\alpha'_n/F_n$.

More specifically, when, for example, the polymer (P) is a ternary polymer obtained by copolymerizing monomers x, y and z, and the target composition ratio is x':y':z', the composition ratio of S'a (mol %, the same hereinafter) $x_{00}:y_{00}:z_{00}$ are defined as values obtained by the equations $x_{00}=x'/Fx$, $y_{00}=y'/Fy$ and $z_{00}=z'/Fz$ by using the factors Fx, Fy and Fz calculated by the following method.

(Method of Calculating the Factors Fx, Fy and Fz)

The case where the polymer (P) is, for example, a ternary polymer will be described. However, the factors can be calculated in the same manner even in the case where the polymer (P) is a binary polymer or a quaternary or more multiple component polymer.

(1) First, dropping solution containing a monomer mixture having the same monomer composition ratio as the target composition ratio x':y':z', a solvent and a polymerization initiator is added dropwise at a constant dropping rate v in a reactor. The reactor is charged only with a solvent prior to the addition.

The composition ratio (unit: mol %), Mx:My:Mz, of the monomers x, y and z left in the reactor at each of times $t_1$, $t_2$, $t_3$ . . . from the start of the dropwise addition is determined. In addition, a ratio (mol %) of Px:Py:Pz of the monomer units in each of polymers produced between the time $t_1$ to the time $t_2$, between the time $t_2$ to the time $t_3$, is calculated.

(2) A time zone from $t_m$ to $t_{m+1}$ (m denoting an integer of at least 1) where the ratio Px:Py:Pz is the closest to the target composition ratio x':y':z' is determined.

(3) Factors Fx, Fy, and Fz are determined from the value of Px:Py:Pz between $t_m$ and $t_{m+1}$ and the value of Mx:My:Mz at the passage of time $t_m$ according to the equations Fx=Px/Mx, Fy=Py/My, Fz=Pz/Mz.

The factors Fx, Fy and Fz are respectively a value reflecting the relative reactivity of each monomer. Also, when the combination of the monomers or target composition ratio used in the polymerization is changed, the factors Fx, Fy and Fz are changed.

(4) The composition ratio of S'a (mol %) $x_{00}:y_{00}:z_{00}$ are values obtained by the equations $x_{00}=x'/Fx$, $y_{00}=y'/Fy$ and $z_{00}=z'/Fz$ by using the factors Fx, Fy and Fz.

In the present embodiment, in a case of designing the first composition ratio of the solution Sa using the abovementioned factors, the first composition ratio (mol %) is preferably within a range of ±20% of the composition ratio of S'a, more preferably within a range of ±10%, even more preferably within a range of ±5%, and most preferably identical to S'a (mol %) for obtaining the intended effect.

Later Step

In the later step, the solution Uc is added dropwise to the reactor after completion of the main step.

(Solution Uc)

The solution Uc is a collective designation of solutions U1, U2, . . . Uf (f denoting an integer of at least 1) used in the later step. As the solution Uc, only one solution (only U1) may be used, or at least two solutions (U1, U2 . . . Uf) may be used. The upper limit of f is not particularly limited; however, practically preferably no greater than 5, and more preferably no greater than 4, for avoiding complication of operation.

In a case of using at least 2 solutions as the solution Uc, the content ratio of monomers in the solution Uc (third composition ratio) means composition ratio of monomers in a total of U1 to Uf.

The composition ratios of monomers in the solutions U1 to Uf may be either the same or different from each other, and are different from the target composition. In the third composition, a proportion of a monomer having the lowest copolymerization reaction rate among the monomers $\alpha_1$ to $\alpha_n$ is smaller than in the target composition. The ratio of the contents (mol %) of the monomer having the lowest copolymerization reaction rate in the third composition ratio is preferably no greater than 0.9 times, and more preferably no greater than 0.7 times, of the ratio of the contents (mol %) of the monomer having the lowest copolymerization reaction rate in the target composition. The ratio of the contents of the monomer having the lowest copolymerization reaction rate in the third composition ratio may be zero.

A total amount of monomers contained in the solution Uc is 0.1 to 10 mass %, preferably 0.1 to 7.5 mass %, and more preferably 0.1 to 5 mass % of the total feed amount of monomers used in the polymerization step. The total amount of at least 0.1 mass % brings about a sufficient advantage of providing the later step.

The total amount of no greater than 10 mass %, 7.5 mass %, or 5 mass % brings about a sufficient effect of reducing variation in polymer composition.

Method of Designing Third Composition Ratio of Solution Uc

The composition ratio of monomers in the solution Uc (third composition ratio) is preferably a composition ratio designed based on a monomer composition ratio (content ratio of monomers) U'c obtained by the following procedures (5) to (8).

The composition ratio of U'c is obtained by the following procedure using the same factors ($F_1$ to $F_n$) as in the method of designing the first composition ratio, except for the smallest factor among them being substituted by 0.

Given a target composition (unit: mol %) indicating a content ratio of the monomer units $\alpha'_1$ to $\alpha'_n$ in the polymer (P) to be obtained being $\alpha'_1:\alpha'_2: \ldots :\alpha'_n$, composition ratio of U'c (unit: mol %) are represented by $\alpha_{31}:\alpha_{32}: \ldots :\alpha_{3n}$ and the factors obtained in the following procedures (5) to (7) are represented by $F_1, F_2 \ldots F_n$ (the smallest factor among $F_1$ to $F_n$ is substituted by 0), wherein $\alpha_{31}=\alpha'_1\times F_1/(\alpha'_1\times F_1+\alpha'_2\times F_2+ \ldots +\alpha'_n\times F_n)$, $\alpha_{32}=\alpha'_2\times F_2/(\alpha'_1\times F_1+\alpha'_2\times F_2+ \ldots +\alpha'_n\times F_n)$, . . . $\alpha_{3n}=\alpha'_n\times F_n/(\alpha'_1\times F_1+\alpha'_2\times F_2+ \ldots +\alpha'_n\times F_n)$.

The content ratio of each monomer in the third composition ratio of the solution Uc is preferably within a range of 0.8 to 1.2 times of respective values of the content ratios of the each monomer in U'c, more preferably within a range of 0.9 to 1.1 times, and even more preferable within a range of 0.95 to 1.05 times.

The composition ratio (mol %) of the monomer having the lowest copolymerization reaction rate in U'c is 0 (mol %). For obtaining the intended effect, the composition ratio (mol %) of the monomer having the lowest copolymerization reaction rate in the third composition ratio is preferably no greater than 10 mol %, more preferably no greater than 5 mol %, and most preferably zero.

The following procedures (5) to (7) are the same as procedures (1) to (3) in the method of designing the first composition ratio.

(5) First, a dropping solution containing 100 parts by mass of a monomer mixture having the same monomer composition ratio as the target composition ratio, $\alpha'_1:\alpha'_2: \ldots :\alpha'_n$, a polymerization initiator and a solvent is added dropwise to a reactor only containing a solvent at a fixed dropping rate. Then, the composition ratio (unit: mol %), $M_1:M_2: \ldots :M_n$, of the monomers $\alpha_1$ to $\alpha_n$ left in the reactor is determined at each of times $t_1, t_2, t_3 \ldots$ passed from the start of the dropwise addition. In addition, a ratio (mol %) of $P_1: P_2: \ldots :P_n$ of the constitutional units $\alpha'_1$ to $\alpha'_n$ in each of polymers which are produced between the time $t_1$ to the time $t_2$, between the time $t_2$ to the time $t_3$, . . . is calculated.

(6) a time zone from $t_m$ to $t_{m+1}$ (m denoting an integer of at least 1) in which the ratio $P_1:P_2: \ldots :P_n$ is closest to the target composition $\alpha'_1:\alpha'_2: \ldots :\alpha'_n$ is determined;

(7) factors $F_1, F_2 \ldots F_n$ are obtained from a value of $P_1: P_2: \ldots :P_n$ in the time zone from $t_m$ to $t_{m+1}$ and a value of $M_1:M_2: \ldots :M_n$ at the passage of time $t_m$, using the following equation $$F_1=P_1/M_1, F_2=P_2/M_2, \ldots F_n=P_n/M_n;$$

(8) compositions of U'c (unit: mol %) are represented by $\alpha_{31}:\alpha_{32}: \ldots :\alpha_{3n}$ and the factors obtained in the above (7) are represented by $F_1, F_2 \ldots F_n$ (the smallest factor among $F_1$ to $F_n$ is substituted by 0), wherein $\alpha_{31}=\alpha'_1\times F_1/(\alpha'_1\times F_1+\alpha'_2\times F_2+ \ldots +\alpha'_n\times F_n)$, $\alpha_{32}=\alpha'_2\times F_2/(\alpha'_1\times F_1+\alpha'_2\times F_2+ \ldots +\alpha'_n\times F_n)$, . . . $\alpha_{3n}=\alpha'_n\times F_n/(\alpha'_1\times F_1+\alpha'_2\times F_2+ \ldots +\alpha'_n\times F_n)$.

In the present embodiment, in a case of designing the third composition ratio of the solution Uc using the abovementioned factors, the third composition ratio (mol %) is preferably within a range of ±20% of the composition ratio of U'c, more preferably within a range of ±10%, even more preferably within a range of ±5%, and most preferably identical to U'c (mol %) for obtaining the intended effect.

However, the composition ratio (mol %) of the monomer having the lowest copolymerization reaction rate in the third composition ratio is preferably no greater than 10 mol %, more preferably no greater than 5 mol %, and most preferably zero.

The dropwise addition of the solution Uc is preferably started immediately after completion of the dropwise addition of the solution Tb.

In the dropwise addition of the solution Uc, U1 can be continuous, or U1, U2, Uf can be fed in sequence (intermittently). The dropping rate can be changed. At least two of U1, U2, Uf can be fed simultaneously. The feed rate of the monomers per unit time, fed to the reactor by the dropwise addition of the solution Uc (total amount of monomers in U1, U2, Uf) preferably decreases gradually or in a stepwise manner with the passage of time.

For example, a single type of solution (U1) with uniform monomer composition ratio and uniform monomer content (concentration) can be used as the solution Uc, and the dropping rate thereof can be decreased gradually or in a stepwise manner. Alternatively, at least two solutions (U1, U2, . . . Uf) with the same monomer composition ratio (with the above-defined allowable difference range) and different monomer contents (concentrations) can be used as the solution Uc. In this case, the feed rate of the monomers per unit time can be decreased gradually or in a stepwise manner by the sequential dropwise addition of at least two solutions such that the monomer concentration decreases, even with the constant dropping rate.

More specifically, given that: a period of time between the start and completion of dropwise addition of the solution Uc is defined as a later dropping time; a value obtained by dividing the total feed amount of monomers in the later step by the later dropping time is defined as an average feed rate; and a period of time between 0% to k % (k is 5 to 95) of the later dropping time is defined as a high-rate feed period in which the monomers are fed in a higher rate than the average feed rate, it is preferable that 50 to 95 mass % of the total feed amount of monomers in the later step is fed in the reactor during the high-rate feed period.

k is more preferably 20 to 80%, and even more preferably 30 to 70%. The amount of the monomers fed in the reactor during the high-rate feed period is more preferably 60 to 90 mass %, and even more preferably 70 to 85 mass %, of the total feed amount of the monomers in the later step.

In the later step, it is necessary that the polymerization initiator exists in the reactor when the solution Uc is added dropwise to the reactor. Therefore, also in the later step, it is preferable that the polymerization initiator is fed in the reactor.

The polymerization initiator can be contained in the solution Uc. Alternatively, a solution containing the polymerization initiator (polymerization initiator solution) may be added dropwise to the reactor separately from the solution Uc. Alternatively, these solutions may be combined together.

For example, when the polymer (P) in the present embodiment is a polymer for lithography, the amount of the polymerization initiator (the total amount to be fed in the later step) based on 100 mol % of the sum (the total amount to be fed in the later step) of the monomers fed to the reactor in the later step is preferably in a range from 1 to 25 mol % and more preferably in a range from 1.5 to 20 mol %.

After the later step, in other words after completion of the dropwise addition of the solution Uc, a maintaining step for maintaining the solution in the reactor at the polymerization temperature, a cooling step, a refining step and the like can take place appropriately.

According to the inventors' findings, in the dropping polymerization, only a monomer solution with the same monomer composition ratio as the target composition rate is simply continuously added in a reactor dropwise, the content ratio of the monomer units in a polymer formed is largely different from the target composition ratio immediately after the start of polymerization, and becomes closer to the target composition ratio with the passage of time; however, in the maintaining step after the dropwise addition of the monomer solution, a difference between the content ratio of the monomer units in the polymer formed and the target composition ratio becomes gradually greater. More specifically, a longer time period in the maintaining step substantially increases the composition ratio of the monomer units derived from the monomer with the lowest copolymerization reaction rate in the polymer formed. Given this, upon completion of the dropwise addition of the monomer solution, the monomer with the lowest copolymerization reaction rate is expected to remain in the reactor excessively in comparison to the target composition ratio.

In the present embodiment, the solutions Sa and Tb in which the content ratio of the monomers is designed so that the aforementioned stationary state can be obtained are used, ensuring that a copolymer molecule having almost the same composition ratio as the target composition ratio is produced immediately after the start of a polymerization reaction and such a state is maintained. Therefore, in the polymer formed in the main step, variation in the content ratio of the monomer units is reduced.

In addition, the maintaining step is not started right after the main step. By providing the later step for adding dropwise the solution Uc in which the proportion of the monomer with the lowest copolymerization reaction rate is smaller than in the target composition ratio, monomers other than the monomer with the lowest copolymerization reaction rate are fed into the reactor in a proportion greater than in the target composition ratio. It is preferable that the solution Uc does not contain the monomer with the lowest copolymerization reaction rate and only the monomers other than the monomer with the lowest copolymerization reaction rate are fed in the later step.

As a result, the monomer with the lowest copolymerization reaction rate remaining in the reactor excessively in comparison to the target composition ratio upon completion of the dropwise addition of the solution Tb can be efficiently consumed to form a polymer, thereby preventing widening of the difference between the content ratio of the monomer units in the polymer formed after the main step and the target composition over time. This can reduce the variation in the content ratio of the monomer units in the polymer (P) ultimately obtained.

In addition, making the monomer composition ratio of the solution Uc the composition ratio U'c obtained by the design procedure using the abovementioned factors, the content ratio of the monomer units in the polymer formed after the main step can be made closer to the target composition.

Furthermore, by decreasing the feed amount of the monomer (preferably only the monomers other than the monomer with the lowest copolymerization reaction rate), which is fed by the dropwise addition of the solution Uc, over time in the later step, shortage of the monomer with the lowest copolymerization reaction rate relative to the target composition ratio due to consumption in the reactor can be prevented. Therefore, the polymer with the monomer composition ratio close to the target composition ratio can be formed even with a small amount of monomers remaining in the reactor.

Given this, according to the present embodiment, variation in the content ratio of the monomer units in the polymer formed during a period from the start of the main step to the end of the later step can be suppressed, thereby reducing variation in the content ratio of the monomer units in the polymer (P) formed by the polymerization process.

Therefore, according to the present embodiment, the polymer (P) that has superior solubility in a solvent and can constitute a highly sensitive resist composition can be obtained with high reproducibility. It is to be noted that the polymer of the present embodiment may also be applied to use in applications other than resist applications.

In addition, according to the polymer of the present embodiment, a solubility-improving effect can be obtained. Furthermore, improvements in various performances can be expected.

Resist Composition

The resist composition of the embodiment of the present invention is prepared by dissolving the polymer for lithography of the present embodiment in a resist solvent. The resist solvent is, for example, the same one as the above polymerization solvent used in the production of the polymer.

When the resist composition of the present embodiment is a chemical amplification-type resist composition, it further contains a compound (hereinafter referred to as a photoacid generator) that generates an acid by irradiation with active rays or radial rays.

(Photoacid Generator)

As the photoacid generator, an appropriate one may be selected from known photoacid generators in chemical amplification type resist compositions. One type of photoacid generator may be used singly. Also, at least two photoacid generators may be used in combination.

Examples of the photoacid generator include onium salt compounds, sulfoneimide compounds, sulfone compounds, sulfonate compounds, quinonediazide compounds, and diazomethane compounds.

The content of the photoacid generator in the resist composition is preferably 0.1 to 20 mass parts and more preferably 0.5 to 10 mass parts, based on 100 parts by mass of the polymer.

(Nitrogen-Containing Compound)

The chemical amplification type resist composition may contain a nitrogen-containing compound. When the chemical amplification type resist composition contains a nitrogen-containing compound, further improvements in the shape of a resist pattern and post exposure stability can be attained. Namely, the sectional shape of a resist pattern becomes closer to a rectangular shape. Also, in a mass-production line of a semiconductor, there is the case where a resist film is allowed to stand for several hours after the resist film is irradiated with light and then baked (PEB). However, in this embodiment, deterioration in the sectional shape of a resist pattern caused by such a condition that the resist pattern is allowed to stand (deterioration with time) is more restrained.

The nitrogen-containing compound is preferably an amine, more preferably a secondary lower aliphatic amine, and a tertiary lower aliphatic amine.

The content of the nitrogen-containing compound in the resist composition is preferably 0.01 to 2 mass parts based on 100 mass parts of the polymer.

(Organic Carboxylic Acid and Oxoacid of Phosphorous or its Derivatives)

The chemical amplification type resist composition may contain an organic carboxylic acid and oxoacid of phosphorous or its derivatives (hereinafter these compounds are collectively called acid compounds). When the chemical amplification type resist composition contains an acid compound, deterioration in sensitivity caused by the formulation of a nitrogen-containing compound can be restrained. Also, further improvements in the shape of a resist pattern and post exposure stability can be attained.

Examples of the organic carboxylic acid include malonic acid, citric acid, malic acid, succinic acid, benzoic acid and salicylic acid.

Examples of oxoacid of phosphorous or its derivatives include phosphoric acid or its derivatives, phosphonic acid or its derivatives and phosphinic acid or its derivatives.

The content of the acid compound in the resist composition is preferably 0.01 to 5 mass parts based on 100 mass parts of the polymer.

(Additives)

The resist composition of the present embodiment may contain a surfactant and other additives such as a quencher, a sensitizer, a halation-preventive agent, a storage stabilizing agent, and an antifoaming agent if needed. All additives known in the present field may be used as the additives. Also, no particular limitation is imposed on the amount of these additives, and the amount of these additives may be optionally determined.

Method for Producing Substrate with Pattern Formed Thereon

An example of a method for producing a substrate with a pattern formed thereon according to the embodiment of the present invention will be described.

First, the resist composition of the present embodiment is applied by the spin coating method or the like to the surface of a substrate such as a silicon wafer on which a desired fine pattern is to be formed. Then, the substrate coated with the resist composition is dried by a baking treatment (prebaking) or the like to thereby form a resist film on the substrate.

Then, the resist film is exposed to light through a photomask to form a latent image. The exposure light is preferably light having a wavelength of 250 nm or less. The exposure light is preferably a KrF excimer laser, ArF excimer laser, $F_2$ excimer laser and EUV light and more preferably an ArF excimer laser. Electron irradiation can also be used.

Immersion exposure may be performed in which the resist film is irradiated with light in the condition that a liquid having a high refractive index is interposed between the resist film and the final lens of the exposure apparatus. The liquid having a high refractive index is, for example, pure water, perfluoro-2-butyltetrahydrofuran, and perfluorotrialkylamine.

After being exposed to light, the resist film is heat-treated (baked after being exposed, PEB). Then, an alkali developing solution is brought into contact with the resist film. Then, the exposed part is dissolved in the developing solution. Then, the developing solution is removed (developing). Examples of the alkali developing solution include known alkali developing solutions.

After the developing, the substrate is suitably rinse-treated. A resist pattern is formed on the substrate by this treatment.

The resist of the substrate on which the resist pattern is formed is reinforced by suitable heat treatment (post-baking). Then, the part on which no resist is formed is selectively etched.

After the etching, the resist is removed by a releasing agent to obtain the substrate on which a fine pattern is formed.

In particular, the polymer for lithography obtained by the embodiment of a method for producing a polymer for lithography (Z2') has excellent solubility in a solvent and enables the formation of a resist film having high sensitivity. Therefore, when the resist composition is prepared, the polymer can be dissolved easily and well in a resist solvent. Also, the resist composition has excellent solubility in an alkali developing solution. This contributes to an improvement in sensitivity. Also, because insoluble substances in the resist composition are small, defects caused by the insoluble substances are scarcely generated.

Therefore, by producing a substrate with a pattern formed thereon using the resist composition, a highly precise and fine resist pattern can be formed stably, while reducing defects on the substrate. Also, the resist composition of the present invention may be preferably used even in the case of forming a pattern by photolithography using exposure light having a wavelength of 250 nm or less or electron beam lithography, for example, lithography using an ArF excimer laser (193 nm) though it is required to use a resist composition having high sensitivity and high resolution in these kinds of lithography.

It is to be noted that when a resist composition is used in photolithography using exposure light having a wavelength of 250 nm or less, monomers suitably selected so that the polymer is transparent to the exposure light having such a wavelength are preferably used.

Method for Evaluating Copolymer (Estimation of Triad Fraction)

A method for evaluating the copolymer according to the embodiment of the present invention is described hereinafter with reference to the drawings.

FIG. 1 is a block diagram illustrating a configuration example of a copolymer evaluation apparatus that evaluates a copolymer by the method for evaluating a copolymer according to the present embodiment. In FIG. 1, the copolymer evaluation apparatus includes: a target variable analysis unit 11; a waveform processing unit 12; an explanatory variable analysis unit 13; a model generation unit 14; a sample analysis unit 15; a storage unit 16; a display unit 17; and a control unit 18.

The target variable analysis unit 11 calculates and outputs the triad fraction of each monomer unit in a polymer, which is a known sample, based on the copolymerization reactivity ratio of the monomer unit. The waveform processing unit 12 conducts the NMR measurement and performs Fourier transformation and data processing of an FID (Free Induction Decay) signal of the copolymer or polymer thus obtained.

The explanatory variable analysis unit 13 outputs an explanatory variable from the signal intensity for a chemical shift in the NMR measurements of the known sample and unknown sample.

The model generation unit 14 determines a regression equation (a regression equation of a regression model) of the target variable and the explanatory variable by partial least squares regression (PLS), and generating a sample model (a regression equation of a regression model and a regression model coefficient).

The sample analysis unit 15 uses the sample model to calculate a ratio of the triad of each monomer unit in an unknown sample, in other words an estimate of the triad fraction, from the chemical shift and signal intensity of the unknown sample.

The storage unit 16 stores data of calculation processes and evaluation examples, such as the explanatory variable, the sample model, and the triad fraction.

The control unit 18 displays the abovementioned calculation processes of each part, the triad fraction representing the ratio of triad as an evaluation result, and the like in a form of a result table on the display unit 17.

The control unit 18 also analyzes, or outputs to each part in the copolymer evaluation apparatus, data and control commands being input from a keyboard (not illustrated); or outputs data being input from an NMR device (not illustrated) to the waveform processing unit 12.

A copolymer evaluation operation by the method for evaluating copolymer according to the present embodiment performed by the copolymer evaluation apparatus of FIG. 1 is described hereinafter with reference to FIG. 1.

The target variable analysis unit 11 obtains the triad fraction as follows, as a target variable analysis process (I).

The target variable analysis unit 11 obtains a fraction of triad in the copolymer, i.e. triad fraction, by calculation. Here, the "triad" indicates three constitutional units successively bound in the polymer. The "triad of each monomer unit" indicates a structure in which three monomer units of the same type are successively bound. In a copolymer composed of n constitutional units, there are n types of triads of each monomer unit.

In a case in which there are two constitutional units A and B (n=2), a chain of three constitutional units can be in 6 combinations: AAA, AAB, BAB, ABA, BBA, and BBB. Among these, AAA and BBB are triads of each monomer unit (triads composed only of monomers). A fraction (%) of triad of each monomer unit can be obtained by the following equation (H).

[Formula 3]

$$P\{jjj\}(\%) = 100 \times [M'_j] \times P_{jj} \times P_{jj} \quad \text{(H)}$$

$$P_{jj} = \frac{[M_j]}{\sum_{h=1}^{n} \frac{[M_h]}{r_{jh}}}$$

In the above equation, $[M'_j]$ denotes a molar fraction of a monomer unit j in a copolymer; $P_{jj}$ denotes probability of reaction with the monomer (unit) j, j denotes a monomer unit of a growing end of the copolymer; $[M_j]$ and $[M_h]$ denote molar fractions of monomer units j, h in a reaction system; and $r_{jh}$ denotes a copolymerization reactivity ratio of a reaction from the monomer (unit) j to the monomer (unit) h.

In a case in which formation of a copolymer follows the first-order Markovian statistics, the triad fraction of each monomer unit obtained by the above equation (H) can be obtained from a calculation using the copolymerization reactivity ratio and a composition ratio of a copolymer of no greater than 10% in polymerization rate.

The target variable analysis unit 11 writes to the storage unit 16, for each molar fraction of each monomer unit: a combination of molar fractions of monomer unit; and a triad fraction obtained by the above equation (H) from the combination of molar fraction of monomer unit, as a molar fraction-triad fraction table in which the combinations of molar fractions respectively correspond to the triad fractions.

The waveform processing unit 12 then performs Fourier transformation and data processing of an FID (Free Induction Decay) signal of the copolymer or polymer obtained by the NMR measurement.

In other words, the waveform processing unit 12 performs Fourier transformation of the FID signal obtained by the NMR measurement, and generates an NMR spectrum signal including information of chemical shift (frequency component) and signal intensity (spectrum intensity of the NMR spectrum). Here, by setting a BF (broadening factor) according to a type of the target nucleus to be measured (the broadening factor corresponding to each target nucleus is set in advance by measurement by experiment), spectral resolution of the corresponding target nucleus can be improved. This allows improvement of estimation precision of the composition ratio including chain information of monomers in copolymers and polymers.

A device used for the NMR measurement can be a commercially available product and not particularly limited; however, an NMR device having magnetic field intensity of at least 7 Tesla (300 MHz as frequency of $^1H$ nucleus) which provides high chemical-shift resolution is preferably used.

The target nucleus in the NMR measurement can be selected according to a type of the copolymer (P); however, $^1H$, $^{13}C$, $^{19}F$, and $^{29}Si$ are preferable for high natural abundance ratio and high sensitivity.

A diameter of a sample tube used in the NMR measurement can be selected according to a type of the copolymer (P); however, in a case of using $^1H$ or $^{19}F$ as the target nucleus, the diameter is preferably at least 3 mmφ and more preferably at least 5 mmφ for high natural abundance ratio.

On the other hand, in a case of using $^{13}C$ or $^{29}Si$ as the target nucleus, the diameter is preferably at least 5 mm$\phi$ and more preferably at least 10 mm$\phi$ for obtaining higher sensitivity and higher signal intensity.

The sample concentration of copolymer or polymer used in the NMR measurement is not particularly limited; however, the sample concentration is preferably at least 1 mass %, more preferably at least 5 mass %, and even more preferably at least 10 mass % for obtaining higher sensitivity and higher signal intensity.

The sample concentration is preferably no greater than 50 mol %, more preferably no greater than 30 mol %, and even more preferably no greater than 20 mol % or less from the viewpoint of suppressing influence of relaxation time by viscosity of a sample solution.

The deuterated solvent used in the NMR measurement is not particularly limited as long as the solvent can dissolve the copolymer and polymer. Examples of the deuterated solvent include: deuterated chloroform ($CDCl_3$), deuterated dimethylsulfoxide (DMSO-$d_6$), heavy water ($D_2O$), deuterated methanol ($CH_3OD$ or $CD_3OD$), deuterated tetrahydrofuran ($C_4D_4O$), and deuterated hexafluoroisopropanol (HFIP-$d_2$). As a reference material of the chemical shift, tetramethylsilane (TMS) and $CFCl_3$ may be added.

The temperature of the sample in the NMR measurement is not particularly limited as long as the temperature is no greater than the boiling point of the sample solvent and does not cause decomposition and alteration of copolymer and polymer; however, the temperature is preferably as high as possible for obtaining higher sensitivity and higher signal intensity.

The number of scans in the NMR measurement is not particularly limited and can be appropriately selected according to a type of the target nucleus to be measured; however, in a case of using $^1H$ or $^{19}F$ as the target nucleus, the number of scans is preferable at least 4 and more preferably at least 16 for high natural abundance ratio. On the other hand, in a case of using $^{13}C$ or $^{29}Si$ as the target nucleus, the number of scans is preferably at least 1500 and more preferably at least 3000 for higher sensitivity and higher signal intensity. Here, the "scans" in the NMR measurement indicates that the NMR signal is acquired for multiple times and the plurality of signals are overlaid (or, accumulated or added) and the signal thus overlaid is used as an FID signal of an ultimate observation result of the sample.

Subsequently, the explanatory variable analysis unit 13 generates the chemical shift and signal intensity for each sample as described below, as an explanatory variable analysis process (II).

The explanatory variable analysis unit 13 outputs quantitative usage information G (matrix described later) of the NMR spectrum signal composed of the chemical shift and the signal intensity by: phase focusing of the NMR spectrum signal composed of the Fourier-transformed chemical shift and a waveform thereof (correction process to symmetrize each NMR spectrum signal); baseline processing (correcting the baseline of the NMR spectrum signal to be parallel to frequency axis); peak integration (intensity area in a preset integral range (obtained by dividing the range of the chemical shift, described later) in the chemical shift) and setting of a chemical shift value as standard (normalization). The range of the chemical shift used here is a range including target nuclei of the constitutional units composing the copolymer.

In other words, in splitting and integration of the NMR spectrum, a split interval for integration of a spectrum (signal intensity) of the Fourier-transformed chemical shift is important.

In other words, the explanatory variable analysis unit 13, regarding a k-th sample (k being an integer of 1 to m) among m types of copolymer or composite polymer samples, splits the chemical shift into p (p being an integer) at a regular interval, thereby obtaining $f_{kg}$, which is an integral value of a g-th range thus split.

In addition, the explanatory variable analysis unit 13 performs the normalization process, with 100 being the total of the integral values of the spectrum thus split.

This gives $$f_{k1}+f_{k2}+\ldots f_{kg}+\ldots +f_{kp}=100$$

Next, an average $f_{g\text{-}ave}$ of the g-th integral values from all the m types of samples is obtained by the following equation.

$$f_{g\text{-}ave}=(f_{1g}+f_{2g}+\ldots f_{kg}+\ldots +f_{mg})/m$$

After obtaining averages for all the p split spectra, regarding the integral value for the i-th sample, a standardized integral value $b_{kg}$ is obtained by subtracting the average $f_{g\text{-}ave}$ of the split ranges of the corresponding chemical shift, for each integral of spectrum being normalized by a frequency range of the NMR spectrum. This gives the following equation.

$$b_{kg}=f_{kg}-f_{g\text{-}ave}$$

As a result, the spectrum intensity of the k-th sample is represented by the following vector.

$$x_k=(b_{k1},b_{k2},\ldots,b_{kg},\ldots,b_{kp})$$

Thereafter, the explanatory variable analysis unit 13 collects the spectrum intensities for all the m-types of samples, and then generates the quantitative usage information G as a matrix represented by the following formula (11). The quantitative usage information G is a chemical shift and signal intensity (after integration) that is a basis for generating an explanatory variable.

[Formula 4]

$$G = \begin{bmatrix} b_{11} & \cdots & b_{1p} \\ \vdots & \ddots & \vdots \\ b_{m1} & \cdots & b_{mp} \end{bmatrix} \quad (11)$$

In addition, the explanatory variable analysis unit 13: adds sample identification information that is unique to each sample; makes the sample identification information corresponding to the chemical shift and the signal intensity of the sample identified thereby; and stores the information as a sample table to the storage unit 16.

Next, the model generation unit 14 generates a model of an explanatory variable as described below, as a model generation process (III).

The model generation unit 14 has a definition of a modeling equation for the explanatory variable, in other words a regression equation of a regression model, being set as $G=TP+R_G$.

In this modeling equation, T is a score for the explanatory variable; P is a loading for the explanatory variable; and $R_G$ is a residual matrix. Here, the loading is a direction coordinate of an axis that captures the dispersion of factors (values of the sample) the most.

The model generation unit 14 has a definition of a modeling equation for the target variable, in other words a regression equation of a regression model, being set as $C=UQ+R_C$.

In this equation, C is a numerical data of the triad fraction (predicted value) of each monomer unit that is a matrix represented by the following formula (12). In this matrix, $c_1 \ldots c_n$ are vectors representing values of triad fraction for each monomer unit.

[Formula 5]

$$C=[c_1 c_2 \ldots c_n] \quad (12)$$

In addition, U is a score for the target variable; Q is a loading for the target variable; and $R_C$ is a residual matrix.

The model generation unit 14 defines the matrix G as the following equation, based on a result of the NMR measurement of the known sample, of which triad fraction of each monomer unit is known, with the matrix G of the NMR spectrum of the NMR measurement result and the vector $c_1$ which is a collection of triad fraction of a first monomer unit of each known sample through a first weight vector $w_1$.

$$G=c_1 w_1 + R \quad (i)$$

The residual matrix R is eliminated from the above equation (i); a transposed matrix $c_1^T$ and an inverse matrix $(c_1^T c_1)^{-1}$ of $c_1$ are multiplied from left to right; and a compromise solution for the first weight vector $w_1$ is calculated by the following equation.

$$w_1=(c_1^T c_1)^{-1} c_1^T G \quad (ii)$$

The model generation unit 14 then obtains a first explanatory variable score $t_1$ from the NMR spectrum G and the first weight vector $w_1$, using the following equation.

$$G w_1^T (w_1 w_1^T)^{-1/2} = t_1 \quad (iii)$$

Based on the first explanatory variable score $t_1$ thus obtained, a first target variable loading $q_1$ is obtained by the following equation.

$$c_1 = t_1 q_1 + R' \quad (iv)$$

The residual matrix R' is eliminated (deleted) from the above equation; a transposed matrix $t_1^T$ and an inverse matrix $(t_1^T t_1)^{-1}$ of the first explanatory variable score $t_1$ are multiplied from left to right; and a compromise solution for the first target variable loading $q_1$ is calculated by the following equation.

$$q_1 = (t_1^T t_1)^{-1} t_1^T c_1 \quad (v)$$

The model generation unit 14 then uses a defining equation $C=UQ+R_C$ to obtain a relationship between the composition vector $c_1$ and the first target variable loading $q_1$ through the first target variable score $u_1$, as the following equation.

$$c_1 = u_1 q_1 + R'' \quad (vi)$$

The model generation unit 14 eliminates (deletes) the residual matrix R''; multiplies a transposed matrix $q_1^T$ and an inverse matrix $(q_1 q_1^T)^{-1}$ of the first target variable loading $q_1$ from right to left; and obtains a compromise solution for the first target variable score $u_1$ by the following equation.

$$u_1 = c_1 q_1^T (q_1 q_1^T)^{-1} \quad (vii)$$

The first target variable score $u_1$ is then obtained from the first explanatory variable score $t_1$ through an internal correlation coefficient $s_1$ as in the following equation.

$$u_1 = s_1 t_1 \quad (viii)$$

If sufficient correlation cannot be obtained by $u_1$ thus calculated, $u_1$ is assigned to $c_1$ in the equation (i), and calculations by the equations (i) to (viii) are repeated until $u_1$ converges to a certain value. When $u_1$ immediately after the repeated calculation is within a range of 0.99 to 1.01 times of $u_1$ immediately before the repeated calculation, the model generation unit 14 considers that $u_1$ is converged and terminates the calculation.

When converged $u_1$ is obtained, $s_1$, $t_1$, $q_1$, and $w_1$ are also obtained.

The model generation unit 14 obtains an equation $G=t_1 p_1 + R'''$ from the defining equation $G=TP+R_G$; eliminates (deletes) the residual matrix R''' from the equation; multiplies a transposed matrix $t_1^T$ and an inverse matrix $(t_1^T t_1)^{-1}$ of $t_1$ from left to right; and obtains a compromise solution for $p_1$ by the following equation.

$$p_1 = (t_1^T t_1)^{-1} t_1^T G \quad (ix)$$

Next, using $u_1$, $q_1$, $s_1$, $t_1$, and $p_1$ obtained by the above equations, the matrices $G_2$ and $C_2$ corresponding to the residual matrices $R_G$ and $R_C$ of the modeling equation are expressed as following equations.

$$G_2 = G - t_1 p_1 \quad (x)$$

$$C_2 = C - u_1 q_1 = C - s_1 t_1 q_1 \quad (xi)$$

Based on the equation (i), the model generation unit 14 then obtains the matrix $G_2$ as in the following equation, using a vector $c_2$ which is a collection of triad fractions of a second monomer and a second weight vector $w_2$.

$$G_2 = c_2 w_2 + R_2 \quad (i')$$

Subsequently, $u_2$, $s_2$, $t_2$, $q_2$, $w_2$, and $p_2$ are obtained as in the equations (ii) to (ix).

Similarly, the model generation unit 14 obtains $u_3$ to $u_n$, $s_3$ to $s_n$, $t_3$ to $t_n$, $q_3$ to $q_n$, $w_3$ to $w_n$, and $p_3$ to $p_n$.

For example, matrices $G_n$ and $C_n$ corresponding to the residual matrices $R_G$ and $R_C$ of the modeling equation are represented as the following equations.

$$G_n = G - t_{n-1} p_{n-1} \quad (xii)$$

$$C_n = C - u_{n-1} q_{n-1} = C - s_{n-1} t_{n-1} q_{n-1} \quad (xiii)$$

Based on the equation (i), the model generation unit 14 then obtains the matrix $G_n$ as in the following equation, using a vector $c_n$ which is a collection of triad fractions of a n-th monomer and a n-th weight vector $w_n$.

$$G_n = c_n w_n + R_n \quad (i'')$$

Subsequently, $u_n$, $s_n$, $t_n$, $q_n$, $w_n$, and $p_n$, are obtained as in the equations (ii) to (ix).

Next, the model generation unit 14 writes and stores vectors thus obtained $u_1$ to $u_n$, $s_1$ to $s_n$, $t_1$ to $t_n$, $q_1$ to $q_n$, $w_1$ to $w_n$, and $p_1$ to $p_n$, which are sample data (coefficient of the regression model, in other words a vector of coefficient of the regression equation) for each known sample, as sample data of the known sample to the storage unit 16.

Next, as described below, the sample analysis unit 15 calculates a triad fraction (triad fraction estimate) of the unknown sample based on the sample data generated by the model generation unit 14, as the sample analysis process (IV).

The waveform processing unit 12 performs Fourier transformation and data processing of an FID signal of the copolymer or polymer obtained by the NMR measurement. As in the processing already described for the known sample, this processing by the waveform processing unit 12 generates an NMR spectrum signal of the unknown sample.

As in the processing of the NMR spectrum signal performed by the explanatory variable analysis unit 13, the sample analysis unit 15 performs: the phase focusing of the NMR spectrum signal composed of the Fourier-transformed chemical shift and a waveform thereof; the baseline processing; the peak integration; and the setting of the chemical shift value (normalization) used as a standard. The range of the chemical shift used here is a range including target nuclei of the constitutional units composing the copolymer.

The sample analysis unit 15 then outputs quantitative usage information A of the NMR spectrum signal composed of the chemical shift and the signal intensity, in a form of a matrix shown in the following formula (13). The quantitative usage information A is for a case in which the number of unknown samples is 3 (m=3); however, the same processing applies to a single unknown sample and multiple unknown samples.

[Formula 6]

$$A = \begin{bmatrix} b_{11} & \cdots & b_{1p} \\ b_{21} & \cdots & b_{2p} \\ b_{31} & \cdots & b_{3p} \end{bmatrix} \quad (13)$$

Next, the sample analysis unit 15 reads the weight vectors $w_1$ to $w_n$ from the sample data stored in the storage unit 16 and obtains the explanatory variable (NMR spectrum) scores $t_{A1}$ to $t_{An}$ from the following equations.

$$A_{w1}^T (w_1 w_1^T)^{-1/2} = t_{A1} \cdots$$

$$A_{wn}^T (w_n w_n^T)^{-1/2} = t_{An}$$

In addition, the sample analysis unit 15 reads the internal correlation coefficients $s_1$ to $s_n$, which have been obtained by the model generation unit 14, stored in the storage unit 16 and obtains the target variable (triad fraction of each monomer unit) scores (vectors) $u_{A1}$ to $u_A$, from the following equations.

$$u_{A1} = s_1 t_{A1}$$

$$u_{An} = s_n t_{An}$$

Thereafter, the sample analysis unit 15 uses the vectors $q_1$ to $q_n$, which have been obtained by the model generation unit 14, stored in the storage unit 16 to calculate the triad fractions (vectors) $c_{A1}$ to $c_{An}$ of each monomer unit of the unknown samples based on $u_{A1}$ to $u_{An}$ obtained as described above, and outputs as estimate of triad fractions. The triad fractions (vectors) $c_{A1}$ to $c_{An}$ show estimates of triad fractions of respective n monomer units in each of three unknown samples (triad fraction estimates).

$$c_{A1} = u_{A1} q_1$$

$$c_{An} = u_{An} q_n$$

The control unit 18 displays the triad fraction estimates respectively for the n monomer units of each unknown sample as a result table, on the display unit 17.

According to the copolymer evaluation method of the present embodiment, since no unnecessary heat is applied to the sample, highly precise estimation of a triad fraction (triad fraction estimate) of each monomer unit constituting the copolymer in the composition of the copolymer is made possible.

In general, since solvents used for a composition for semiconductor lithography poorly dissolve a homopolymer, a polymer chain in which the same constitutional units are bound is expected to deteriorate solubility to solvents.

In fact, as shown later in Examples, if the triad fraction of monomer units of the same type contained in a copolymer chain is small, solubility of the copolymer to a solvent is improved and sensitivity of a resist composition containing the copolymer to irradiated light is improved.

To describe more in detail with regard to sensitivity, if the triad fraction of monomer units of the same type contained in a copolymer chain is small, even if the monomer units are in the same ratio, the monomer (constitutional) units are assumed to be distributed uniformly in the copolymer chain. Given this, a resist composition produced by using a copolymer with a small triad fraction of monomer units of the same type is expected to have high sensitivity to irradiated light.

For the above-described reason, the method for evaluation copolymer according to the embodiment of the present invention can simply evaluate randomness of monomer constituting the copolymer in a chain structure, and can evaluate photosensitivity of a resist composition produced using the copolymer by obtaining the triad fraction of the monomer units of the same type in the copolymer formed from monomers, without actually producing the resist composition.

It should be noted that the triad fraction of each monomer unit contained in a copolymer chain can be controlled by polymerization conditions.

Generally, the amount of each monomer to be used in the synthesis of a copolymer is determined on the basis of the target value of an intended monomer composition ratio. Also, a polymerization condition and the like are so designed that the average monomer composition ratio in a synthesized copolymer becomes close to the target monomer composition ratio.

However, because the copolymerization reactivity ratios of monomers to be copolymerized differ from each other in many cases, the monomers are not copolymerized at random. This causes difference in monomer (constitutional) composition ratio of a copolymer obtained and bias in the copolymer chain. Also, according to the finding of the inventors of the present invention, the monomer composition ratio of a produced copolymer also differs corresponding to a difference in reaction time (polymerization rate). Particularly, the monomer composition ratios of copolymers produced in the early and later stages tend to differ largely from the target value and the copolymer tends to include a large number of polymer chains in which the constitutional units of the same type are successively bound.

Hence, as described in Examples below, in the early stage or in the initial and later stages of the polymerization reaction, by controlling so that the variation in monomer composition ratios in a copolymer to be formed is reduced by using the above-described polymerization methods (Z1) or (Z2), preferably a partial dropping method, the estimate of the triad fraction of monomer unit is reduced, solubility of the copolymer to a solvent is improved, and sensitivity of a resist composition containing the copolymer is improved compared to a case of not performing such control.

It is more preferable to use the embodiment of the method for producing a copolymer for lithography (Z2') to control so that the variation in monomer composition ratios in a copolymer to be formed is reduced, in the initial and later stages of the polymerization reaction.

More specifically, a copolymer for lithography in which the total of the triad fractions (triad fraction estimates) calculated by the method for evaluating copolymer if the present embodiment is not more than 20 mole % in the copolymer is preferable. The total of the triad fractions is more preferably no greater than 15 mol %, even more preferably no greater than 13 mol %.

The copolymer for lithography having the total of the triad fractions within the above-specified ranges has excellent solubility in a solvent and enables the formation of a resist film having high sensitivity.

Therefore, when the resist composition is prepared, the polymer can be dissolved easily and well in a resist solvent. Also, the resist composition has excellent solubility in an alkali developing solution. This contributes to an improvement in sensitivity. Also, because insoluble substances in the resist composition are small, defects caused by the insoluble substances are scarcely generated.

Therefore, by producing a substrate with a pattern formed thereon using the resist composition, a highly precise and fine resist pattern can be formed stably, while reducing defects on the substrate. Also, the resist composition of the present invention may be preferably used even in the case of forming a pattern by photolithography using exposure light having a wavelength of 250 nm or less or electron beam lithography, for example, lithography using an ArF excimer laser (193 nm) though it is required to use a resist composition having high sensitivity and high resolution in these kinds of lithography.

It is to be noted that when a resist composition is used in photolithography using exposure light having a wavelength of 250 nm or less, monomers suitably selected so that the polymer is transparent to the exposure light having such a wavelength are preferably used.

Method for Analyzing Copolymer Composition (Estimation of Randomness of Chain Structure)

Figure 2:
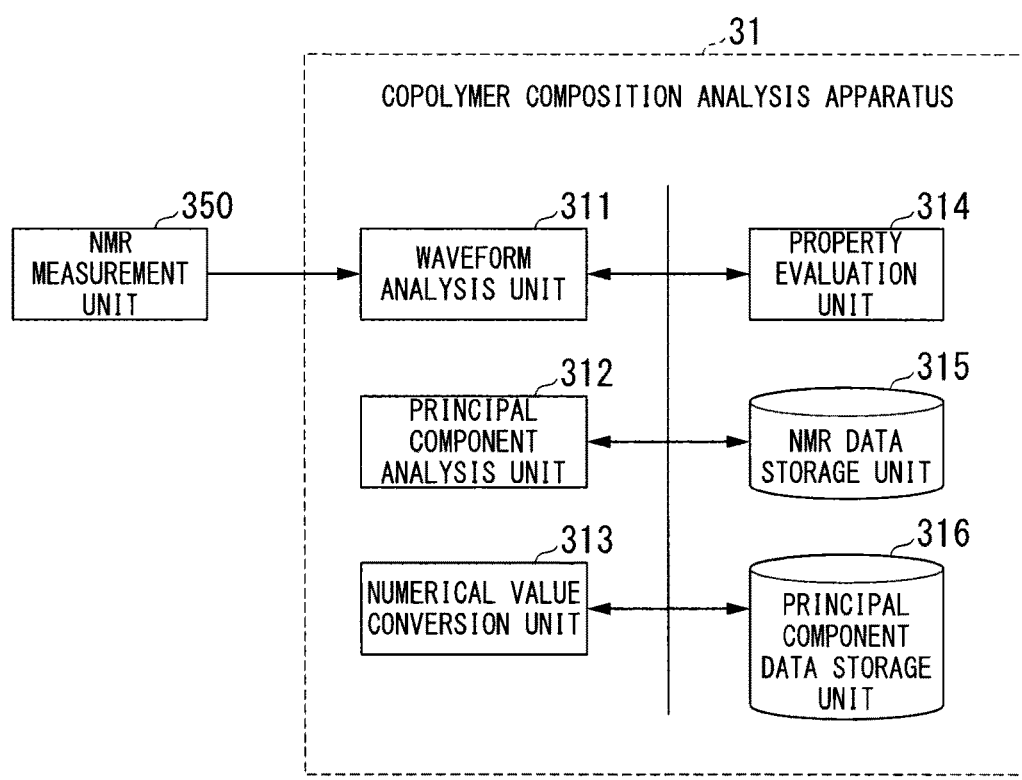
FIG. 2 is a block diagram illustrating a configuration example of a copolymer composition analysis apparatus according to an embodiment of the present invention.

FIG. 2 is a schematic block diagram illustrating a configuration example of a copolymer composition analysis apparatus that performs analysis of an alignment state of monomer units in the copolymer by the method for analyzing copolymer composition according to an embodiment of the present invention.

The copolymer composition analysis apparatus includes the following program to be executed by a computer used in the method for analyzing copolymer composition in terms of an alignment state of monomer units in the copolymer. A program makes a computer to execute: a measurement data extraction process in which a measurement data extraction unit extracts the NMR spectrum of a range including wavelengths of the monomers constituting the copolymer from the NMR spectrum of the copolymer as copolymer measurement data; a process of principal component analysis in which a principal component analysis unit performs a principal component analysis with respect to the chemical shift and spectral intensity between the copolymer measurement data and monomer measurement data of the NMR spectra of the monomers, with regard to first to n-th principal components corresponding to the number n of the monomers (n denoting an integer of at least 2); a process of distance calculation in which, in a principal component space of n-th dimension composed of principal component axes of the first principal component to the n-th principal component, a numerical value conversion unit obtains an evaluation distance between a comparison space of (n−1)-th dimension including all the coordinate points corresponding to principal component scores of the monomers on the principal component axes and a target coordinate point corresponding to a principal component score of the copolymer; and a property evaluation process in which a property evaluation unit evaluates properties of the copolymer based on the evaluation distance.

More specifically, the copolymer composition analysis apparatus 31 includes: a waveform processing unit 311; a principal component analysis unit 312; a numerical value conversion unit 313; a property evaluation unit 314; an NMR data storage unit 315; and a principal component data storage unit 316.

The waveform processing unit 311 performs Fourier transformation and data processing of an FID (Free Induction Decay) signal of the copolymer or polymer obtained by an NMR measurement unit 350, for each sample, assigns sample identification information to the NMR spectrum data composed of the amount of chemical shift (frequency component) and the spectrum intensity for each amount of chemical shift, and stores the NMR spectrum data along with the sample identification information to the NMR data storage unit 315.

In the NMR data storage unit 315, the NMR spectrum data, which is composed of the amount of chemical shift and the spectrum intensity for each amount of chemical shift of a homopolymer constituted only of each monomer constituting a copolymer or polymer to be evaluated, is stored in advance along with respective monomer identification information. Alternatively, similarly to the copolymer to be evaluated, the waveform processing unit 311 can generate the NMR spectrum data from the NMR spectrum of the homopolymer measured by the NMR measurement unit 350 and store the NMR spectrum data along with respective monomer identification information.

The principal component analysis unit 312 performs principal component analysis of a plurality of samples stored in the NMR data storage unit 315, and writes principal component score of each sample to the principal component data storage unit 316, for each sample identification information and for each monomer identification information.

Here, upon the principal component analysis, the principal component analysis unit 312 selects the number of principal component axes, in other words the number of principal components, corresponding to the number of types of monomers used for forming the copolymer and polymer, from the principal components thus obtained in an order of contribution. In other words, the number of principal components to be selected from the principal components obtained as a result of the principal component analysis is the same as the number of types of monomers constituting the copolymer to be analyzed. The number of dimensions of a principal component space (described later) is also the same as the number of types of monomers.

For example, in analysis of alignment of each monomer in a composition (chain structure) of a copolymer formed of three types of monomers, the principal component analysis unit 312 selects three principal components in a descending order of contribution as a result of the principal component analysis.

In the principal component space composed of principal component axes of the principal components, the numerical value conversion unit 313 obtains a distance from a point representing the principal component score on each principal component axis of the copolymer to be evaluated, i.e. a coordinate point of the copolymer to be evaluated in the principal component space, to a space including coordinate points of samples of all homopolymers composed only of single-type monomers as an evaluation distance. As used herein, the principal component space indicates a space composed of principal component axes orthogonal to each other, corresponding to n principal components (2 s n) selected from the principal components obtained by the principal component analysis. The coordinate points in the principal component space are points of coordinate in n-th dimension space represented by coordinate values on n principal component axes, the coordinate value being the principal component scores on principal component axes.

Figure 3:
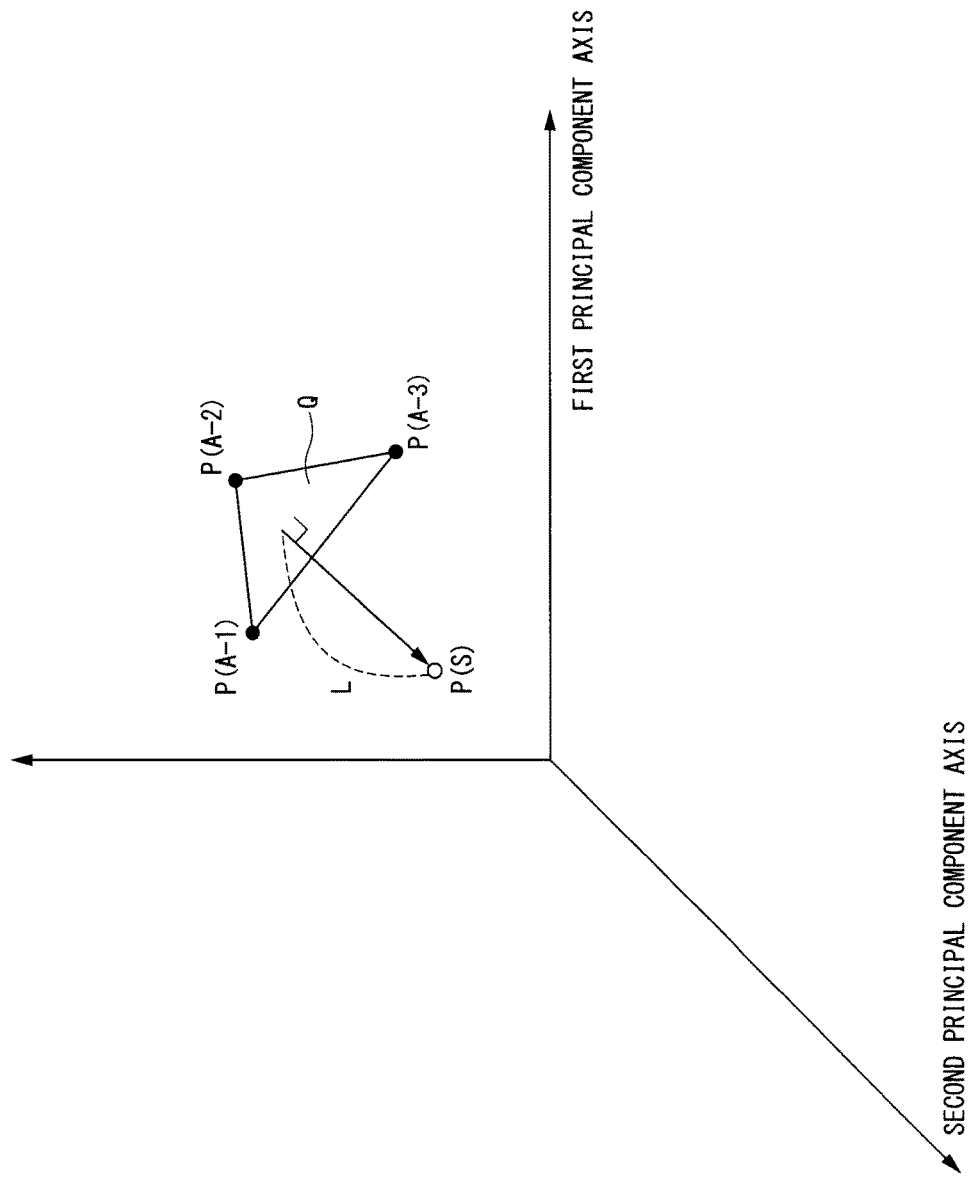
FIG. 3 is a diagram illustrating coordinate points of samples in a three-dimensional principal component space, indicating a result of a principal component analysis performed on a copolymer formed by polymerizing three monomers.

For example, FIG. 3 is a diagram illustrating coordinate points of samples in a three-dimensional principal component space, indicating a result of a principal component analysis performed on a copolymer formed by polymerizing three monomers.

In a case in which three types of monomers are used and the number of principal components is three, the principal component space is three-dimensional; and in this three-dimensional space, three coordinate points of the three types of monomer compose a two-dimensional plane (two-dimensional space) Q as a comparison space. In other words, the two-dimensional space Q is formed as a comparison space from three coordinate points P (A-1), P (A-2), and P (A-3) for all the three types of monomers, the space including the three coordinate points.

In addition, the numerical value conversion unit 313 calculates an evaluation distance L (S) between a coordinate point P(S) in the three-dimensional space of the copolymer to be analyzed and the two-dimensional comparison space Q formed of the coordinate points of the monomers. The calculation of the evaluation distance L (S) by the numerical value conversion unit 313 is described later in detail.

The property evaluation unit 314 determines randomness of alignment of each monomer in the chain structure of the composition of the copolymer, based on the evaluation distance L (S) between the comparison space Q including all the coordinate points of homopolymer and the coordinate point of the copolymer to be evaluated; evaluates lithography characteristics of a composition containing the copolymer to be evaluated from a result of determination; and displays a result on a display window (not illustrated).

The method for evaluating copolymer (method for analyzing copolymer composition) using the copolymer composition analysis apparatus of the present embodiment includes the following processes.

(1) a measurement process of dissolving the copolymer for lithography in a solvent and performing the NMR measurement of the copolymer (performed by the NMR measurement unit 350);
(2) a waveform processing process of performing Fourier transformation and data processing of an FID signal of the copolymer obtained by the measurement process (1) (performed by the waveform processing unit 311);
(3) a principal component analysis process of performing the principal component analysis of the quantitative usage information of the NMR spectrum data output from the waveform processing process (2) to each sample, and calculating the principal component scores for the selected principal components of each sample (performed by the principal component analysis unit 312);
(4) a numerical value conversion process of, in the principal component space composed of principal component axes of which number corresponds to the number of types of monomers, i.e. with the number of dimension being the number of types of monomers, expressing principal component scores for the principal components output from the above process (3) as coordinate values, which are positions on different orthogonal coordinate axes (principal component axes), and expressing the coordinate points, which is positions of the samples in the principal component space, as coordinate values (principal component scores) on the coordinate axes (principal component axes), thereby calculating an evaluation distance between the comparison space passing through all the coordinate points representing the principal component scores of homopolymers and coordinate points of the samples (performed by the numerical value conversion unit 313);
(5) a property evaluation process of evaluating the lithography characteristics of a composition containing the copolymer for lithography, based on the evaluation distance between the comparison space passing through all the coordinate points representing the principal component scores of homopolymers and points of the samples calculated by the above processes (1) to (4) (performed by the property evaluation unit 314).

In the present embodiment, it is preferable that the property evaluation unit 314 evaluates the length in which the monomers of the same type are arranged successively, based on the evaluation distance, in the composition of the copolymer.

In addition, it is preferable that the property evaluation unit has a threshold for determining the evaluation distance and evaluates the characteristics of the composition prepared by using the copolymer, by comparison between the evaluation distance and the threshold.

In a case in which the copolymer is the copolymer for resist, the property evaluation unit can evaluate the lithography characteristics including solubility to a solvent and sensitivity to exposure, by comparing the evaluation distance with the threshold.

A device as the NMR measurement unit 350 used for the NMR measurement can be a commercially available product and not particularly limited; however, an NMR device having magnetic field intensity of at least 7 Tesla (300 MHz as frequency of $^1$H nucleus) which provides high chemical-shift resolution is preferably used.

The target nucleus in the NMR measurement can be selected according to a type of the copolymer (p); however, $^1$H, $^{13}$C, $^{19}$F, and $^{29}$Si are preferable for high natural abundance ratio and high sensitivity.

A diameter of a sample tube used in the NMR measurement can be selected according to a type of the copolymer (p); however, in a case of using $^1$H or $^{19}$F as the target nucleus, the diameter is preferably at least 3 mmϕ and more preferably at least 5 mmϕ for high natural abundance ratio. On the other hand, in a case of using $^{13}$C or $^{29}$Si as the target nucleus, the diameter is preferably at least 5 mmϕ and more preferably at least 10 mmϕ for higher sensitivity and higher signal intensity.

The sample concentration of copolymer in the deuterated solvent used in the NMR measurement is not particularly limited; however, the sample concentration is preferably at least 1 mass %, more preferably at least 5 mass %, and even more preferably at least 10 mass % for obtaining higher sensitivity and higher signal intensity.

The sample concentration is preferably no greater than 50 mol %, more preferably no greater than 30 mol %, and even more preferably no greater than 20 mol % or less from the viewpoint of suppressing influence of relaxation time by viscosity of a sample solution.

The deuterated solvent used in the NMR measurement is not particularly limited as long as the solvent can dissolve the copolymer. Examples of the deuterated solvent include:

deuterated chloroform ($CDCl_3$), deuterated dimethylsulfoxide (DMSO-$d_6$), heavy water ($D_2O$), deuterated methanol ($CH_3OD$ or $CD_3OD$), and deuterated hexafluoroisopropanol (HFIP-$d_2$). As a reference material of the chemical shift, tetramethylsilane (TMS) and $CFCl_3$ may be added.

The temperature of the sample in the NMR measurement is not particularly limited as long as the temperature is no greater than the boiling point of the sample solvent and does not cause decomposition and alteration of copolymer; however, the temperature is preferably as high as possible for obtaining higher sensitivity and higher signal intensity. The number of scans in the NMR measurement is not particularly limited and can be appropriately selected according to a type of the target nucleus to be measured; however, in a case of using $^1H$ or $^{19}F$ as the target nucleus, the number of scans is preferable at least 4 and more preferably at least 16 for high natural abundance ratio. On the other hand, in a case of using $^{13}C$ or $^{29}Si$ as the target nucleus, the number of scans is preferably at least 1500 and more preferably at least 3000 for higher sensitivity and higher signal intensity. Here, the "scans" in the NMR measurement indicates that the NMR signal is acquired for multiple times and the plurality of signals are overlaid (or, accumulated or added) and the signal thus overlaid is used as an FID signal of an ultimate observation result of the sample.

As described above, in the waveform processing process, the waveform processing unit 311 performs Fourier transformation of the FID signal obtained by the NMR measurement, and generates NMR spectrum data including information of chemical shift (frequency component) and signal intensity (spectrum intensity).

Here, by setting a BF (broadening factor) according to a type of the target nucleus to be measured (the broadening factor corresponding to each target nucleus is set in advance by measurement by experiment), spectral resolution of the corresponding target nucleus can be improved. This allows improvement of measurement precision.

The waveform processing unit 311 outputs quantitative usage information G (matrix) of the NMR spectrum data, the information being composed of frequency ranges obtained by dividing the chemical shift by a predetermined range and values obtained by integrating the signal intensity to each frequency range, by: phase focusing of the NMR spectrum signal composed of the Fourier-transformed chemical shift and a waveform thereof (correction process to symmetrize each NMR spectrum signal); baseline processing (correcting the baseline of the NMR spectrum signal to be parallel to frequency axis); and setting of a chemical shift value as standard. Here, the range of the chemical shift used for generating the NMR spectrum signal is a range including target nuclei of the constitutional units composing the copolymer. In other words, the waveform processing unit 311 extracts NMR spectra of only the frequency ranges including the wavelength of the target nucleus in all monomers composing the copolymer to be evaluated, from the NMR spectra input from the NMR measurement unit 350, thereby generating the NMR spectrum signal.

In the waveform processing process by the waveform processing unit 311, in splitting and integration of the NMR spectrum of the present embodiment, a split interval for integration of spectrum intensity of the Fourier-transformed chemical shift is important.

In other words, the waveform processing unit 311 sequentially reads pieces of the NMR data for the m types of copolymer and homopolymer samples from the NMR data storage unit 315 based on the sample identification information or the monomer identification information, and obtains, as the NMR spectrum data for each sample of copolymer and monopolymer, data including an integral value of spectrum intensity for each frequency range of the chemical shift.

For example, the waveform processing unit 311, regarding a k-th sample (k being an integer of 1 to m) among m types of copolymer or homopolymer samples, splits the chemical shift (frequency range) into p (p being an integer) at a regular interval, thereby obtaining $f_{kg}$, which is a integral value of a g-th range thus split.

The waveform processing unit 311 thus performs a process for generating the NMR spectrum data for each copolymer and homopolymer sample from the NMR spectrum of the m types of copolymer and homopolymer samples. Here, the homopolymer is a polymer composed of a single type of monomer among monomers composing the copolymer to be evaluated. Given this, in a case in which the copolymer to be evaluated is composed of n types of copolymer, there is n types of homopolymer in a relationship of m>n.

In addition, for each sample of copolymer and homopolymer, the waveform processing unit 311 adds all the integral values of the spectrum intensity (signal intensity) in all the frequency ranges obtained by dividing the chemical shift. With 100 being the total of the values, the integral value in each frequency range is normalized as shown in the following equation.

$$f_{k1}+f_{k2}+\ldots f_{kg}+\ldots +f_{kp}=100$$

Next, the waveform processing unit 311 adds the normalized integral values of g-th frequency range of all the m types of sample, divides the result of the addition by m (the number of types), and obtains an average $f_{g\text{-}ave}$ from the following equation as an average of integral values of g-th frequency ranges of all the m types.

$$f_{g\text{-}ave}=(f_{1g}+f_{2g}+\ldots f_{kg}+\ldots +f_{mg})/m$$

After obtaining the above-described averages for all the m types for all the p frequency ranges (split spectra), regarding the integral value for the gi-th sample, the waveform processing unit 311 subtracts $f_{g\text{-}ave}$, which is an average of the frequency ranges i.e. the split ranges of the corresponding chemical shift from the integral value $f_{kg}$ of the normalized spectrum intensity, thereby obtaining a standardized integral value $b_{kg}$ by the following equation.

$$b_{kg}=f_{kg}-f_{g\text{-}ave}$$

Then, the waveform processing unit 311 obtains the NMR spectrum data represented by the following vector, from the spectrum intensity of each split range of the frequency measured for the k-th sample.

$$x_k=(b_{k1},b_{k2},\ldots ,b_{kg},\ldots ,b_{kp})$$

Thereafter, the waveform processing unit 311 collects the spectrum intensities for all the m types of samples, and expresses as a matrix G in (31) below. The matrix G (m by p) shown in (31) is a chemical shift and signal intensity (after integral) that is a basis for generating an explanatory variable. As described later, a principal component analysis is performed on the matrix G and a matrix T of explanatory variables is generated.

[Formula 7]

$$G = \begin{bmatrix} b_{11} & \cdots & b_{1p} \\ \vdots & \ddots & \vdots \\ b_{m1} & \cdots & b_{mp} \end{bmatrix} \quad (31)$$

Provided the matrix G from the waveform processing unit 311, the principal component analysis unit 312 generates a transposed matrix $G^T$ (p by m) from the matrix G.

The principal component analysis unit 312 then multiplies the matrix G by the transposed matrix $G^T$ from left to right, thereby obtaining an SSCP matrix $G^T G$.

Thereafter, the principal component analysis unit 312 obtains an eigenvector V of the SSCP matrix $G^T G$ thus obtained by the following relational equation.

$$G^T G V = \Delta^2 V$$

The eigenvector V thus obtained is expressed by (32) below and the eigenvalue $\Delta^2$ (i.e. $\lambda$) is expressed by (33) below.

[Formula 8]

$$V = \begin{bmatrix} a_{11} & \cdots & a_{1p} \\ \vdots & \vdots & \vdots \\ a_{p1} & \cdots & a_{pp} \end{bmatrix} \quad (32)$$

[Formula 9]

$$\Delta^2 = \begin{bmatrix} \lambda_1 \\ \vdots \\ \lambda_p \end{bmatrix} \quad (33)$$

In addition, V in (32) has the following relationship.

$$\{(a_{11})^2 + (a_{21})^2 + \ldots + (a_{p1})^2\}^{1/2} = \{(a_{12})^2 + (a_{22})^2 + \ldots + (a_{p2})^2\}^{1/2} = \ldots = \{(a_{1p})^2 + (a_{2p})^2 + \ldots + (a_{pp})^2\}^{1/2} = 1$$

In $\Delta^2$ of (33), $\lambda_1, \lambda_2, \ldots, \lambda_p$ are eigenvalues of the SSCP matrix $G^T G$ and in a relationship $\lambda_1 > \lambda_2 > \ldots > \lambda_p$.

For example, in order to obtain an eigenvalue $\lambda_1$ from the relational equation $G^T G V = \Delta^2 V$, $\lambda$ is solved using the theorem for obtaining an eigenvalue shown in the following equation to obtain up to p solutions. The largest $\lambda$ obtained is $\lambda_1$.

$$\det(G^T G - \lambda I) = 0$$

Note that $\det(G^T G - \lambda I)$ is a determinant of $(G^T G - \lambda I)$, wherein I is an identity matrix of p by p.

Here, the eigenvalue $\lambda_2$ is the second largest among the solutions $\lambda$, and solutions $\lambda$ can be similarly obtained up to $\lambda_p$.

The principal component analysis unit 312 assigns the eigenvalues $\lambda_1, \lambda_2, \ldots, \lambda_p$ to $\lambda$ in the relational equation $G^T G V = \lambda V$, to thereby solve the equation and obtain the eigenvector V.

And then, the principal component analysis unit 312 multiplies the matrix G (matrix of collection of spectrum intensities for all the n types of samples) by the eigenvector V thus obtained, thereby obtaining a matrix T representing principal component scores.

$$GV = T$$

The matrix T has m rows and up to p columns, as shown in (34) below.

[Formula 10]

$$T = \begin{bmatrix} b_{11}a_{11} + b_{12}a_{12} + \cdots + b_{1p}a_{1p} & \cdots & b_{11}a_{1p} + b_{12}a_{2p} + \cdots + b_{1p}a_{pp} \\ \vdots & \ddots & \vdots \\ b_{m1}a_{11} + b_{m2}a_{12} + \cdots + b_{mp}a_{1p} & \cdots & b_{m1}a_{1p} + b_{m2}a_{2p} + \cdots + b_{mp}a_{pp} \end{bmatrix} \quad (34)$$

The first column of the matrix T shows the principal component scores for a first principal component PC1, the second column shows the principal component scores for a second principal component PC2 in m types of samples. The principal component scores can similarly be obtained for up to a principal component PCn. For example, the first principal component score $t_{k1}$ for the k-th sample is represented by the following equation.

$$t_{k1} = b_{k1}a_{11} + b_{k2}a_{12} + \ldots + b_{kp}a_{1p}$$

The principal component analysis unit 312 writes and stores the principal component score obtained for each sample, along with the sample identification information or the monomer identification information, to the principal component data storage unit 316.

Processing in the numerical value conversion process is described in detail below. In the following description, for the sake of convenience, a case using two types of monomers as constitutional units (n=2) is exemplified; however, the number of types of monomer is not limited to n=2 and the number of constitutional units n indicating the number of types of monomer is not particularly limited.

Figure 4:
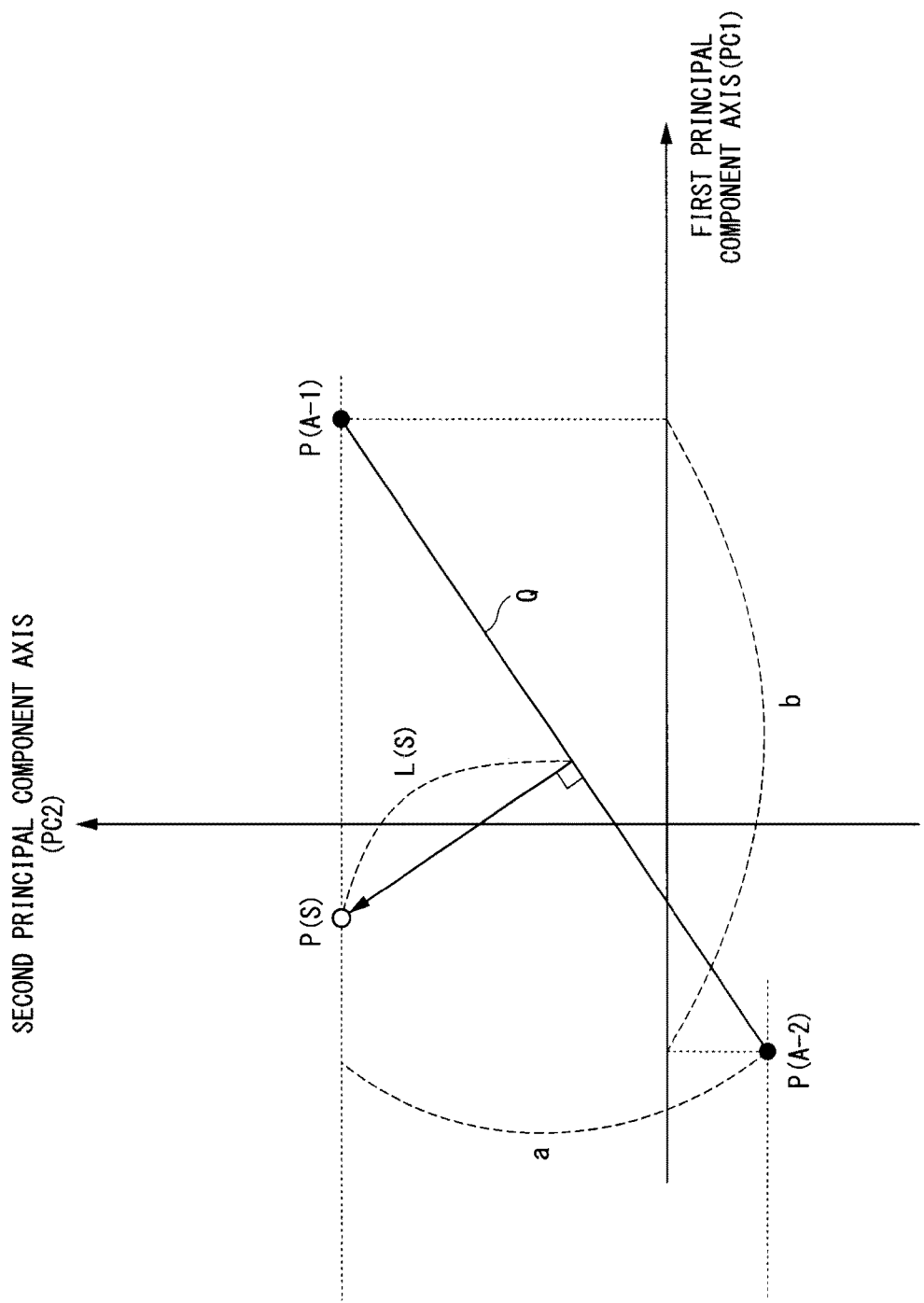
FIG. 4 is a diagram illustrating a two-dimensional principal component space composed of a first principal component axis (PC1) and a second principal component axis (PC2), in which the abscissa axis is the first principal component axis and the ordinate axis is the second principal component axis.

FIG. 4 is a diagram illustrating a two-dimensional principal component space in which the abscissa axis is the first principal component axis (PC1) and the ordinate axis is the second principal component axis (PC2). In other words, a two-dimensional space is shown that is a principal component space composed of the principal component axis PC1 and the principal component axis PC2 being orthogonal to each other.

The coordinate values of the homopolymer composed of a monomer A-1 and a monomer A-2 compose a one-dimensional space (line segment) as the comparison space Q including the coordinate values thereof, that is one dimension smaller than the principal component space, which is two-dimensional.

Here, the numerical value conversion unit 313 reads the principal component score for the first principal component axis PC1 and the principal component score for the second principal component axis PC2 of: the copolymer S composed of two constitutional units; and the samples A-1 and A-2 composed of single constitutional units, from the principal component data storage unit 316 based on the sample identification information and the monomer identification information. The numerical value conversion unit 313 then uses the principal component scores of the principal component axes as coordinate values, to define coordinate points in the principal component space as follows. Similarly, the coordinate point of the sample S of the copolymer S to be evaluated as follows.

$$P(A\text{-}1)=(PC1(A\text{-}1),PC2(A\text{-}1))$$

$$P(A\text{-}2)=(PC1(A\text{-}2),PC2(A\text{-}2))$$

$$P(S)=(PC1(S),PC2(S))$$

Since the samples A-1 and A-2 are homopolymers, single constitutional units are consecutively bound in the composition of polymer. In other words, the samples A-1 and A-2 are composed of the same type of monomers consecutively bound without other type of monomer. In the one-dimensional space passing through both coordinate points P(A-1) and P(A-2) (line segment as the comparison space Q), in other words in a line segment (straight line) connecting the coordinate points P(A-1) and P(A-2), the single-type monomers are consecutively bound as arrangement of constitutional units. Therefore the one-dimensional space is a line segment with the highest consecutiveness of arrangement of monomers. The evaluation distance L (S) from the line segment shows randomness of arrangement of monomers in a chain structure in the copolymer.

For example, the numerical value conversion unit 313 obtains numerical values a, b, and c by the following equations.

$$a=PC2(A\text{-}2)-PC2(A\text{-}1)$$

$$b=PC1(A\text{-}1)-PC1(A\text{-}2)$$

$$c=-PC1(A\text{-}1)\times(PC2(A\text{-}2)-PC2(A\text{-}1))-PC2(A\text{-}1)\times(PC1(A\text{-}1)-PC1(A\text{-}2))$$

The numerical value a indicates a difference of the second principal component score between the sample A-1 and the sample A-2 on the second principal component axis PC2. The numerical value b indicates a difference of the first principal component score between the sample A-1 and the sample A-2 on the first principal component axis PC1. The numerical value c indicates a value obtained by adding a negative value of a result of multiplication of the numerical value a by the first principal component score of the sample A-1 to a negative value of a result of multiplication of the numerical value b by the second principal component score of the sample A-1.

Then, the numerical value conversion unit 313 obtains an evaluation distance L (S) between the straight line (one-dimensional space) of the comparison space Q passing through all of the coordinate points P (A-1) and P (A-2) of the samples A-1 and A-2 and the coordinate point P (SPC1, SPC2) of the sample S to be evaluated, by the following equation. Here, SPC1 is the first principal component score and SPC2 is the second principal component score of the sample S.

$$L=|a\times SPC1+b\times SPC2+c|/(a^2+b^2)^{1/2}$$

The numerical value conversion unit 313 thus calculates the evaluation distance L (S). A larger evaluation distance L (S) between the point representing the polymer sample S to be evaluated and the straight line passing through all of the points P(A-1) and P(A-2) of the homopolymer samples A-1 and A-2 indicates higher randomness of the copolymer chain.

In other words, in the present embodiment, the principal components indicates randomness of the alignment of monomers in the copolymer. As a result, the evaluation distance L (S) allows qualitative evaluation of a length of successive alignment of the single-type monomers (the number of the single-type monomers successively arranged) in the chain structure of the copolymer.

The evaluation distance from a space including coordinate points of homopolymers can be used as a standard for qualitatively evaluating a difference of composition between a blocked state in which single-type monomers are arranged adjacently and a random state in which multi-type monomers are arranged adjacently.

Given this, the property evaluation unit 314 determines that, if the evaluation distance L (S) between the copolymer sample to be evaluated and the space composed of homopolymers is greater, the randomness of alignment, in which different monomers are arranged adjacently in the copolymer chain, is higher.

For example, the property evaluation unit 314 can be configured to have a distance threshold being set experimentally and to output an NG signal indicating inappropriateness for resist use when the evaluation distance L (S) calculated by the numerical value conversion unit 313 is smaller than the distance threshold and an OK signal indicating appropriateness for resist use when the evaluation distance L (S) is greater than the distance threshold L (S).

Alternatively, the property evaluation unit 314 can be configured to have numerical values of lithography characteristics, composed of solubility and photosensitivity, being set experimentally for respective evaluation distances L (S), and to output the numerical value of lithography characteristics in a case of producing a composition for resist using the copolymer for resist, in response to the evaluation distance L (S) being obtained.

As described in Modification below, in a resist composition produced using the copolymer for resist with high randomness, solubility to a solvent upon development is effectively improved. Also, the photosensitivity of the resist composition containing the copolymer upon lithography is improved.

The reason of obtaining such a solubility-improving effect and a photosensitivity-improving effect is as follows.

Generally, the amount of each monomer to be used in the synthesis of a copolymer is determined on the basis of the target value of an intended monomer composition ratio. Also, a polymerization condition and the like are so designed that the average monomer composition ratio in a synthesized copolymer becomes close to the target monomer composition ratio.

However, because the copolymerization reactivity ratios of monomers to be copolymerized differ from each other in many cases, the monomers are not copolymerized at random. This causes difference in monomer composition ratio of a copolymer obtained and bias in the copolymer chain due to blocks of single-type monomers in monomer arrangement in the copolymer chain.

Also, according to the finding of the inventors of the present invention, the monomer composition ratio of a produced copolymer also differs according to a difference in reaction time (polymerization rate). Particularly, the monomer composition ratios of copolymers produced in the early and later stages tend to differ largely from the target value and the copolymer tends to include a large number of polymer chains in which the constitutional units of the same type are successively bound.

On the other hand, since solvents used for a composition for semiconductor lithography poorly dissolve a homopolymer, a polymer chain in which the same constitutional units are bound is expected to deteriorate solubility to solvents.

In addition, in a case in which the randomness of the chain structure is high, the constitutional units are expected to be distributed more evenly within each copolymer chain. As a result, superior lithography characteristics can be expected in a composition for resist produced by using the copolymer for resist.

For the reasons described above, the method for evaluating copolymer in the present embodiment can evaluate the characteristics of a composition for resist containing copolymer for resist without actually producing the composition for resist, by simply evaluating the randomness of the copolymer for resist.

More specifically, the present embodiment provides a method that can evaluate the lithography characteristics of a composition for resist containing a copolymer for resist by simply estimating the randomness of a chain structure of the copolymer, without actually producing the composition for resist and without actually undergoing a lithography process, while strictly evaluating resolution by light upon exposure and uniformity of solubility to a solvent upon development of a resist. Given this, the present embodiment can easily evaluate the randomness of arrangement of monomers in a chain structure of a copolymer such as a copolymer for lithography, and, by obtaining a correlation between the randomness and characteristics of a composition using the copolymer in advance, can evaluate a composition to be produced without actually producing the composition by using the copolymer and then evaluating the characteristics of the composition actually produced.

In addition, since the present embodiment performs evaluation by using the NMR spectrum obtained by the NMR measurement, upon estimation of quantitative determination or chain distribution of the monomers in the polymer, measurement deviation due to: a difference in pyrolisys efficiency of sample depending on the temperature of heat processing; or a difficulty in quantitatively obtaining pyrolysis products that reflect the constitutional units, is not caused, unlike in the conventional arts.

In addition, a large number of samples is therefore not necessary for correction processing and the like, allowing a simple evaluation of a composition.

EXAMPLES

The present invention will be described in more detail by way of examples, which are however not intended to limit the present invention. In the following examples, all designations of parts indicate parts by weight, unless otherwise noted.

Measurement and evaluation of molecular weight (weight average molecular weight) of samples, average monomer composition ratio in a copolymer and the like were conducted as follows.

(Measurement of Weight Average Molecular Weight)

The weight-average molecular weight (Mw) and distribution of molecular weight (Mw/Mn) of the copolymer was determined as a value based on polystyrene by GPC (Gel Permeation Chromatography) under the following GPC conditions.

(GPC Condition)

Apparatus: Tosoh High-Performance GPC apparatus (trade name: HLC-8220GPC), manufactured by Tosoh Co., Ltd.;

Separation column: column prepared by connecting three columns (trade name: Shodex GPC K-805 L, manufactured by Showa Denko K.K.) in series;

Measuring temperature: 40° C.;

Eluent: THF

Sample (in the case of a copolymer): solution obtained by dissolving about 20 mg of a copolymer in 5 mL of THF and by filtering the solution by a 0.5 µm membrane filter;

Sample (in the case of a polymerization reaction solution): solution obtained by dissolving about 30 mg of a polymerization reaction solution in 5 mL of THF and by filtering the solution by a 0.5 µm membrane filter Flow rate: 1 mL/min;

Injection amount: 0.1 mL

Detector: Differential reflectometer.

Calibration curve I: about 20 mg of standard polystyrene was dissolved in 5 mL of THF. Then, the mixture solution was filtered through a 0.5 µm membrane filter to obtain a solution, which was then poured into a separation column in the above condition. Then, the relationship between elution time and molecular weight was determined. The following standard polyethylene (all products are represented by trade names) was used as the standard polyethylene manufactured by Tosoh Co., Ltd.

F-80 (Mw=706,000);
F-20 (Mw=190,000);
F-4 (Mw=37,900);
F-1 (Mw=10,200);
A-2500 (Mw=2,630),
A-500 (mixture of products: Mw=682, 578, 474, 370 and 260)

(Measurement of Average Monomer Composition Ratio of Copolymer)

About 5 parts by mass of the copolymer was dissolved in about 95 parts by mass of deuterated dimethyl sulfoxide to obtain a sample solution. This sample solution was placed in a NMR tube. Then, the sample solution was analyzed using $^1$H-NMR (manufactured by JEOL Ltd., resonance frequency: 270 MHz). The average monomer composition ratio of the copolymer was calculated from the integral intensity ratio of signals derived from each constitutional unit.

(Quantitative Measurement of Monomer)

The amount of a monomer left in a polymerization reaction solution was determined by the following methods.

First, 0.5 g of the polymerization reaction solution in the reactor was sampled. Then, the sample solution was diluted to a total volume of 50 ml with acetonitrile using a measuring flask. This diluted solution was filtered through a 0.2 µm membrane filter. Then, the amount of an unreacted monomer in the diluted solution was determined for every type of monomer by using a high-performance liquid chromatograph (trade name: HPLC-8020, manufactured by Tosoh Co., Ltd.).

The measurement was made under the following conditions. Specifically, one separation column (trade name: Inertsil ODS-2, manufactured by GL Sciences Inc.) was used as the separation column. A water/acetonitrile gradient type was used as the mobile phase. The flow rate was designed to be 0.8 mL/min. As the detector, an ultraviolet-visible absorptiometer (trade name: UV-8020, manufactured by Tosoh Co., Ltd.) was used. The detection wavelength was designed to be 220 nm. The measuring temperature was designed to be 40° C. The pouring amount was designed to be 4 µL. Also, Inertsil ODS-2 (trade name, particle diameter of silica gel: 5 µm and column inside diameter 4.6 mm×column length 450 mm) was used as the separation column. Also, the gradient condition of the mobile phase was designed to be as follows. The solution A is water. The solution B is acetonitrile. In order to quantitatively measure the amount of an unreacted monomer, three types of each monomer solution differing in concentration were used as standard solutions.

Measuring time 0 to 3 min: solution A/solution B=90 vol %/10 vol %.

Measuring time 3 to 24 min: solution A/solution B=90 vol %/10 vol % to 50 vol %/50 vol %.

Measuring time 24 to 36.5 min: solution A/solution B=50 vol %/50 vol % to 0 vol %/100 vol %.

Measuring time 36.5 to 44 min: solution A/solution B=0 vol %/100 vol %.

(Evaluation of the Solubility of the Copolymer)

Any one of the following methods (1) and (2) was conducted.

(1) 20 parts of the copolymer and 80 parts of PGMEA (Propylene Glycol Monomethyl Ether Acetate) were blended with each other. Then, the time taken to completely dissolve the copolymer was measured while stirring the mixture at 25° C. It was visually determined whether the copolymer was completely dissolved or not.

(2) 20 parts of the copolymer and 80 parts of PGMEA were blended with each other. Then, the time taken to completely dissolve the copolymer was measured while stirring the mixture at 25° C. After visually determining complete dissolution, heptane was added until the cloud point was reached and the amount of heptane being added was measured. Reaching of the cloud point was visually determined.

(Evaluation of the Sensitivity of the Resist Composition)

The resist composition was applied to a 6-inch silicon wafer with rotation. Then, the wafer was prebaked (PAB) at 120° C. on a hot plate for 60 seconds to form a resist film 300 nm in thickness. Using an ArF excimer laser exposure apparatus (trade name: VUVES-4500, manufactured by Litho Tech Japan Corporation), 18 shots having an area of 10 mm×10 mm were exposed to light at varied doses. Then, the resist film was post-baked (PEB) at 110° C. for 60 seconds. After that, using a resist developing analyzer (trade name: RDA-806, manufactured by Litho Tech Japan Corporation), the resist film was developed at 23.5° C. by an aqueous 2.38% tetramethylammonium solution for 65 seconds. The resist film exposed at each dose was measured to detect a variation in resist film thickness with time during developing.

The relationship between the logarithm of the exposure dose (unit: $mJ/cm^2$) and the proportion (unit: %, hereinafter referred to as a residual film ratio) of a residual film thickness with respect to the initial film thickness when the resist film was developed for 30 seconds was plotted based on the obtained data of the variation in film thickness with time, to make a dose-residual film ratio curve. Based on this curve, the value of the exposure dose (Eth) required to reduce the residual film ratio to 0% was determined. Specifically, the exposure dose ($mJ/cm^2$) at the point where the dose-residual film ratio curve crosses a line of 0% residual film ratio was determined as Eth. This Eth value indicates the sensitivity of the resist composition. As this value becomes smaller, the sensitivity of the resist composition becomes higher.

An example of evaluation of triad fraction by the method for evaluating copolymer of the present embodiment is described hereinafter. However, the present embodiment is not limited to these evaluations of copolymer.

Synthesis Example A-1: Homopolymer A-A-1

In the present Synthesis Example, the following monomer (m-1) was polymerized by itself.

[Chemical Formula 3]

(m-1)

First, 5.00 parts of the monomer (m-1), 2.03 parts of dimethyl-2,2'-azobisisobutylate (trade name: V601, manufactured by Wako Pure Chemical Industries Ltd.), and 11.7 parts of ethyl lactate were added in a Schlenk flask of 25 ml, and nitrogen was injected into the solution for 1 minute at a rate of 200 ml/min. The flask was then bathed at 80° C. while stirring the content for 3 hours.

Then, the reaction solution thus obtained was added dropwise to methanol having a volume twenty times that of the reaction solution while stirring, to obtain a white precipitate (homopolymer A-A-1). Then, the washed precipitate was separated by filtration to obtain a wet polymer powder. The wet polymer powder was dried at 40° C. under reduced pressure for about 40 hours to obtain a white powder (4.45 g).

Synthesis Examples A-2 to A-5: Homopolymers A-A-2 to A-A-5

Homopolymers were formed respectively from monomers (m-2) to (m-5). The homopolymers A-A-2 to A-A-5 were obtained by the same operation as Synthesis Example A-1, except for changing the monomer used and the amount thereof as shown in Table 1. Feed compositions (feed monomer composition ratios) and yields of the homopolymers A-A-1 to A-A-5 obtained are shown in Table 1.

[Chemical Formula 4]

(m-2)

(m-3)

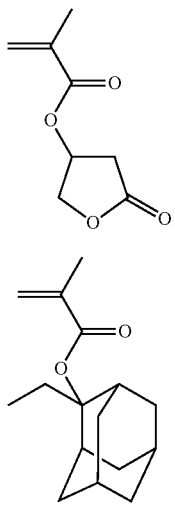

(m-4)

(m-5)

TABLE 1

| | Feed monomer mass/g | | | | | Feed monomer composition ratio/mol % | | | | | |
|---|---|---|---|---|---|---|---|---|---|---|---|
| Polymer | m-1 | m-2 | m-3 | m-4 | m-5 | m-1 | m-2 | m-3 | m-4 | m-5 | Yield/% |
| A-A-1 | 5.00 | | | | | 100 | | | | | 89.1 |
| A-A-2 | | 5.00 | | | | | 100 | | | | 78.6 |
| A-A-3 | | | 5.00 | | | | | 100 | | | 68.8 |
| A-A-4 | | | | 5.00 | | | | | 100 | | 91.2 |
| A-A-5 | | | | | 5.00 | | | | | 100 | 74.3 |

Synthesis Example A-6: Binary Copolymer A-B-1

In the present Synthesis Example, the monomers (m-1) and (m-2) were copolymerized.

A flask was charged with all of the monomers and a solvent in advance, and the copolymer was synthesized by the batch method. The molar ratio of the monomers used in this example is as follows:

(m-1):(m-2)=10.0:90.0

13.5 parts of ethyl lactate, 0.51 parts of the monomer (m-1), 5.29 parts of the monomer (m-2), 0.51 parts of the monomer (m-3), and 0.57 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring for three minutes, and the reaction solution was then rapidly cooled in an ice water bath.

Then, the reaction solution thus obtained was added dropwise to a mixture solvent of methanol and water (methanol/water=50/50 ratio by volume) having a volume approximately ten times that of the reaction solution while stirring, to obtain a white precipitate (copolymer A-B-1). Then, the washed precipitate was separated by filtration to obtain a wet polymer powder. The wet polymer powder was dried at 40° C. under reduced pressure for about 40 hours to obtain a white powder (0.232 g).

The average monomer composition ratio (hereinafter also referred to as copolymerization composition ratio) of the copolymer thus obtained was (m-1)/(m-2)=15.5/84.5 (mol %).

Synthesis Examples A-7 to A-32

The copolymers A-B-2 to A-B-27 were obtained by the same operation as Synthesis Example A-6, except for changing the amount of monomer used as shown in Tables 2 and 3. Yields and copolymer composition ratios of the copolymers A-B-2 to A-B-27 are shown in Tables 2 and 3.

Regarding Synthesis Examples A-6 to A-10, the copolymerization reactivity ratios of the monomer (m-1) and the monomer (m-2) obtained by the curve fitting method based on the feed monomer ratios and the copolymerization composition ratios of the copolymers A-B-1 to A-B-5 were r12=1.484, r21=0.583, respectively. Similarly, the copolymerization reactivity ratios were obtained from the copolymerization composition ratios of the copolymers A-B-6 to A-B-27, as shown in Table 4. A correspondence relationship between the copolymerization composition ratios of the copolymers A-B-1 to A-B-27 and the copolymerization reactivity ratios are shown in Table 4.

Synthesis Example A-33: Ternary Copolymer A-C-1

In the present Synthesis Example, the monomers (m-1), (m-2) and (m-3) were copolymerized.

A flask was charged with all of the monomers and a solvent in advance, and the copolymer was synthesized by the batch method. The molar ratio of the monomers used in this example is as follows:

(m-1):(m-2):(m-3)=30.0:30.0:40.0

14.3 parts of ethyl lactate, 1.53 parts of the monomer (m-1), 1.76 parts of the monomer (m-2), 2.83 parts of the monomer (m-3), and 1.41 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring for three minutes, and the reaction solution was then rapidly cooled in an ice water bath.

Then, the reaction solution thus obtained was added dropwise to a mixture solvent of methanol and water (methanol/water=50/50 ratio by volume) having a volume approximately ten times that of the reaction solution while stirring, to obtain a white precipitate (copolymer A-C-1). Then, the washed precipitate was separated by filtration to obtain a wet polymer powder. The wet polymer powder was dried at 40° C. under reduced pressure for about 40 hours to obtain a white powder (0.276 g).

Synthesis Examples A-34 to A-42

The copolymers A-C-2 to A-C-10 were obtained by the same operation as Synthesis Example A-33, except for changing the monomer used and the amount thereof as shown in Tables 5 and 6. Yields and copolymer composition ratios of the copolymers A-C-1 to A-C-10 are shown in Tables 5 and 6.

Following Examples A-D1 and A-D3 are examples of producing a copolymer by the partial dropping method of the embodiment (Z2') of the method for producing a polymer for lithography; Examples A-D2 and A-D4 are examples of producing a copolymer by the partial dropping method of the polymerization method (Z1); Examples A-E1 and A-E3 are examples of producing a copolymer by the total dropping method, and Examples A-E2 and A-E4 are examples of producing a copolymer by the batch method. Examples A-F1 and A-F2 are examples of obtaining estimates of monomer triad fractions of the copolymers obtained in these Examples.

Example A-D1: Copolymer A-D-1

Production of a Copolymer

In the present Example, the monomers (m-1), (m-2) and (m-3) were polymerized by the partial dropping method.

Two types of dropping solutions were used. After dropwise addition of a first dropping solution containing the above three monomers, a second dropping solution was added dropwise. The second dropping solution is configured such that the composition ratio of the monomer with the highest monomer consumption rate is greater than the composition ratio of said monomer in a total amount of solutions used for the polymerization reaction, and the monomer with the lowest monomer consumption rate is not contained.

The molar ratio of the monomers used in this example is as follows:
(m-1):(m-2):(m-3)=39.1:41.2:19.7

A flask equipped with a nitrogen introduction port, a stirrer, a condenser, a dropping funnel, and a temperature gauge was charged with: 99.3 parts of ethyl lactate; 3.99 parts of the monomer m-1; 7.68 parts of the monomer m-2; and 2.88 parts of the monomer m-3 in a nitrogen atmosphere. The flask was bathed. Then, the temperature of the bath was raised to 80° C. while stirring the content in the flask.

A solution containing 2.0 parts of the ethyl lactate and 1.280 parts of dimethyl-2,2'-azobisisobutylate (trade name: V601 mentioned above) was added dropwise at a fixed rate over 20 minutes in the flask from a dropping machine containing the solution. Thereafter, a solution containing 24.03 parts of the monomer m-1, 27.71 parts of the monomer m-2, 16.68 parts of the monomer m-3, 101.8 parts of ethyl lactate, and 0.690 parts of dimethyl-2,2'-azobisisobutylate (trade name: V601 mentioned above) was added dropwise at a fixed rate over 4 hours in the flask from a dropping machine containing the solution. Subsequently, 80 mass % of a solution containing 1.09 parts of the monomer m-1, 0.73 parts of the monomer m-3, 34.5 parts of ethyl lactate, and 0.054 parts of dimethyl-2,2'-azobisisobutylate (trade name: V601 mentioned above) was added dropwise over 1 hour and 20 mass % thereof was added dropwise over 1 hour.

After the dropwise addition, the flask was kept at 80° C. for 1 hour.

Then, the polymerization reaction solution in the flask was added dropwise to a mixture solvent of methanol and water (methanol/water=80/20 ratio by volume) having a volume approximately ten times that of the reaction solution while stirring to obtain a white precipitate (copolymer A-D-1). The precipitate was separated by filtration. Then, the separated precipitate was again poured into a mixture solvent of methanol and water (methanol/water=90/10 ratio by volume) having the same amount as above. Then, the mixture was washed while stirring. Then, the washed precipitate was separated by filtration to obtain a wet polymer powder. The wet polymer powder was dried at 40° C. under reduced pressure for about 40 hours to obtain a white powder (69.9 g).

The obtained white powder was analyzed by $^1$H-NMR and GPC to find the average monomer composition ratio, the molecular weight Mw and the distribution of molecular weight (Mw/Mn) of all copolymers. Also, the solubility of the obtained copolymer A-D-1 was evaluated by the above method. The results are shown in Table 7.

Table 7 shows: copolymer composition ratio; molecular weight (Mw); distribution of molecular weight; an estimate of monomer triad fraction as an evaluated value; time (minutes) showing solubility; and exposure dose as sensitivity, of the monomers m-1 to m-5 in compositions of copolymers A-D-1 to A-D-4 and A-E-1 to A-E-4.

(Production of a Resist Composition)

2 parts of triphenylsulfonium triflate as a photoacid generator and 700 parts of PGMEA as a solvent were blended with 100 parts of the obtained copolymer A-D-1 to obtain a homogeneous solution. Then, this solution was filtered through a membrane filter having a pore size of 0.1 μm to prepare a resist composition solution. The sensitivity of the resist composition thus obtained was evaluated by the above-described method. The results are shown in Table 7.

Example A-D2: Copolymer A-D-2

In the present Example, the monomers (m-1), (m-2) and (m-3) were polymerized by the partial dropping method.

As the dropping solution containing monomers, a single solution containing three monomers (m-1), (m-2) and (m-3) was used.

The molar ratio of the monomers used in this example is as follows:
(m-1):(m-2):(m-3)=39.0:41.3:19.7

A flask similar to that of Example A-D1 was charged with: 79.0 parts of ethyl lactate; 2.72 parts of the monomer (m-1); 4.90 parts of the monomer (m-2); and 2.02 parts of the monomer (m-3) in a nitrogen atmosphere. The flask was bathed. Then, the temperature of the bath was raised to 80° C. while stirring the content in the flask.

A solution containing 3.6 parts of the ethyl lactate and 1.196 parts of dimethyl-2,2'-azobisisobutylate (trade name: V601 mentioned above) was added dropwise at a fixed rate over 15 minutes in the flask from a dropping machine containing the solution. Thereafter, a solution containing 23.80 parts of the monomer (m-1), 27.44 parts of the monomer (m-2), 16.52 parts of the monomer (m-3), 98.06 parts of ethyl lactate, and 0.643 parts of dimethyl-2,2'-azobisisobutylate (trade name: V601 mentioned above) was added dropwise at a fixed rate over 4 hours in the flask from a dropping machine containing the solution. Thereafter, the flask was kept in a bath of 80° C. for 3 hours.

After that, a white precipitate (copolymer A-D-2) was obtained by the same procedures as in Example A-D1. The precipitate was then separated by filtration. Then, the separated precipitate was washed. After being washed, the precipitate was separated by filtration. The obtained precipitate was dried to obtain a white powder (66.0 g).

The obtained copolymer A-D-2 was measured and evaluated by the same procedures as in Example A-D1. The results are shown in Table 7.

Example A-E1: Copolymer A-E-1

In Example A-D1, a copolymer was synthesized by the total dropping method without any monomer existing in advance in the flask. The molar ratio of the monomers used in this example is as follows:
(m-1):(m-2):(m-3)=40.0:40.0:20.0

Specifically, the same flask that was used in Example A-D1 was charged with 64.5 parts of ethyl lactate in a nitrogen atmosphere. The flask was bathed. Then, the temperature of the bath was raised to 80° C. while stirring the content in the flask.

A solution containing 27.20 parts of the monomer (m-1), 31.36 parts of the monomer (m-2), 18.88 parts of the monomer (m-3), 112.6 parts of ethyl lactate, and 2.576 parts of dimethyl-2,2'-azobisisobutylate (trade name: V601 mentioned above) was added dropwise at a fixed rate over 4 hours in the flask from a dropping machine containing the solution. The flask was kept at 80° C. for 3 hours.

After that, a white precipitate (copolymer A-E-1) was obtained by the same procedures as in Example A-D1. The precipitate was then separated by filtration. Then, the separated precipitate was washed. After being washed, the precipitate was separated by filtration. The obtained precipitate was dried to obtain a white powder (64.0 g).

The obtained copolymer A-E-1 was measured and evaluated by the same procedures as in Example A-D1. The results are shown in Table 7.

Example A-E2: Copolymer A-E-2

In Example A-D1, a flask was charged with all of the monomers and a solvent in advance, and the copolymer was synthesized by the batch method. The molar ratio of the monomers used in this example is as follows:
(m-1):(m-2):(m-3)=40.0:40.0:20.0

15.5 parts of ethyl lactate, 1.36 parts of the monomer (m-1), 1.57 parts of the monomer (m-2), 0.94 parts of the monomer (m-3), and 1.15 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring the content for 3 hours.

Then, the reaction solution thus obtained was added dropwise to methanol having a volume approximately ten times that of the reaction solution while stirring, to obtain a white precipitate (copolymer A-E-2). Then, the washed precipitate was separated by filtration to obtain a wet polymer powder. The wet polymer powder was dried at 40° C. under reduced pressure for about 40 hours to obtain a white powder (2.8 g).

The obtained copolymer A-E-2 was measured and evaluated by the same procedures as in Example A-D1. The results are shown in Table 7.

Example A-D3: Copolymer A-D-3

Production of a Copolymer

In the present Example, the monomers (m-4), (m-5) and (m-3) were polymerized by the partial dropping method.

The molar ratio of the monomers used in this example is as follows:
(m-4):(m-5):(m-3)=39.1:41.2:19.7

A flask equipped with a nitrogen introduction port, a stirrer, a condenser, a dropping funnel, and a temperature gauge was charged with: 46.5 parts of ethyl lactate; 46.5 parts of PGMEA; 2.60 parts of the monomer m-4; 10.13 parts of the monomer m-5; and 3.30 parts of the monomer m-3 in a nitrogen atmosphere. The flask was bathed. Then, the temperature of the bath was raised to 80° C. while stirring the content in the flask.

A solution containing 6.5 parts of the ethyl lactate and 2.174 parts of dimethyl-2,2'-azobisisobutylate (trade name: V601 mentioned above) was added dropwise at a fixed rate over 20 minutes in the flask from a dropping machine containing the solution. Along with the dropwise addition, a solution containing 16.66 parts of the monomer m-4, 24.30 parts of the monomer m-5, 24.00 parts of the monomer m-3, 26.9 parts of ethyl lactate, 33.4 parts of PGMEA, and 1.450 parts of dimethyl-2,2'-azobisisobutylate (trade name: V601 mentioned above) was added dropwise at a fixed rate over 4 hours in the flask from a dropping machine containing the solution.

Subsequently, 80 mass % of a solution containing 1.00 parts of the monomer m-4, 1.12 parts of the monomer m-3, 12.2 parts of ethyl lactate, and 12.2 parts of PGMEA, and 0.110 parts of dimethyl-2,2'-azobisisobutylate (trade name: V601 mentioned above) was added dropwise over 1 hour and 20 mass % thereof was added dropwise over 1 hour. The flask was kept at 80° C. for 1 hour.

Then, the polymerization reaction solution in the flask was added dropwise to a mixture solvent of methanol and water (methanol/water=85/15 ratio by volume) having a volume approximately ten times that of the reaction solution while stirring to obtain a white precipitate (copolymer A-D-3). Then, the precipitate was separated by filtration. Then, the separated precipitate was again poured into a mixture solvent of methanol and water (methanol/water=95/5 ratio by volume) having the same amount as above. Then, the mixture was washed while stirring. Then, the washed precipitate was separated by filtration to obtain a wet polymer powder.

The wet polymer powder was dried at 40° C. under reduced pressure for about 40 hours to obtain a white powder (57.5 g).

The obtained white powder was analyzed by $^1$H-NMR and GPC to find the average monomer composition ratio, the molecular weight Mw and the distribution of molecular weight (Mw/Mn) of all copolymers. Also, the solubility of the obtained copolymer A-D-3 was evaluated by the above method. The results are shown in Table 7.

(Production of a Resist Composition)

2 parts of triphenylsulfonium triflate as a photoacid generator and 700 parts of PGMEA as a solvent were blended with 100 parts of the obtained copolymer A-D-3 to obtain a homogeneous solution. Then, this solution was filtered through a membrane filter having a pore size of 0.1 μm to prepare a resist composition solution. The sensitivity of the obtained resist composition was evaluated by the above method. The results are shown in Table 7.

Example A-D4: Copolymer A-D-4

In the present Example, the monomers (m-4), (m-5) and (m-3) were polymerized by the partial dropping method. As the dropping solution containing monomers, a single solution containing three monomers (m-4), (m-5) and (m-3) was used.

The molar ratio of the monomers used in this example is as follows:

(m-4):(m-5):(m-3)=33.9:35.1:30.1

A flask similar to that of Example A-D1 was charged with: 42.6 parts of ethyl lactate; 42.6 parts of PGMEA; 1.42 parts of the monomer (m-4); 8.68 parts of the monomer (m-5); and 3.52 parts of the monomer (m-3) in a nitrogen atmosphere. The flask was bathed. Then, the temperature of the bath was raised to 80° C. while stirring the content in the flask.

A solution containing 6.5 parts of the ethyl lactate and 2.152 parts of dimethyl-2,2'-azobisisobutylate (trade name: V601 mentioned above) was added dropwise at a fixed rate over 20 minutes in the flask from a dropping machine containing the solution. Along with the dropwise addition, a solution containing 18.09 parts of the monomer (m-4), 20.83 parts of the monomer (m-5), 21.15 parts of the monomer (m-3), 38.6 parts of ethyl lactate, 45.1 parts of PGMEA, and 1.435 parts of dimethyl-2,2'-azobisisobutylate (trade name: V601 mentioned above) was added dropwise at a fixed rate over 4 hours in the flask from a dropping machine containing the solution. Thereafter, the flask was kept in a bath of 80° C. for 3 hours.

After that, a white precipitate (copolymer A-D-4) was obtained by the same procedures as in Example A-D3. The precipitate was then separated by filtration. Then, the separated precipitate was washed. After being washed, the precipitate was separated by filtration. The obtained precipitate was dried to obtain a white powder (54.1 g).

The obtained copolymer A-D-4 was measured and evaluated by the same procedures as in Example A-D3. The results are shown in Table 7.

Example A-E3: Copolymer A-E-3

In Example A-D3, a copolymer was synthesized by the total dropping method without any monomer existing in advance in the flask. The molar ratio of the monomers used in this example is as follows:

(m-4):(m-5):(m-3)=35.0:35.0:30.0

Specifically, the same flask that was used in Synthesis Example A-7 was charged with 54.5 parts of ethyl lactate and 23.3 parts of PGMEA in a nitrogen atmosphere. The flask was bathed. Then, the temperature of the bath was raised to 80° C. while stirring the content in the flask.

A solution containing 51.17 parts of the monomer (m-4), 37.32 parts of the monomer (m-5), 30.44 parts of the monomer (m-3), 98.0 parts of ethyl lactate, 16.4 parts of PGMEA, and 5.538 parts of dimethyl-2,2'-azobisisobutylate (trade name: V601 mentioned above) was added dropwise at a fixed rate over 4 hours in the flask from a dropping machine containing the solution. Thereafter, the flask was kept in a bath of 80° C. for 3 hours.

After that, a white precipitate (copolymer A-E-3) was obtained by the same procedures as in Example A-D3. The precipitate was then separated by filtration. Then, the separated precipitate was washed. After being washed, the precipitate was separated by filtration. The obtained precipitate was dried to obtain a white powder (51.0 g).

The obtained copolymer A-E-3 was measured and evaluated by the same procedures as in Example A-D2. The results are shown in Table 7.

Example A-E4: Copolymer A-E-4

In Example A-D2, a flask was charged with all of the monomers and a solvent in advance, and the copolymer was synthesized by the batch method. The molar ratio of the monomers used in this example is as follows:

(m-4):(m-5):(m-3)=36.0:32.0:32.0

4.9 parts of ethyl lactate, 4.9 parts of PGMEA, 1.84 parts of the monomer (m-4), 2.38 parts of the monomer (m-5), 2.27 parts of the monomer (m-3), and 1.725 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring the content for 3 hours.

Then, the reaction solution thus obtained was added dropwise to methanol having a volume approximately ten times that of the reaction solution while stirring, to obtain a white precipitate (copolymer A-E-4). Then, the washed precipitate was separated by filtration to obtain a wet polymer powder. The wet polymer powder was dried at 40° C. under reduced pressure for about 40 hours to obtain a white powder (6.1 g).

The obtained copolymer A-E-4 was measured and evaluated by the same procedures as in Example A-D2. The results are shown in Table 7.

Example A-F1

In the following evaluation of copolymer, the triad fraction of single-type monomer for each monomer composing the copolymer in each polymer was obtained by sequentially performing the target variable analysis process (I); the explanatory variable analysis process (II); the model generation process (III); and the sample analysis process (IV) in the method for evaluating copolymer according to the present embodiment.

For 23 types of polymers: the homopolymers A-A-1 to A-A-3 obtained in Synthesis Examples A-1 to A-3; copolymers A-B-1 to A-B-15 obtained in Synthesis Examples A-6 to A-20; and copolymers A-C-1 to A-C-5 obtained in Synthesis Examples A-33 to A-37, the $^{13}$C-NMR measurement was conducted and spectra were obtained. The number of scans in the measurement was 5000; zero-filling was performed twice during the FID processing; the broadening factor was 2.0 Hz; the base peak was chloroform (77.0 ppm); and the baseline correction was performed.

The $^{13}$C-NMR measurement was conducted using a mixture solvent of deuterated chloroform and deuterated dimethylsulfoxide (50/50 ratio by volume) as a solvent and at a measurement temperature of 40° C.

In each of the spectra thus obtained, a range of chemical shift derived from carbonyl carbon in the polymer, i.e. a range of 175.00 to 179.00 ppm, was integrated (peak integration) at intervals of 0.1 ppm, and 40 integral values were obtained (target variable analysis process, explanatory variable analysis process).

Meanwhile, the feed compositions of the copolymers A-B-1 to A-B-15 and A-C-1 to A-C-5 of which polymerization rate is no greater than 10% and the copolymerization reactivity ratios obtained as described above are assigned to the following equations, to obtain respective triad fractions P{111} (%), P{222} (%), and P{333} (%) of the three monomer units in the copolymers A-B-1 to A-B-15 and A-C-1 to A-C-5 (target variable analysis process). The results are shown in Tables 2 and 5. Here, the triad fraction P{XXX} of monomer unit indicates a triad fraction of a single-type monomer unit in the monomer unit X.

$$P11=[M1]/([M1]+[M1]/r12+[M1]/r13)$$

$$P22=[M2]/([M1]/r21+[M1]+[M1]/r23)$$

$P33=[M3]/([M1]/r31+[M1]/r32+[M1])$ $P\{111\}(\%)=100\times[M1']\times P11\times P11$ $P\{222\}(\%)=100\times[M2']\times P22\times P22$ $P\{333\}(\%)=100\times[M3']\times P33\times P33$ Here, P11, P22, P33 are probabilities to react with m-1, m-2, m-3 when m-1, m-2, m-3 exist on the growing end; [M1], [M2], [M3] are feed composition ratios of m-1, m-2, m-3; and [M1'], [M2'], [M3'] are copolymer composition ratios of m-1, m-2, m-3, respectively.

Next, using Sirius (registered trademark) manufactured by Pattern Recognition Systems as multivariate analysis software, an experimental model was constructed by partial least squares (PLS) with: 920 integral values regarding carbonyl carbon of the homopolymers A-A-1 to A-A-3 and the copolymers A-B-1 to A-B-15 and A-C-1 to A-C-5 as explanatory variables; and triad fractions P{111} (%), P{222} (%), P{333} (%) of the three types of monomer units as target variables (model generation process). In the present embodiment, mol % is used that is simply referred to as %.

Then, using 160 integral values regarding carbonyl carbon of the copolymers A-D-1 to A-D-2 and copolymers A-E-1 to A-E-2 obtained in Examples A-D1 to A-D2 and A-E1 to A-E-2 with the experimental model, triad fractions were calculated by the following multivariate analysis software (sample analysis process). Here, using, for example, Sirius (registered trademark) manufactured by Pattern Recognition Systems as multivariate analysis software, estimates of triad fractions (%) of the single-type monomer units of the three monomer units were obtained by partial least squares (PLS) described in the method for evaluating copolymer according to the present embodiment. The results are shown in Table 7.

Example A-F2

By the process described in the method for evaluating copolymer according to the present embodiment, in other words as in the descriptions for Example A-F1, the triad fraction of the single-type monomer units in the composition of copolymer was calculated. For 20 types of polymers: the homopolymers A-A-3 to A-A-5 obtained in Synthesis Examples A-3 to A-5; copolymers A-B-16 to A-B-27 obtained in Synthesis Examples A-21 to A-32; and copolymers A-C-6 to A-C-10 obtained in Synthesis Examples A-38 to A-42, the $^{13}$C-NMR measurement was conducted and NMR spectrum signals were obtained.

Baseline correction was performed in conditions in which: the number of scans in the measurement is 5000; zero-filling was performed twice during the FID processing; the broadening factor was 2.0 Hz, and the base peak was chloroform (77.0 ppm). The $^{13}$C-NMR measurement was conducted using a mixture solvent of deuterated chloroform and deuterated dimethylsulfoxide (50/50 ratio by volume) as a solvent and at a measurement temperature of 40° C.

In each of the spectra thus obtained, a range of 175.00 to 179.00 ppm derived from carbonyl carbon in the polymer was integrated at intervals of 0.1 ppm, and 40 integral values were obtained (target variable analysis process, explanatory variable analysis process).

As in Example A-F1, triad monomer (unit) chain fractions P{444} (%), P{555} (%), P{333} (%) of three monomers in the copolymers A-B-16 to A-B-27 and A-C-6 to A-C-10 were obtained (target variable analysis process). The results are shown in Tables 3 and 6.

Next, an experimental model was constructed by partial least squares (PLS) with: 800 integral values regarding carbonyl carbon of the homopolymers A-A-4 to A-A-5 and the copolymers A-B-16 to A-B-27 and A-C-6 to A-C-10 as explanatory variables; and the three triad monomer (unit) chain fractions P{444} (%), P{555} (%), P{333} (%) as target variables (model generation process).

Then, using x160 integral values regarding carbonyl carbon of the copolymers A-D-3 to A-D-4 and copolymers A-E-3 to A-E-4 respectively obtained in Examples A-D3 to A-D4 and A-E3 to A-E4 with the experimental model, estimates of triad fractions of each of the three monomer units were calculated using the partial least squares (PLS), by the method for evaluating copolymer according to the present embodiment (sample analysis process). The results are shown in Table 7.

TABLE 2

| Copolymer | Feed monomer mass/g | | | Feed monomer composition ratio/mol/mol % | | | Copolymerization composition ratio/mol % | | | Yield/% | Monomer triad fraction | | |
|---|---|---|---|---|---|---|---|---|---|---|---|---|---|
| | m-1 | m-2 | m-3 | m-1 | m-2 | m-3 | m-1 | m-2 | m-3 | | P{111} % | P{222} % | P{333} % |
| A-B-1 | 0.51 | 5.29 | | 10 | 90 | | 15.5 | 84.5 | | 4.5 | 0.3 | 59.5 | |
| A-B-2 | 1.53 | 4.12 | | 30 | 70 | | 40.6 | 59.4 | | 5.1 | 6.2 | 19.6 | |
| A-B-3 | 2.55 | 2.94 | | 50 | 50 | | 61.9 | 38.1 | | 6.3 | 21.8 | 5.3 | |
| A-B-4 | 3.57 | 1.76 | | 70 | 30 | | 77.5 | 22.5 | | 7.2 | 47.0 | 0.9 | |
| A-B-5 | 4.59 | 0.59 | | 90 | 10 | | 92.3 | 7.7 | | 8.3 | 80.6 | 0.0 | |
| A-B-6 | | 0.59 | 6.37 | | 10 | 90 | | 10.9 | 89.1 | 8.1 | | 0.1 | 76.2 |
| A-B-7 | | 1.76 | 4.96 | | 30 | 70 | | 26.0 | 74.0 | 7.0 | | 3.4 | 38.5 |
| A-B-8 | | 2.94 | 3.54 | | 50 | 50 | | 53.0 | 47.0 | 5.7 | | 15.3 | 14.6 |
| A-B-9 | | 4.12 | 2.12 | | 70 | 30 | | 70.7 | 29.3 | 4.1 | | 39.5 | 3.2 |
| A-B-10 | | 5.29 | 0.71 | | 90 | 10 | | 91.3 | 8.7 | 3.7 | | 76.9 | 0.1 |
| A-B-11 | 4.59 | | 0.71 | 90 | | 10 | 92.1 | | 7.9 | 8.9 | 75.0 | | 0.1 |
| A-B-12 | 3.57 | | 2.12 | 70 | | 30 | 70.6 | | 29.4 | 8.3 | 37.1 | | 2.7 |
| A-B-13 | 2.55 | | 3.54 | 50 | | 50 | 50.8 | | 49.2 | 7.8 | 14.1 | | 12.8 |
| A-B-14 | 1.53 | | 4.96 | 30 | | 70 | 30.3 | | 69.7 | 7.6 | 3.1 | | 35.1 |
| A-B-15 | 0.51 | | 6.37 | 10 | | 90 | 10.0 | | 90.0 | 8.1 | 0.1 | | 73.6 |

TABLE 3

| Copolymer | Feed monomer mass/g | | | Feed monomer composition ratio/mol % | | | Copolymerization composition ratio/mol % | | | Yield/% | Monomer triad fraction | | |
|---|---|---|---|---|---|---|---|---|---|---|---|---|---|
| | m-4 | m-5 | m-3 | m-4 | m-5 | m-3 | m-4 | m-5 | m-3 | | P{444} % | P{555} % | P{333} % |
| A-B-16 | 1.02 | 5.95 | | 20 | 80 | | 39.4 | 60.6 | | 4.0 | 2.5 | 14.2 | |
| A-B-17 | 2.04 | 4.46 | | 40 | 60 | | 58.2 | 41.8 | | 4.2 | 12.6 | 2.9 | |
| A-B-18 | 3.06 | 2.98 | | 60 | 40 | | 71.6 | 28.4 | | 4.3 | 31.6 | 0.5 | |
| A-B-19 | 4.08 | 1.49 | | 80 | 20 | | 85.8 | 14.2 | | 6.2 | 60.3 | 0.0 | |
| A-B-20 | | 1.49 | 5.66 | | 20 | 80 | | 16.8 | 83.2 | 7.1 | | 0.2 | 61.7 |
| A-B-21 | | 2.98 | 4.25 | | 40 | 60 | | 27.7 | 72.3 | 6.3 | | 2.2 | 30.8 |
| A-B-22 | | 4.46 | 2.83 | | 60 | 40 | | 48.7 | 51.3 | 4.9 | | 9.1 | 12.3 |
| A-B-23 | | 5.95 | 1.42 | | 80 | 20 | | 68.9 | 31.1 | 4.3 | | 31.5 | 2.1 |
| A-B-24 | 4.08 | | 1.42 | 80 | | 20 | 83.0 | | 17.0 | 8.9 | 63.6 | | 1.0 |
| A-B-25 | 3.06 | | 2.83 | 60 | | 40 | 60.3 | | 39.7 | 8.3 | 32.3 | | 8.0 |
| A-B-26 | 2.04 | | 4.25 | 40 | | 60 | 33.8 | | 66.2 | 7.8 | 11.0 | | 26.5 |
| A-B-27 | 1.02 | | 5.66 | 20 | | 80 | 17.5 | | 82.5 | 7.6 | 1.5 | | 58.3 |

TABLE 4

| r12 | 1.484 |
|---|---|
| r21 | 0.583 |
| r23 | 1.229 |
| r32 | 1.190 |
| r31 | 1.040 |
| r13 | 1.109 |
| r45 | 1.313 |
| r54 | 0.239 |
| r53 | 0.517 |
| r35 | 1.410 |
| r34 | 1.348 |
| r43 | 1.617 |

TABLE 5

| Copolymer | Feed monomer mass/g | | | Feed monomer composition ratio/mol % | | | Copolymerization composition ratio/mol % | | | Yield/% | Monomer triad fraction | | |
|---|---|---|---|---|---|---|---|---|---|---|---|---|---|
| | m-1 | m-2 | m-3 | m-1 | m-2 | m-3 | m-1 | m-2 | m-3 | | P{111} % | P{222} % | P{333} % |
| A-C-1 | 1.53 | 1.76 | 2.83 | 30 | 30 | 40 | 34.7 | 24.1 | 41.2 | 4.5 | 4.3 | 1.8 | 7.0 |
| A-C-2 | 1.53 | 2.94 | 1.42 | 30 | 50 | 20 | 35.1 | 42.6 | 22.3 | 5.1 | 5.2 | 7.7 | 0.9 |
| A-C-3 | 2.04 | 2.35 | 1.42 | 40 | 40 | 20 | 48.4 | 28.1 | 23.5 | 6.3 | 10.8 | 3.4 | 0.9 |
| A-C-4 | 2.30 | 2.65 | 0.71 | 45 | 45 | 10 | 51.1 | 36.7 | 12.2 | 7.2 | 15.6 | 4.3 | 0.1 |
| A-C-5 | 2.55 | 1.76 | 1.42 | 50 | 30 | 20 | 59.6 | 16.9 | 23.5 | 8.3 | 18.5 | 1.2 | 0.9 |

TABLE 6

| Copolymer | Feed monomer mass/g | | | Feed monomer composition ratio/mol % | | | Copolymerization composition ratio/mol % | | | Yield/% | Monomer triad fraction | | |
|---|---|---|---|---|---|---|---|---|---|---|---|---|---|
| | m-4 | m-5 | m-3 | m-4 | m-5 | m-3 | m-4 | m-5 | m-3 | | P{444} % | P{555} % | P{333} % |
| A-C-6 | 1.28 | 1.86 | 3.54 | 25 | 25 | 50 | 15.5 | 84.5 | 0.0 | 4.5 | 3.3 | 0.2 | 16.8 |
| A-C-7 | 1.02 | 3.72 | 2.12 | 20 | 50 | 30 | 40.6 | 59.4 | 0.0 | 5.1 | 2.1 | 2.6 | 4.3 |
| A-C-8 | 1.79 | 2.60 | 2.12 | 35 | 35 | 30 | 61.9 | 38.1 | 0.0 | 6.3 | 8.6 | 0.6 | 3.8 |
| A-C-9 | 2.30 | 3.35 | 0.71 | 45 | 45 | 10 | 77.5 | 22.5 | 0.0 | 7.2 | 16.4 | 1.0 | 0.1 |
| A-C-10 | 2.55 | 2.23 | 1.42 | 50 | 30 | 20 | 92.3 | 7.7 | 0.0 | 8.3 | 20.9 | 0.3 | 1.1 |

TABLE 7

| Copolymer | Copolymerization composition ratio/mol % | | | | | Molecular weight | | Monomer triad fraction estimate | | |
|---|---|---|---|---|---|---|---|---|---|---|
| | m-1 | m-2 | m-3 | m-4 | m-5 | Mw | Mw/Mn | P{111} % | P{222} % | P{333} % |
| A-D-1 | 40 | 40 | 20 | | | 10,500 | 1.65 | 4.9 | 3.1 | 3.3 |
| A-D-2 | 40 | 41 | 19 | | | 10,000 | 1.66 | 4.9 | 4.6 | 3.2 |
| A-D-3 | | | 31 | 37 | 32 | 8,400 | 1.62 | | | 4.0 |
| A-D-4 | | | 31 | 37 | 32 | 8,200 | 1.59 | | | 4.1 |
| A-E-1 | 41 | 39 | 20 | | | 10,600 | 1.75 | 9.5 | 4.8 | 8.0 |

TABLE 7-continued

| | | | | | | | | | |
|---|---|---|---|---|---|---|---|---|---|
| A-E-2 | 46 | 40 | 14 | | | 10,000 | 2.21 | 17.6 | 5.8 | 10.1 |
| A-E-3 | | | 30 | 37 | 33 | 7,400 | 1.78 | | | 6.8 |
| A-E-4 | | | 28 | 37 | 35 | 7,500 | 2.05 | | | 7.1 |

| Copolymer | Monomer triad fraction estimate | | | Solubility/ min | Senstivity/ mJ · cm$^2$ |
|---|---|---|---|---|---|
| | P{444} % | P{555} % | Total | | |
| A-D-1 | | | 11.3 | 12 | 1.01 |
| A-D-2 | | | 12.7 | 17 | 1.21 |
| A-D-3 | 5.2 | 2.3 | 11.5 | 9 | 0.51 |
| A-D-4 | 5.1 | 3.4 | 12.6 | 12 | 0.54 |
| A-E-1 | | | 22.3 | 31 | 1.61 |
| A-E-2 | | | 33.5 | Residue present | Evaluation not possible |
| A-E-3 | 6.5 | 9.1 | 22.4 | 18 | 0.78 |
| A-E-4 | 8.5 | 19.4 | 35.0 | Residue present | Evaluation not possible |

As obvious from Table 7, in the composition of copolymer, smaller total value of estimates of triad fractions of the single-type monomer units results in higher sensitivity and solubility of a resist composition produced using the copolymer.

In other words, as shown in Table 7, it has been found that the resist compositions produced using the copolymers obtained in Examples A-D1 to A-D4 in which the total value of estimates of triad fractions of single-type monomer units is smaller than 20(%), preferably smaller than 15(%), are superior in sensitivity and solubility than the resist compositions produced using the copolymers with the total value of estimates of triad fractions exceeding 20(%), preferably 15(%).

On the other hand, the resist compositions in which the total value of triad fractions of single-type monomer units exceeds 30(%) leave residue with regard to solubility, and sensitivity to light irradiation cannot be assessed due to the residue. Given this, it has been found that the copolymer having the total value of triad fractions of single-type monomer units greater than 30(%) is not suitable for producing a resist composition used in a lithographic process.

As described above, it is obvious from Table 7 that the numerical value of triad fractions in a copolymer obtained by the method for evaluating copolymer according to the present embodiment is highly correlated to solubility and sensitivity of a resist composition produced using the copolymer.

Therefore, by forming a copolymer and calculating the triad fraction thereof by the method for evaluating copolymer of the present embodiment, a method for producing a copolymer necessary for production of a resist composition and an adjusted amount of monomers can be simply configured, without an effort of actually producing a resist composition and evaluating solubility and sensitivity thereof.

In addition, the control unit 18 has a correspondence relationship between: the total value of the triad fractions; and characteristic values (solubility and sensitivity) of a resist composition produced using the copolymer corresponding to the total value, stored therein (alternatively, stores to and reads from the storage unit 16), and estimates the characteristic values of a composition produced using a copolymer as an unknown sample from the total value of triad fractions of the unknown sample.

In the evaluation method of the present embodiment, it is preferable that the control unit has a correspondence relationship between: the total value of the triad fractions; and characteristic values of a composition produced using the copolymer corresponding to the total value, and further comprises a control process of estimating a characteristic value of a composition produced using a copolymer as an unknown sample from the total value of triad fractions of the unknown sample.

In addition, in the method for evaluating copolymer of the present embodiment, it is preferable that the copolymer is a copolymer for lithography, the composition is a lithography composition, and the characteristics value of the composition is solubility to a solvent or sensitivity to light irradiation of the composition.

For example, upper limits of sensitivity and solubility of a resist composition required upon pattern formation in production of a semiconductor device are defined based on exposure conditions and the like in a lithography process.

The total value of triad fractions exceeding the upper limits of sensitivity and solubility, as thresholds, is stored in the storage unit 16 in advance as a triad fraction threshold limit.

A resist composition with superior sensitivity and solubility can be simply produced in such a way that: various monomer amounts for production and various production methods are tried; triad fractions of copolymers produced as a result of the trials are obtained by the PLS based on values obtained by the NMR measurement as described above; and a copolymer having the total value of triad fractions no greater than the triad fraction threshold limit is selected from the copolymers produced as a result of the trials.

Here, the control unit 18 determines whether the copolymer obtained has characteristics suitable for a resist composition or not, by comparing the triad fraction threshold limit being set internally with the total value of triad fractions being obtained.

In other words, the control unit 18 determines that the copolymer is suitable for production of a resist composition if the total value of triad fractions is smaller than the triad fraction threshold limit; and that the copolymer is not suitable for production of a resist composition if the total value of triad fractions is greater than the triad fraction threshold limit. The control unit 18 then displays respective results of determination for copolymers on the display unit 17.

By forming a resist pattern on a substrate, e.g. a semiconductor substrate, using the resist composition thus produced, high precision in formation of a fine resist pattern corresponding to a fine pattern of an exposure mask can be realized.

In other words, production of a substrate with a pattern formed thereon, comprising: a step of applying the resist composition on the substrate; a step of exposing to light having a wavelength of no greater than 250 nm; and a step of developing using a developing agent, is realized.

Here, the wavelength is defined to be no greater than 250 nm since the resist composition of the present embodiment conforms to a lithography technology using KrF excimer laser (wavelength: 248 nm), ArF excimer laser (wavelength: 193 nm), EUV (extreme ultraviolet) excimer laser (wavelength: 1.3 nm) and the like.

The resist composition of the present embodiment is a so-called chemical amplification type resist, as a resist compound suitably applicable to shorten the wavelength of irradiation light and to pattern microfabrication. Such a chemical amplification type resist includes a polymer, which becomes soluble in alkali when an acid-eliminable group is dissociated by the action of an acid, and a photoacid generator.

In addition, for a copolymer used for producing the resist composition of the present embodiment, the triad fraction threshold limit is defined such that the total of triad fractions of the single-type monomer units is no greater than 20 mol %, preferably no greater than 15 mol %, and more preferably no greater than 13 mol %, as can be determined from Table 7.

The resist composition of the present embodiment is prepared by using a copolymer (copolymer for resist) and a compound that generates an acid by irradiation with active rays (light irradiation) or radial rays.

In the method for evaluating copolymer of the present embodiment, in evaluation of a copolymer for lithography composed of monomer (constitutional) units $\alpha'_1$ to $\alpha'_n$ derived from at least two types of monomers $\alpha_1$ to $\alpha_n$ for production of semiconductor (n denoting an integer of at least 2) that has been polymerized, the control unit can determine that the copolymer for lithography of which total of triad fractions of a single-type monomers is no greater than 20 mol % of the copolymer is suitable for production of a lithography composition. The total of the triad fractions used for the abovementioned determination is more preferably no greater than 15 mol %, even more preferably no greater than 13 mol %.

The storage unit 16 is composed of: non volatile memory such as a hard disk, a magneto-optical disk, and flash memory; a read-only storage medium such as a CD-ROM; volatile memory such as RAM (Random Access Memory); or a combination thereof.

It should be noted that the target variable analysis unit 11, the waveform processing unit 12, the explanatory variable analysis unit 13, the model generation unit 14, and the sample analysis unit 15 in FIG. 1 can be realized by dedicated hardware or by combinations of memory and microprocessors. Alternatively, these units can be composed of combinations of memory and CPUs (Central Processing Units), and realized by loading programs that provide functions thereof into the memory and executing.

In addition, to the copolymer evaluation apparatus that evaluates copolymers by the present method for evaluating copolymer, peripherals such as an input device and the like (not illustrated) are connected. As used herein, the input device indicates a keyboard, a mouse and the like. The display unit 17 indicates a CRT (Cathode Ray Tube) display device, a liquid crystal display device and the like.

A calculation process of triad fraction can be performed by storing programs providing functions of the target variable analysis unit 11, the waveform processing unit 12, the explanatory variable analysis unit 13, the model generation unit 14, and the sample analysis unit 15 in FIG. 1 into a computer-readable storage medium, and making a computer system read and execute the programs stored in the storage medium. As used herein, the "computer system" includes an OS and hardware such as peripherals.

In addition, in a case of using a WWW system, the "computer system" includes a web page providing environment (or displaying environment).

In addition, the "computer-readable storage medium" indicates a storage device such as: a portable medium e.g. a flexible disk, a magneto-optical disk, ROM, and CD-ROM; a built-in hard disk in the computer system; and the like. The "computer-readable storage medium" also includes: a medium that holds a program dynamically for a small amount of time such as a communication cable; and a medium that holds the program for a certain amount of time such as volatile memory in a computer system that functions as a server or a client, in a case of transmitting the program through a network such as internet and a communication line such as a telephone line. Furthermore, the program can provide a part of the abovementioned functions, or can provide the abovementioned functions by combinations of programs stored in the computer system in advance.

An example of the method for producing a copolymer for lithography of the present embodiment is described hereinafter.

Reference Example B-1: Design of Composition of a Solution Uc Used in the Later Step In this example, a composition of Uc was determined in the case of polymerizing monomers m-1, m-2 and m-3 represented by the above formulae (m-1), (m-2) and (m-3) respectively to produce a polymer so designed that its target composition ratio was m-1:m-2:m-3=40:40:20 (mol %) and its target value of weight-average molecular weight was 10,000.

The polymerization initiator used in the present example was dimethyl-2,2'-azobisisobutylate (trade name: V601, manufactured by Wako Pure Chemical Industries Ltd.). The polymerization temperature was set to 80° C.

A flask (reactor) equipped with a nitrogen introduction port, a stirrer, a condenser, a dropping funnel, and a temperature gauge was charged with 67.8 parts of ethyl lactate in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.

Monomer m-1: 28.56 parts (40 mol %);
Monomer m-2: 32.93 parts (40 mol %);
Monomer m-3: 19.82 parts (20 mol %);
Ethyl lactate: 122.0 parts; and
Dimethyl-2,2'-azobisisobutylate: 2.415 parts (2.5 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-1 to m-3 were respectively measured quantitatively. Thus, the mass of each monomer left in a flask is determined. As a result, for example, the results obtained 2 hours and 3 hours after the dropwise addition is started are shown in Table 8.

TABLE 8

|  | After 2 hours (parts by mass) | After 3 hours (parts by mass) |
|---|---|---|
| Monomer m-1 (Mx) | 4.00 | 4.00 |
| Monomer m-2 (My) | 7.24 | 7.75 |
| Monomer m-3 (Mz) | 2.89 | 2.90 |

Then, the mass of each monomer was converted into the molar ratio (corresponding to Mx:My:Mz) of each monomer left in a flask at each time of sampling by using the molecular weight of each monomer.

As a result, for example, the results obtained 2 hours and 3 hours after the dropwise addition is started are shown in Table 9.

TABLE 9

|  | After 2 hours (mol %) | After 3 hours (mol %) |
|---|---|---|
| Monomer m-1 (Mx) | 32.35 | 31.32 |
| Monomer m-2 (My) | 50.79 | 52.49 |
| Monomer m-3 (Mz) | 16.86 | 16.31 |

On the other hand, the total mass of each monomer fed until each sampling time was determined from the mass (total feed amount) of each monomer fed to the flask at a fixed rate for 4 hours. Then, with regard to each monomer, the mass of the monomer left in the flask at each sampling time was subtracted from this total mass to thereby calculate the mass of the monomer converted into a polymer at each sampling time among the monomer fed until the sampling time.

Then, with regard to each monomer, data of a difference between each sampling time was taken to find the mass of the monomer converted into a polymer between each sampling time. Then, this mass was converted into a molar fraction. The value of this molar fraction corresponds to the content ratio (hereinafter also referred to as a polymer composition ratio) Px:Py:Pz of the monomer units in a polymer produced between each sampling time. The term "a polymer produced between each sampling time" means each polymer produced while the times (reaction times) elapsed from the start of dropwise addition were from $t_1$ to $t_2$, from $t_2$ to $t_3$ ... and the like.

Figure 5:
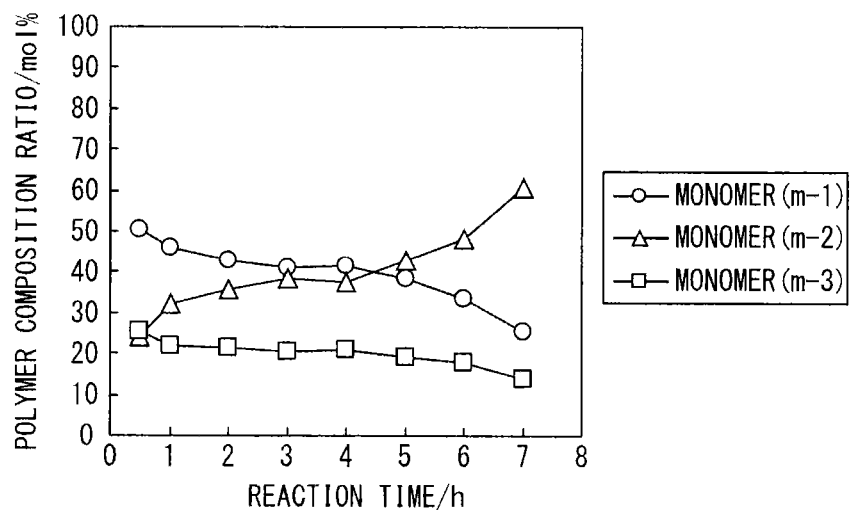
FIG. 5 is a chart showing results of Reference Example B-1.

The results are shown in FIG. 5. The abscissa in FIG. 5 is the end side reaction time of each reaction time zone (between each sampling time). In FIG. 5, when, for example, the reaction time of the abscissa is 4 hours, the data corresponds to the data of a polymer produced between 3 hours and 4 hours after the start of the dropwise addition (same as follows).

As shown by the results in FIG. 5, the polymer composition ratio (Px:Py:Pz) in a polymer produced 2 hour to 3 hours after the dropwise addition was started was closest to the target composition ratio 40:40:20.

The value of the polymer composition ratio was as follows: Px:Py:Pz=41.05:38.47:20.48. Using this value and the value (Table 9) Mx:My:Mz obtained 2 hours after the dropwise addition was started, the factors Fx, Fy and Fz were calculated according to Fx=Px/Mx, Fy=Py/My and Fz=Pz/Mz, to find that Fx=1.27, Fy=0.76, and Fz=1.22. Here, since Fy<Fz<Fx, Fy was substituted by 0.

The above factor and target composition ratio were used to find a composition ratio of Uc $x_0$:$y_0$:$z_0$.

$x_0$=40×$Fx$/(40×$Fx$+40×$Fy$+20×$Fz$)=40×1.27/(40×1.27+40×0+20×1.22)=67.6 mol %.

$y_0$=40×$Fy$/(40×$Fx$+40×$Fy$+20×$Fz$)=40×0/(40×1.27+40×0+20×1.22)=0 mol %.

$z_0$=20×$Fz$/(40×$Fx$+40×$Fy$+20×$Fz$)=20×1.22/(40×1.27+40×0+20×1.22)=32.4 mol %.

Example B-1

In the present example, the reactor was charged with the solution Sa (may simply be referred to as Sa herein; the same applies to solutions Tb and Uc) in advance, and the later step of adding Uc dropwise was provided after the main step of adding Tb and the polymerization initiator solution dropwise.

The composition ratio obtained in Reference Example B-1 was used. The type of monomer, type of polymerization initiator, polymerization temperature, target composition ratio of the polymer and target value of the weight-average molecular weight in use are the same as those in Reference Example B-1. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-1 (Fx=1.27, Fy=0.76, Fz=1.22) and the target composition, and was used as the monomer composition ratio of Sa.

$x_{00}$=40/$Fx$=40/1.27=approx. 31.3 mol %

$y_{00}$=40/$Fy$=40/0.76=approx. 52.4 mol %

$z_{00}$=20/$Fz$=20/1.22=approx. 16.3 mol %

A flask equipped with a nitrogen introduction port, a stirrer, a condenser, two dropping funnels and a temperature gauge was charged with the following Sa (S1) in a nitrogen atmosphere. The flask was bathed. Then, the temperature of the bath was raised to 80° C. while stirring the content in the flask.

Thereafter, feeding of the following Tb (T1) and the polymerization initiator solution was started simultaneously from separate dropping funnels, and Tb was added dropwise over 4 hours and the polymerization initiator solution was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. After 7 hours passed since the dropwise addition of Tb was started, the flask was cooled to ambient temperature to stop the reaction.

In the present example, the total amount of monomers contained in Uc is 2.15 mass % of the total feed amount of monomers.

(Sa)
  Monomer m-1: 3.99 parts (31.3 mol %);
  Monomer m-2: 7.68 parts (52.4 mol %);
  Monomer m-3: 2.88 parts (16.3 mol %); and
  Ethyl lactate: 99.3 parts.
(Tb)
  Monomer m-1: 24.03 parts (40 mol %);
  Monomer m-2: 27.71 parts (40 mol %);

Monomer m-3: 16.68 parts (20 mol %);
Ethyl lactate: 101.8 parts; and
Dimethyl-2,2'-azobisisobutylate: 0.690 parts (0.7 mol % of the total amount of the monomers in Sa and Tb).
(Polymerization Initiator Solution)
Ethyl lactate: 2.0 parts; and
Dimethyl-2,2'-azobisisobutylate: 1.280 parts (1.3 mol % of the total amount of the monomers in Sa and Tb).
(Uc)
Monomer m-1: 1.09 parts (67.6 mol %);
Monomer m-3: 0.73 parts (32.4 mol %);
Ethyl lactate: 34.5 parts; and
Dimethyl-2,2'-azobisisobutylate: 0.054 parts (2.5 mol % of the total amount of the monomers in Uc).

The content ratio (polymer composition ratio) of the monomer units of a polymer produced in each reaction time was determined by the same process as in Reference Example B-1.

Figure 6:
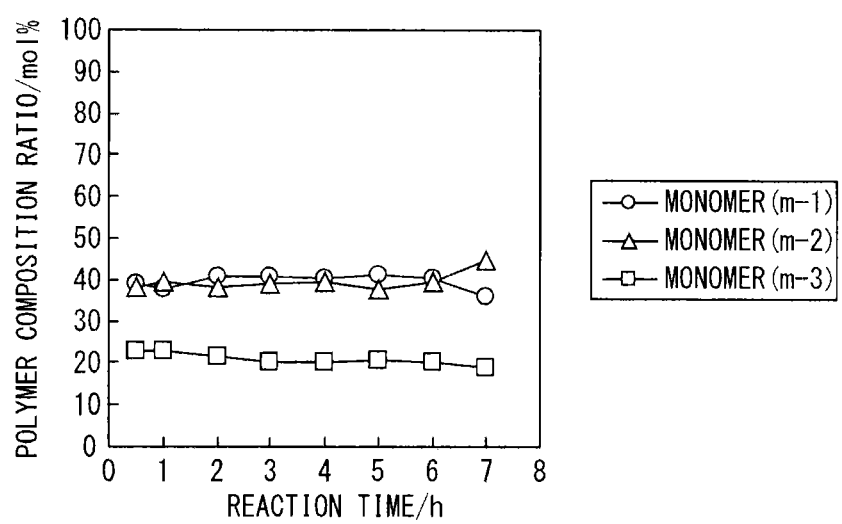
FIG. 6 is a chart showing results of Example B-1.

The results are shown in FIG. 6. Comparing results of FIGS. 5 and 6, in Reference Example B-1 (FIG. 5), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-2 (FIG. 6), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.

(Refining of a Polymer)

After the reaction was continued for 7 hours, the flask was cooled to ambient temperature to terminate the reaction. Then, the polymerization reaction solution in the flask was added dropwise to a mixture solvent of methanol and water (methanol/water=80/20 ratio by volume) having a volume approximately ten times that of the reaction solution while stirring to obtain a white precipitate (polymer P1). The precipitate was separated by filtration. Then, the separated precipitate was again poured into a mixture solvent of methanol and water (methanol/water=90/10 ratio by volume) having the same amount as above. Then, the mixture was washed while stirring. Then, the washed precipitate was separated by filtration to obtain 160 g of a wet polymer powder. Subsequently, 10 g of the wet polymer powder was dried at 40° C. under reduced pressure for about 40 hours. Mw and Mw/Mn of the obtained polymer P1 were determined. Also, the solubility of the polymer P1 was evaluated. The results are shown in Table 20.

(Production of a Resist Composition)

The rest of the above wet polymer powder was poured into 880 g of PGMEA. Then, the above wet polymer powder was completely dissolved to obtain a polymer solution. This polymer solution was passed through a nylon filter (trade name: P-NYLON N66FILTER 0.04M, manufactured by Nihon Pall Ltd.) having a pore size of 0.04 μm to filter the polymer solution.

The obtained polymer solution was heated under reduced pressure to distill methanol and water. Further, PGMEA was distilled from the polymer solution. A polymer P1 solution was thus obtained. The concentration of the polymer in the polymer P1 solution was 25% by mass. In this case, the maximum ultimate vacuum was 0.7 kPa. The maximum solution temperature was 65° C. Also, the time required for distillation was 8 hours.

400 parts of the obtained polymer P1 solution, 2 parts of triphenylsulfonium triflate provided as a photoacid generator and PGMEA provided as a solvent were mixed such that the concentration of the polymer was 12.5% by mass to obtain a homogeneous solution. This solution was then subjected to filtration using a membrane filter having a pore size of 0.1 μm to obtain a resist composition. The sensitivity of the obtained resist composition was evaluated by the above method. The results are shown in Table 20.

Comparative Example B-1

The total amount of monomers contained in Uc added dropwise in the late step in Example B-1 was changed to 14.9 mass % of the total feed amount of monomers.

In other words, the same process as Example B-1 was conducted, except for changing the composition ratios of Sa to Uc and the polymerization initiator solution were changed as follows.
(Sa)
Monomer m-1: 3.99 parts (31.3 mol %);
Monomer m-2: 7.68 parts (52.4 mol %);
Monomer m-3: 2.88 parts (16.3 mol %); and
Ethyl lactate: 99.3 parts.
(Tb)
Monomer m-1: 24.03 parts (40 mol %);
Monomer m-2: 27.71 parts (40 mol %);
Monomer m-3: 16.68 parts (20 mol %);
Ethyl lactate: 101.8 parts; and
Dimethyl-2,2'-azobisisobutylate: 0.690 parts (0.7 mol % of the total amount of the monomers in Sa and Tb).
(Polymerization Initiator Solution)
Ethyl lactate: 2.0 parts; and
Dimethyl-2,2'-azobisisobutylate: 1.280 parts (1.3 mol % of the total amount of the monomers in Sa and Tb).
(Uc)
Monomer m-1: 8.72 parts (67.6 mol %);
Monomer m-3: 5.84 parts (32.4 mol %); and
Ethyl lactate: 34.5 parts; and
Dimethyl-2,2'-azobisisobutylate: 0.432 parts (2.5 mol % of the total amount of the monomers in Uc).

Figure 7:
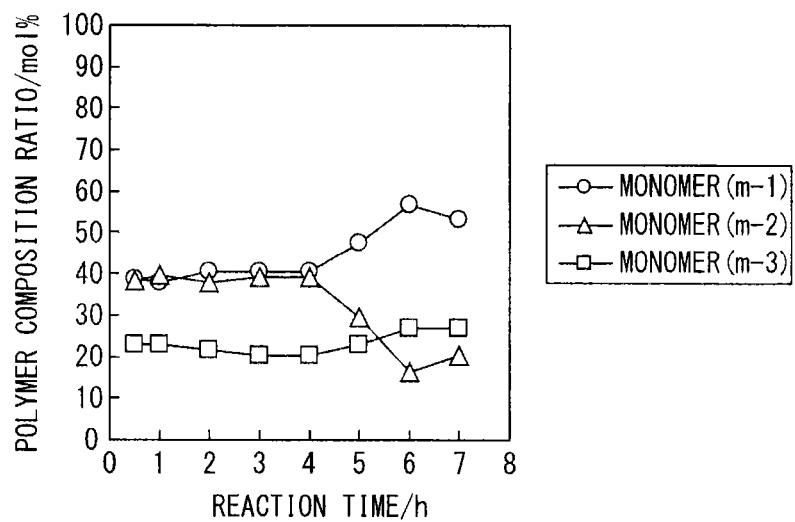
FIG. 7 is a chart showing results of Comparative Example B-1.

The content ratio (polymer composition ratio) of the monomer units of a polymer produced in each reaction time was determined by the same process as in Reference Example B-1. The results are shown in FIG. 7.

Compared to Example B-1 (FIG. 6), proportion of monomers fed in the later step to the total feed amount of monomers is too large in Comparative Example B-1 (FIG. 7), there is a substantial difference between the polymer composition ratio of a polymer formed after completion of the main step (reaction time: 4 hours) and the target composition ratio. In addition, there is a large variation in the polymer composition ratio according to the reaction time. Mw and Mw/Mn of the obtained polymer were determined. Also, the solubility of the polymer was evaluated. The results are shown in Table 20.

Reference Example B-2: Design of Composition of a Solution Uc Used in the Later Step In this example, a composition of Uc was determined in the case of polymerizing monomers m-4, m-5 and m-3 represented by the above formulae (m-4), (m-5) and (m-3) respectively to produce a polymer so designed that its target composition ratio was m-4:m-5:m-3=35:35:30 (mol %) and its target value of weight-average molecular weight was 7,000.

The polymerization initiator used in the present invention was dimethyl-2,2'-azobisisobutylate which was the same as that which was used in Reference Example B-1. The polymerization temperature was set to 80° C.

A flask equipped with a nitrogen introduction port, a stirrer, a condenser, a dropping funnel, and a temperature gauge was charged with 31.7 parts of ethyl lactate and 31.7 parts of PGMEA in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.

Monomer m-4: 20.83 parts (35 mol %);
Monomer m-5: 30.38 parts (35 mol %);
Monomer m-3: 24.78 parts (30 mol %);
Ethyl lactate: 57.0 parts;
PGMEA: 57.0 parts; and
Dimethyl-2,2'-azobisisobutylate: 4.508 parts (5.6 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-3 to m-5 were respectively measured quantitatively. Thus, the mass of each monomer left in a flask in each sampling is determined. As a result, for example, the results obtained 3 hours and 4 hours after the dropwise addition is started are shown in Table 10.

TABLE 10

|  | After 3 hours (parts by mass) | After 4 hours (parts by mass) |
| --- | --- | --- |
| Monomer m-4 (Mx) | 3.57 | 3.82 |
| Monomer m-5 (My) | 12.80 | 14.60 |
| Monomer m-3 (Mz) | 4.10 | 4.41 |

Then, the mass of each monomer was converted into the molar ratio (corresponding to Mx:My:Mz) of each monomer left in a flask at each time of sampling by using the molecular weight of each monomer.

As a result, for example, the results obtained 3 hours and 4 hours after the dropwise addition is started are shown in Table 11.

TABLE 11

|  | After 3 hours (mol %) | After 4 hours (mol %) |
| --- | --- | --- |
| Monomer m-4 (Mx) | 23.35 | 22.45 |
| Monomer m-5 (My) | 57.35 | 58.88 |
| Monomer m-3 (Mz) | 19.30 | 18.67 |

The content ratio of the monomer units of a polymer produced in each reaction time was determined by the same process as in Reference Example B-1. The results are shown in FIG. 8.

Figure 8:
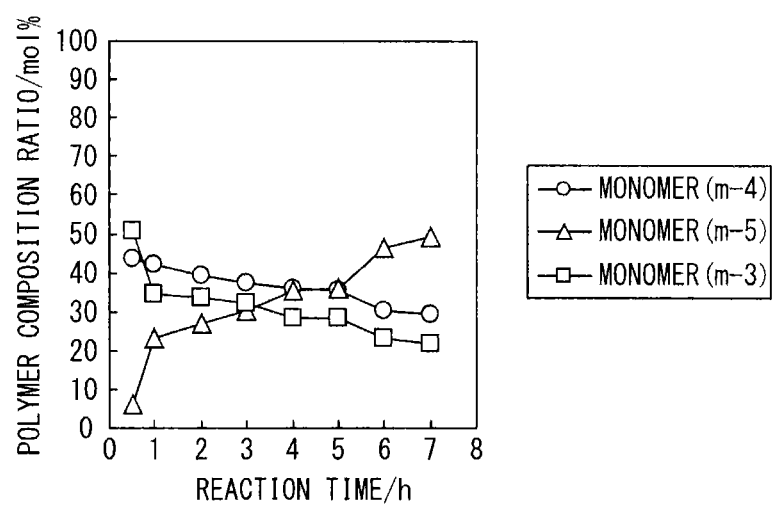
FIG. 8 is a chart showing results of Reference Example B-2.

As shown by the results in FIG. 8, the polymer composition ratio (Px:Py:Pz) in a polymer produced 3 hours to 4 hours after the dropwise addition was started was closest to the target composition ratio 35:35:30. The value of the polymer composition ratio was as follows: Px:Py:Pz=37.36:32.61:28.95.

Using this value and the value (Table 11) Mx:My:Mz obtained 3 hours after the dropwise addition was started, the factors Fx, Fy and Fz were calculated according to Fx=Px/Mx, Fy=Py/My and Fz=Pz/Mz, to find that Fx=1.60, Fy=0.60, and Fz=1.50. Here, since Fy<Fz<Fx, Fy was substituted by 0.

The above factor and target composition ratio were used to find a composition ratio of Uc $x_0{:}y_0{:}z_0$.

$x_0 = 35 \times Fx/(35 \times Fx + 35 \times Fy + 30 \times Fz) = 35 \times 1.60/(35 \times 1.60 + 35 \times 0 + 30 \times 1.50) = 55.4$ mol %.

$y_0 = 35 \times Fy/(35 \times Fx + 35 \times Fy + 30 \times Fz) = 35 \times 0/(35 \times 1.60 + 35 \times 0 + 30 \times 1.50) = 0$ mol %.

$z_0 = 30 \times Fy/(35 \times Fx + 35 \times Fy + 30 \times Fz) = 30 \times 1.50/(35 \times 1.60 + 35 \times 0 + 30 \times 1.50) = 44.6$ mol %.

Example B-2

In the present example, the reactor was charged with the solution Sa in advance, and the later step of adding Uc dropwise was provided after the main step of adding Tb and the polymerization initiator solution dropwise.

The composition ratio obtained in Reference Example B-2 was used. The type of monomer, type of polymerization initiator, polymerization temperature, target composition ratio of the polymer and target value of the weight-average molecular weight in use are the same as those in Reference Example B-2. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-2 (Fx=1.60, Fy=0.60, Fz=1.50) and the target composition, and was used as the monomer composition ratio of Sa.

$x_{00} = 35/Fx = 35/1.60 =$ approx. 21.8 mol %

$y_{00} = 35/Fy = 35/0.60 =$ approx. 58.2 mol %

$z_{00} = 30/Fz = 30/1.50 =$ approx. 20.0 mol %

A flask equipped with a nitrogen introduction port, a stirrer, a condenser, two dropping funnels and a temperature gauge was charged with the following Sa (S1) in a nitrogen atmosphere. The flask was bathed. Then, the temperature of the bath was raised to 80° C. while stirring the content in the flask.

Thereafter, feeding of the following Tb (T1) and the polymerization initiator solution was started simultaneously from separate dropping funnels, and Tb was added dropwise over 4 hours and the polymerization initiator solution was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. The flask was cooled to ambient temperature to terminate the reaction 7 hours after the dropwise addition of Tb solution was started.

In the present example, the total amount of monomers contained in Uc is 2.68 mass % of the total feed amount of monomers.

(Sa)
 Monomer m-4: 2.60 parts (21.8 mol %);
 Monomer m-5: 10.13 parts (58.2 mol %);
 Monomer m-3: 3.30 parts (20.0 mol %);
 Ethyl lactate: 46.5 parts; and
 PGMEA: 46.5 parts.

(Tb)
 Monomer m-4: 16.66 parts (35 mol %);
 Monomer m-5: 24.30 parts (35 mol %);
 Monomer m-3: 24.00 parts (30 mol %);
 Ethyl lactate: 26.9 parts;
 PGMEA: 33.4 parts; and
 Dimethyl-2,2'-azobisisobutylate: 1.450 parts (1.8 mol % of the total amount of the monomers in Sa and Tb).

(Polymerization Initiator Solution)
 Ethyl lactate: 6.5 parts;
 Dimethyl-2,2'-azobisisobutylate: 2.174 parts (2.7 mol % of the total amount of the monomers in Sa and Tb).

(Uc)
 Monomer m-4: 1.00 parts (55.4 mol %);
 Monomer m-3: 1.12 parts (44.6 mol %);
 Ethyl lactate: 12.2 parts;
 PGMEA: 12.2 parts; and
 Dimethyl-2,2'-azobisisobutylate: 0.110 parts (4.5 mol % of the total amount of the monomers in Uc).

The content ratio (polymer composition ratio) of the monomer units of a polymer produced in each reaction time was determined by the same process as in Reference Example B-1. The results are shown in FIG. 9.

Figure 9:
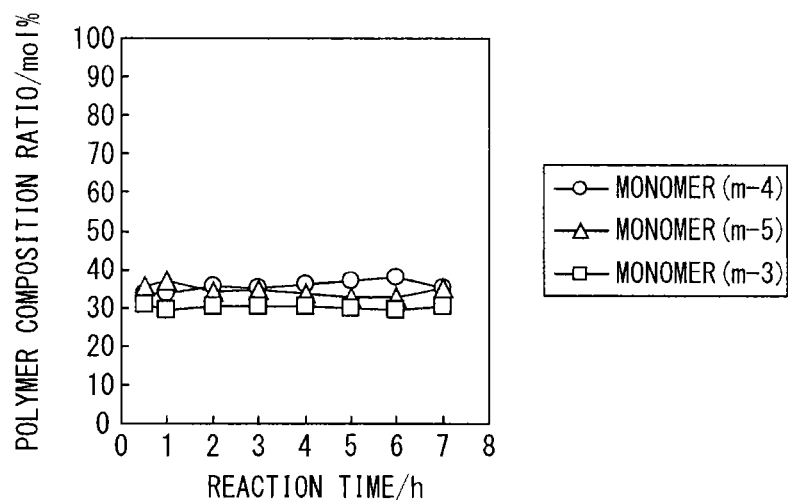
FIG. 9 is a chart showing results of Example B-2.

Comparing results of FIGS. 8 and 9, in Reference Example B-2 (FIG. 8), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-2 (FIG. 9), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.

(Refining of a Polymer)

The mixture solvent of methanol and water (methanol/water=80/20 volume ratio) and (methanol/water=90/10 volume ratio) were altered to a mixture solvent of methanol and water (methanol/water=85/15 volume ratio) and (methanol/water=95/5 volume ratio) respectively. A polymer P2 was obtained from the polymerization reaction solution in the flask after the reaction was continued for 7 hours by the same procedures as in Example B-1 except for the above alteration. Mw and Mw/Mn of the polymer P2 and the results of evaluation of solubility are shown in Table 20.

(Production of a Resist Composition)

A resist composition containing the polymer P2 was prepared by the same procedures as in Example B-1. Then, the sensitivity of the resist composition was evaluated. The results are shown in Table 20.

Reference Example B-3: Design of Composition of a Solution Uc Used in the Later Step In this example, a composition of Uc was determined in the case of polymerizing monomers m-1, m-6 and m-7 represented by the above formula (m-1) and the following formulae (m-6) and (m-7) respectively to produce a polymer so designed that its target composition ratio was m-1:m-6:m-7=25:25:50 (mol %) and its target value of weight-average molecular weight was 10,000.

The polymerization initiator used in the present invention was dimethyl-2,2'-azobisisobutylate which was the same as that which was used in Reference Example B-1. The polymerization temperature was set to 80° C.

[Chemical Formula 5]

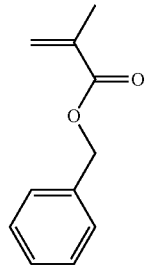

(m-6)

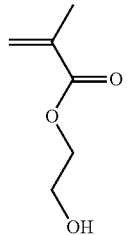

(m-7)

A flask equipped with a nitrogen introduction port, a stirrer, a condenser, a dropping funnel and a temperature gauge was charged with 129.1 parts of PGME in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.

Monomer m-1: 25.95 parts (25 mol %);
 Monomer m-6: 26.87 parts (25 mol %);
 Monomer m-7: 39.65 parts (50 mol %);
 PGME: 92.5 parts; and
 Dimethyl-2,2'-azobisisobutylate: 9.130 parts (6.5 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-1, m-6, and m-7 were respectively measured quantitatively. Thus, the mass of each monomer left in a flask is determined. As a result, for example, the results obtained 3 hours and 4 hours after the dropwise addition is started are shown in Table 12.

TABLE 12

|  | After 3 hours (parts by mass) | After 4 hours (parts by mass) |
|---|---|---|
| Monomer m-1 (Mx) | 1.72 | 1.66 |
| Monomer m-6 (My) | 2.38 | 2.39 |
| Monomer m-7 (Mz) | 4.03 | 4.14 |

Then, the mass of each monomer was converted into the molar ratio (corresponding to Mx:My:Mz) of each monomer left in a flask at each time of sampling by using the molecular weight of each monomer.

As a result, for example, the results obtained 3 hours and 4 hours after the dropwise addition is started are shown in Table 13.

TABLE 13

|  | After 3 hours (mol %) | After 4 hours (mol %) |
|---|---|---|
| Monomer m-1 (Mx) | 18.71 | 18.10 |
| Monomer m-6 (My) | 26.16 | 26.25 |
| Monomer m-7 (Mz) | 55.13 | 56.65 |

The content ratio of the monomer units (polymer composition ratio) of a polymer produced in each reaction time was determined by the same process as in Reference Example B-1. The results are shown in FIG. 10.

Figure 10:
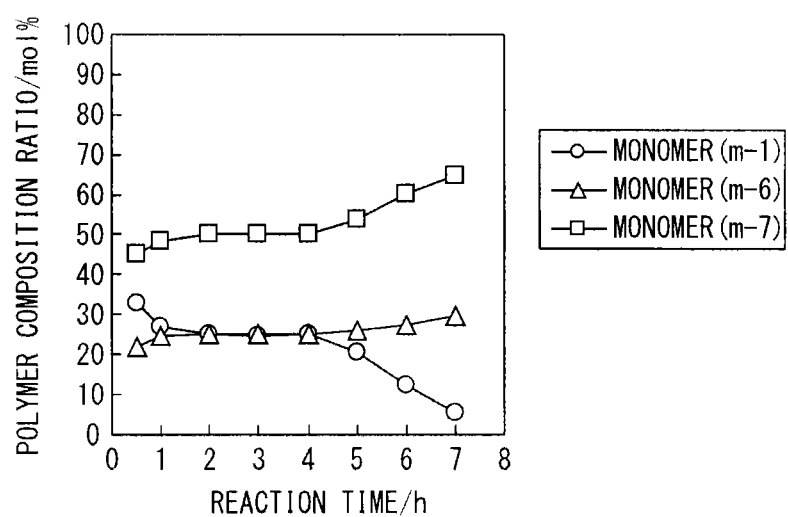
FIG. 10 is a chart showing results of Reference Example B-3.

As shown by the results in FIG. 10, the polymer composition ratio (Px:Py:Pz) in a polymer produced 3 hours to 4 hours after the dropwise addition was started was closest to the target composition ratio 25:25:50. The value of the polymer composition ratio was as follows: Px:Py:Pz=24.32:23.54:46.86.

Using this value and the value (Table 13) Mx:My:Mz obtained 3 hours after the dropwise addition was started, the factors Fx, Fy and Fz were calculated according to Fx=Px/Mx, Fy=Py/My and Fz=Fz/Mz, to find that Fx=1.30, Fy=0.90, and Fz=0.85. Here, since Fz<Fy<Fx, Fz was substituted by 0.

The above factor and target composition ratio were used to find a composition ratio of Uc $x_0:y_0:z_0$.

$x_0=25 \times Fx/(25 \times Fx+25 \times Fy+50 \times Fz)=25 \times 1.30/(25 \times 1.30+25 \times 0.90+50 \times 0)=59.1$ mol %.

$y_0=25 \times Fy/(25 \times Fx+25 \times Fy+50 \times Fz)=25 \times 0.90/(25 \times 1.30+25 \times 0.90+50 \times 0)=40.9$ mol %.

$z_0=50 \times Fz/(25 \times Fx+25 \times Fy+50 \times Fz)=50 \times 0/(25 \times 1.30+25 \times 0.90+50 \times 0)=0$ mol %.

Example B-3

In the present example, the reactor was charged with the solution Sa in advance, and the later step of adding Uc dropwise was provided after the main step of adding Tb and the polymerization initiator solution dropwise.

The composition ratio obtained in Reference Example B-3 was used. The type of monomer, type of polymerization initiator, polymerization temperature, target composition ratio of the polymer and target value of the weight-average molecular weight in use are the same as those in Reference Example B-3. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-3 (Fx=1.30, Fy=0.90, Fz=0.85) and the target composition, and was used as the monomer composition ratio of Sa.

$x_{00}=25/Fx=25/1.30=19.2$ mol %

$y_{00}=25/Fy=25/0.90=27.8$ mol %

$z_{00}=50/Fz=50/0.85=58.8$ mol %

A flask equipped with a nitrogen introduction port, a stirrer, a condenser, two dropping funnels and a temperature gauge was charged with the following Sa (S1) in a nitrogen atmosphere. The flask was bathed. Then, the temperature of the bath was raised to 80° C. while stirring the content in the flask.

Thereafter, feeding of the following Tb (T1) and the polymerization initiator was started simultaneously from separate dropping funnels, and Tb was added dropwise over 4 hours and the polymerization initiator was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. The flask was cooled to ambient temperature to terminate the reaction 7 hours after the dropwise addition of Tb solution was started.

In the present example, the total amount of monomers contained in Uc is 1.99 mass % of the total feed amount of monomers.

(Sa)
  Monomer m-1: 2.00 parts (18.2 mol %);
  Monomer m-6: 2.99 parts (26.2 mol %);
  Monomer m-7: 4.74 parts (55.6 mol %);
and PGME: 139.0 parts.
(Tb)
  Monomer m-1: 23.36 parts (25 mol %);
  Monomer m-6: 24.19 parts (25 mol %);
  Monomer m-7: 39.57 parts (50 mol %);
  PGME: 44.5 parts; and
  Dimethyl-2,2'-azobisisobutylate: 2.815 parts (2.0 mol % of the total amount of the monomers in Sa and Tb).
(Polymerization Initiator Solution)
  and PGME: 5.2 parts.
  Dimethyl-2,2'-azobisisobutylate: 4.223 parts (3.0 mol % of the total amount of the monomers in Sa and Tb).
(Uc)
  Monomer m-1: 1.25 parts (59.1 mol %);
  Monomer m-6: 0.73 parts (40.9 mol %);
  and PGME: 37.5 parts.
  Dimethyl-2,2'-azobisisobutylate: 0.132 parts (5.0 mol % of the total amount of the monomers in Uc).

The content ratio (polymer composition ratio) of the monomer units of a polymer produced in each reaction time was determined by the same process as in Reference Example B-1. The results are shown in FIG. 11.

Figure 11:
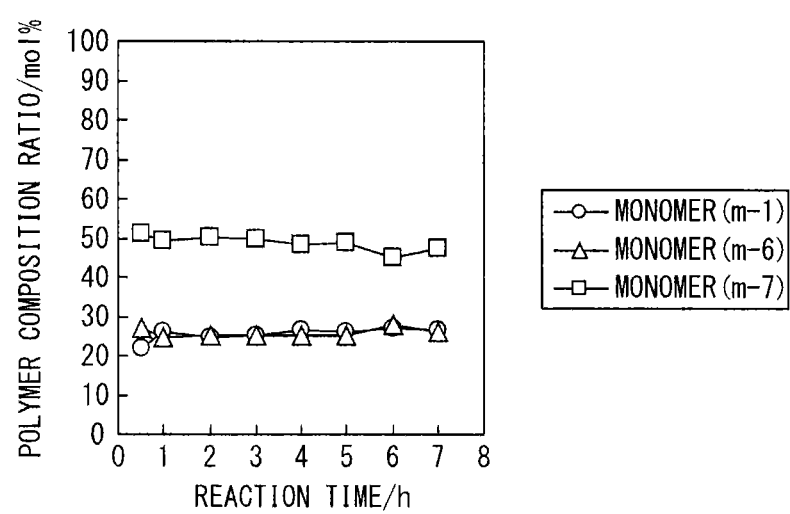
FIG. 11 is a chart showing results of Example B-3.

Comparing results of FIGS. 10 and 11, in Reference Example B-3 (FIG. 10), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-3 (FIG. 11), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.
(Refining of a Polymer)

The mixture solvent of methanol and water (methanol/water=80/20 volume ratio) and (methanol/water=90/10 volume ratio) were both altered to diisopropylether. A polymer P3 was obtained from the polymerization reaction solution in the flask after the reaction was continued for 7 hours by the same procedures as in Example B-1 except for the above alteration. Mw and Mw/Mn, and also the solubility of the polymer P3 were evaluated. The results are shown in Table 21.

Reference Example B-4: Design of Composition of a Solution Uc Used in the Later Step In this example, a composition of Uc was determined in the case of polymerizing monomers m-8, m-9 and m-10 represented by the following formulae (m-8), (m-9) and (m-10) respectively to produce a polymer so designed that its target composition ratio was m-8: m-9: m-10=30:50:20 (mol %) and its target value of weight-average molecular weight was 12,000.

The polymerization initiator used in the present invention was dimethyl-2,2'-azobisisobutylate which was the same as that which was used in Reference Example B-1. The polymerization temperature was set to 80° C.

[Chemical Formula 6]

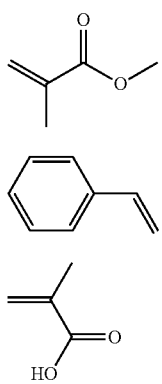

A flask equipped with a nitrogen introduction port, a stirrer, a condenser, a dropping funnel and a temperature gauge was charged with 82.8 parts of PGMEA in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.

Monomer m-8: 30.04 parts (30 mol %);
Monomer m-9: 52.08 parts (50 mol %);
Monomer m-10: 17.22 parts (20 mol %);
PGMEA: 149.0 parts; and
Dimethyl-2,2'-azobisisobutylate: 11.50 parts (5.0 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-8, m-9, and m-10 were respectively measured quantitatively. Thus, the mass of each monomer left in a flask was determined. As a result, for example, the results obtained 3 hours and 4 hours after the dropwise addition was started are shown in Table 14.

TABLE 14

|  | After 3 hours (parts by mass) | After 4 hours (parts by mass) |
| --- | --- | --- |
| Monomer m-8 (Mx) | 5.25 | 2.77 |
| Monomer m-9 (My) | 8.73 | 4.01 |
| Monomer m-10 (Mz) | 3.83 | 2.55 |

Then, the mass of each monomer was converted into the molar ratio (corresponding to Mx:My:Mz) of each monomer left in a flask at each time of sampling by using the molecular weight of each monomer.

As a result, for example, the results obtained 3 hours and 4 hours after the dropwise addition was started are shown in Table 15.

TABLE 15

|  | After 3 hours (mol %) | After 4 hours (mol %) |
| --- | --- | --- |
| Monomer m-8 (Mx) | 29.00 | 28.67 |
| Monomer m-9 (My) | 46.38 | 40.65 |
| Monomer m-10 (Mz) | 24.61 | 30.67 |

The content ratio of the monomer units (polymer composition ratio) of a polymer produced in each reaction time was determined by the same process as in Reference Example B-1. The results are shown in Table 12.

Figure 12:
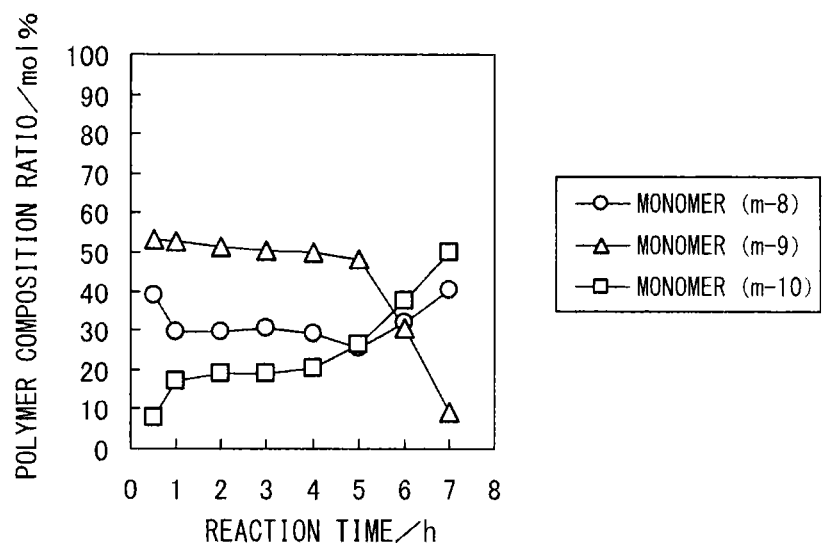
FIG. 12 is a chart showing results of Reference Example B-4.

As shown by the results in FIG. 12, the polymer composition ratio (Px:Py:Pz) in a polymer produced 3 hours to 4 hours after the dropwise addition was started was closest to the target composition ratio 30:50:20. The value of the polymer composition ratio was as follows: Px:Py:Pz=29.22:50.23:20.55.

Using this value and the value (Table 15) Mx:My:Mz obtained 3 hours after the dropwise addition was started, the factors Fx, Fy and Fz were calculated according to Fx=Px/Mx, Fy=Py/My and Fz=Pz/Mz, to find that Fx=1.01, Fy=1.08, and Fz=0.84. Here, since Fz<Fx<Fy, Fz was substituted by 0.

The above factor and target composition ratio were used to find a composition ratio of Uc $x_0$:$y_0$:$z_0$.

$$x_0=30 \times Fx/(30 \times Fx+50 \times Fy+20 \times Fz)=30 \times 1.01/(30 \times 1.01+50 \times 1.08+20 \times 0)=35.9 \text{ mol \%}.$$

$y_0=50\times Fy/(25\times Fx+25\times Fy+50\times Fz)=50\times1.08/(30\times1.01+50\times1.08+20\times0)=64.1$ mol %.

$z_0=20\times Fz/(25\times Fx+25\times Fy+50\times Fz)=20\times0/(30\times1.01+50\times1.08+20\times0)=0$ mol %.

Example B-4

In the present example, the reactor was charged with a solution containing a part of monomers in the Sa composition in advance, and the later step of adding Uc dropwise was provided after the main step of adding Tb and a solution containing the rest of monomers in the Sa composition and the polymerization initiator dropwise.

The composition ratio obtained in Reference Example B-4 was used. The type of monomer, type of polymerization initiator, polymerization temperature, target composition ratio of the polymer and target value of the weight-average molecular weight in use are the same as those in Reference Example B-4. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-4 (Fx=1.01, Fy=1.08, Fz=0.84) and the target composition, and was used as the monomer composition ratio of Sa.

$x_{00}=30/Fx=30/1.01=29.7$ mol %

$y_{00}=50/Fy=50/1.08=46.3$ mol %

$z_{00}=20/Fz=20/0.84=23.8$ mol %

A flask equipped with a nitrogen introduction port, a stirrer, a condenser, two dropping funnels and a temperature gauge was charged with a part of the following Sa (S1) in a nitrogen atmosphere. The flask was bathed. Then, the temperature of the bath was raised to 80° C. while stirring the content in the flask.

Thereafter, feeding of the following Tb (T1) and a solution containing the rest of Sa (S2) and the polymerization initiator was started simultaneously from separate dropping funnels, and Tb was added dropwise over 4 hours and the rest of Sa as well as the polymerization initiator was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. The flask was cooled to ambient temperature to terminate the reaction 7 hours after the dropwise addition of Tb solution was started.

In the present example, the total amount of monomers contained in Uc is 1.7 mass % of the total feed amount of monomers.

(Solution Containing a Part of Monomers in the Sa Composition)

Monomer m-8: 2.97 parts (29.7 mol %);
Monomer m-9: 4.82 parts (46.3 mol %);
PGMEA: 101.5 parts.

(Tb)

Monomer m-8: 27.03 parts (30 mol %);
Monomer m-9: 46.87 parts (50 mol %);
Monomer m-10: 15.50 parts (20 mol %);
PGMEA: 99.3 parts; and
Dimethyl-2,2'-azobisisobutylate: 4.599 parts (2.0 mol % of the total amount of the monomers in Sa and Tb).

(Solution Containing the Rest of Monomers in the Sa Composition and Polymerization Initiator)

PGMEA: 10.7 parts;
Monomer m-10: 2.05 parts (23.8 mol %); and
Dimethyl-2,2'-azobisisobutylate: 4.599 parts (2.0 mol % of the total amount of the monomers in Sa and Tb).

(Uc)

Monomer m-8: 0.61 parts (35.9 mol %);
Monomer m-9: 1.12 parts (64.1 mol %);
PGMEA: 24.0 parts; and
Dimethyl-2,2'-azobisisobutylate: 0.144 parts (4.0 mol % of the total amount of the monomers in Uc).

The content ratio (polymer composition ratio) of the monomer units of a polymer produced in each reaction time was determined by the same process as in Reference Example B-1. The results are shown in FIG. 13.

Figure 13:
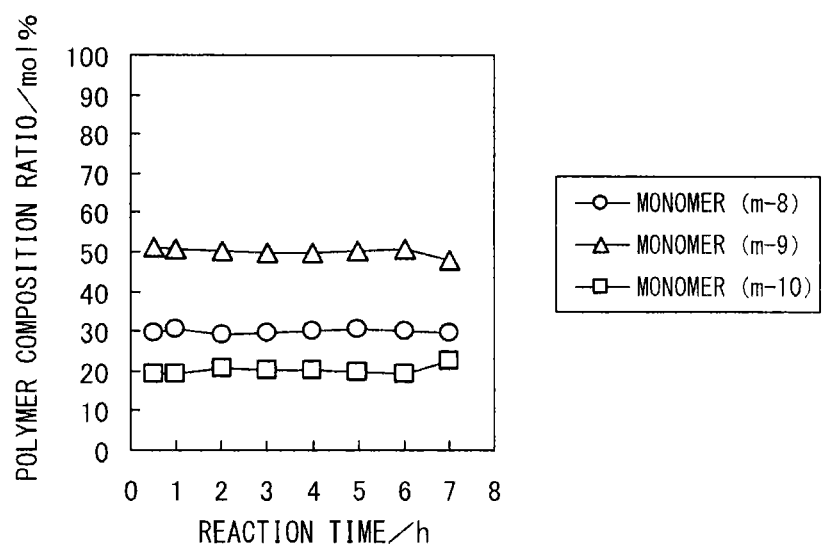
FIG. 13 is a chart showing results of Example B-4.

Comparing results of FIGS. 12 and 13, in Reference Example B-4 (FIG. 12), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-4 (FIG. 13), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.

(Refining of a Polymer)

The mixture solvent of methanol and water (methanol/water-80/20 volume ratio) and (methanol/water-90/10 volume ratio) were altered to a mixture solvent of methanol and water (methanol/water-50/50 volume ratio) and (methanol/water-60/40 volume ratio) respectively. A polymer P4 was obtained from the polymerization reaction solution in the flask after the reaction was continued for 7 hours by the same procedures as in Example B-1 except for the above alteration. Mw and Mw/Mn, and also the solubility of the polymer P4 were evaluated. The results are shown in Table 21.

Reference Example B-5: Design of Composition of a Solution Uc Used in the Later Step In this example, a composition of Uc was determined in the case of polymerizing monomers m-1, m-11 and m-12 represented by the above formula (m-1) and the following formulae (m-11) and (m-12) respectively to produce a polymer so designed that its target composition ratio was m-1: m-11:m-12=50:35:15 (mol %) and its target value of weight-average molecular weight was 12,000.

The polymerization initiator used in the present invention was dimethyl-2,2'-azobisisobutylate which was the same as that which was used in Reference Example B-1. The polymerization temperature was set to 80° C.

[Chemical Formula 7]

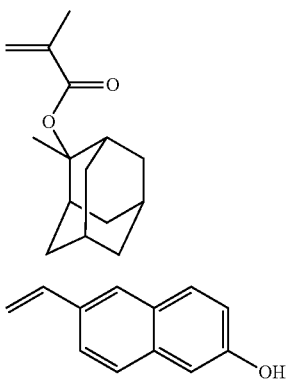

(m-11)

(m-12)

A flask equipped with a nitrogen introduction port, a stirrer, a condenser, a dropping funnel, and a temperature gauge was charged with 160.3 parts of ethyl lactate in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.

Monomer m-1: 85.00 parts (50 mol %);

Monomer m-11: 81.90 parts (35 mol %);

Monomer m-12: 25.50 parts (15 mol %);

Ethyl lactate: 288.6 parts; and

Dimethyl-2,2'-azobisisobutylate: 6.90 parts (3.0 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-1, m-11, and m-12 were respectively measured quantitatively. Thus, the mass of each monomer left in a flask is determined. As a result, for example, the results obtained 3 hours and 4 hours after the dropwise addition is started are shown in Table 16.

TABLE 16

|  | After 3 hours (parts by mass) | After 4 hours (parts by mass) |
| --- | --- | --- |
| Monomer m-1 (Mx) | 26.34 | 16.47 |
| Monomer m-11 (My) | 31.63 | 24.42 |
| Monomer m-12 (Mz) | 5.37 | 1.39 |

Then, the mass of each monomer was converted into the molar ratio (corresponding to Mx:My:Mz) of each monomer left in a flask at each time of sampling by using the molecular weight of each monomer.

As a result, for example, the results obtained 3 hours and 4 hours after the dropwise addition is started are shown in Table 17.

TABLE 17

|  | After 3 hours (mol %) | After 4 hours (mol %) |
| --- | --- | --- |
| Monomer m-1 (Mx) | 48.17 | 46.26 |
| Monomer m-11 (My) | 42.01 | 49.82 |
| Monomer m-12 (Mz) | 9.82 | 3.91 |

The content ratio of the monomer units (polymer composition ratio) of a polymer produced in each reaction time was determined by the same process as in Reference Example B-1. The results are shown in FIG. 14.

Figure 14:
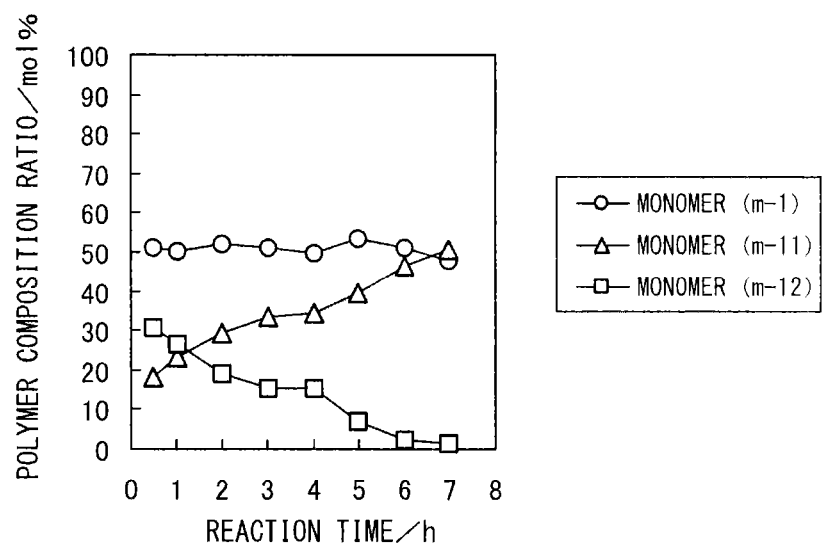
FIG. 14 is a chart showing results of Reference Example B-5.

As shown by the results in FIG. 14, the polymer composition ratio (Px:Py:Pz) in a polymer produced 3 hours to 4 hours after the dropwise addition was started was closest to the target composition ratio 50:35:15. The value of the polymer composition ratio was as follows: Px:Py:Pz=49.99: 34.55:15.45.

Using this value and the value (Table 17) Mx:My:Mz obtained 3 hours after the dropwise addition was started, the factors Fx, Fy and Fz were calculated according to Fx=Px/Mx, Fy=Py/My and Fz=Pz/Mz, to find that Fx=1.04, Fy=0.82, and Fz=1.57. Here, since Fz<Fx<Fy, Fy was substituted by 0.

The above factor and target composition ratio were used to find a composition ratio of Uc $x_0$:$y_0$:$z_0$.

$x_0=50 \times Fx/(50 \times Fx+35 \times Fy+15 \times Fz)=50 \times 1.04/(50 \times 1.04+35 \times 0+15 \times 1.57)=68.8$ mol %

$y_0=35 \times Fy/(50 \times Fx+35 \times Fy+15 \times Fz)=35 \times 0/(50 \times 1.04+35 \times 0+15 \times 1.57)=0$ mol %

$z_0=15 \times Fz/(50 \times Fx+35 \times Fy+15 \times Fz)=15 \times 1.57/(50 \times 1.04+35 \times 0+15 \times 1.57)=31.2$ mol %

Example B-5

In the present example, the reactor was charged with a solution containing monomers in the Sa composition in advance, and the later step of adding Uc dropwise was provided after the main step of adding Tb and the polymerization initiator solution dropwise.

The composition ratio obtained in Reference Example B-5 was used. The type of monomer, type of polymerization initiator, polymerization temperature, target composition ratio of the polymer and target value of the weight-average molecular weight in use are the same as those in Reference Example B-5. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-5 (Fx=1.04, Fy=0.82, Fz=1.57) and the target composition, and was used as the monomer composition ratio of Sa.

$x_{00}=50/Fx=50/1.04=48.1$ mol %

$y_{00}=35/Fy=35/0.82=42.7$ mol %

$z_{00}=15/Fz=15/1.57=9.6$ mol %

A flask equipped with a nitrogen introduction port, a stirrer, a condenser, two dropping funnels and a temperature gauge was charged with the following Sa (S1) in a nitrogen atmosphere. The flask was bathed. Then, the temperature of the bath was raised to 80° C. while stirring the content in the flask.

Thereafter, feeding of the following Tb (T1) and the polymerization initiator was started simultaneously from separate dropping funnels, and Tb was added dropwise over 4 hours and the polymerization initiator was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. The flask was cooled to ambient temperature to terminate the reaction 7 hours after the dropwise addition of Tb solution was started.

In the present example, the total amount of monomers contained in Uc is 1.3 mass % of the total feed amount of monomers.
(Sa)
  Monomer m-1: 8.17 parts (48.1 mol %);
  Monomer m-11: 9.99 parts (42.7 mol %);
  Monomer m-12: 1.62 parts (9.6 mol %); and
  Ethyl lactate: 196.5 parts.
(Tb)
  Monomer m-1: 76.50 parts (50 mol %);
  Monomer m-11: 73.71 parts (35 mol %);
  Monomer m-12: 22.95 parts (15 mol %);
  Ethyl lactate: 218.2 parts; and
  Dimethyl-2,2'-azobisisobutylate: 2.531 parts (1.1 mol % of the total amount of the monomers in Sa and Tb).
(Polymerization Initiator Solution)
  Ethyl lactate: 5.9 parts; and
  Dimethyl-2,2'-azobisisobutylate: 2.531 parts (1.1 mol % of the total amount of the monomers in Sa and Tb).
(Uc)
  Monomer m-1: 1.77 parts (68.8 mol %);
  Monomer m-12: 0.8 parts (31.2 mol %);
  Ethyl lactate: 24.0 parts; and
  Dimethyl-2,2'-azobisisobutylate: 0.076 parts (2.2 mol % of the total amount of the monomers in Uc).

The content ratio (polymer composition ratio) of the monomer units of a polymer produced in each reaction time was determined by the same process as in Reference Example B-1. The results are shown in Table 15.

Figure 15:
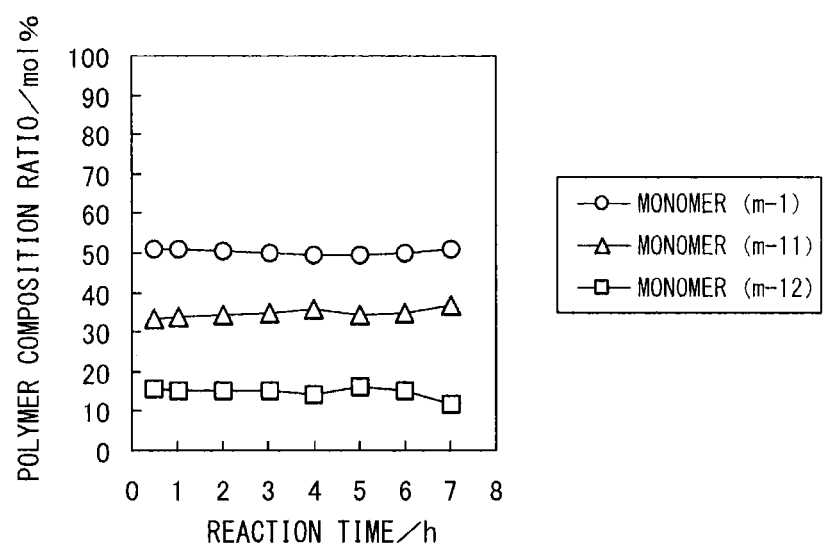
FIG. 15 is a chart showing results of Example B-5.

Comparing results of FIGS. 14 and 15, in Reference Example B-5 (FIG. 14), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-5 (FIG. 15), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.
(Refining of a Polymer)

The mixture solvent of methanol and water (methanol/water=80/20 volume ratio) and (methanol/water-90/10 volume ratio) were altered to a mixture solvent of methanol and water (methanol/water=70/30 volume ratio) and (methanol/water=80/20 volume ratio) respectively. A polymer P5 was obtained from the polymerization reaction solution in the flask after the reaction was continued for 7 hours by the same procedures as in Example B-1 except for the above alteration. Mw and Mw/Mn, and also the solubility of the polymer P5 were evaluated. The results are shown in Table 21.

Reference Example B-6: Design of Composition of a Solution Uc Used in the Later Step In this example, a composition of Uc was determined in the case of polymerizing monomers m-1, m-11 and m-13 represented by the above formula (m-1) and the following formulae (m-11) and (m-13) respectively to produce a polymer so designed that its target composition ratio was m-1:m-11:m-13=50:40:10 (mol %) and its target value of weight-average molecular weight was 7,000.

The polymerization initiator used in the present invention was dimethyl-2,2'-azobisisobutylate which was the same as that which was used in Reference Example B-1. The polymerization temperature was set to 80° C.

[Chemical Formula 8]

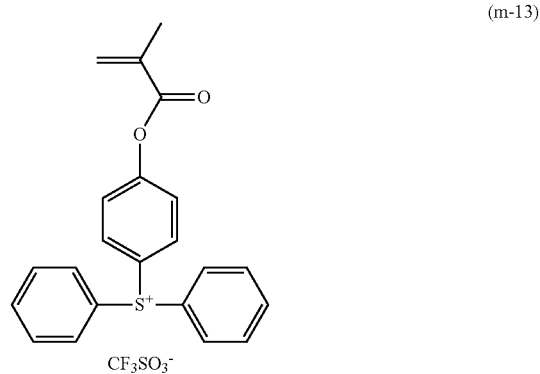

(m-13)

A flask equipped with a nitrogen introduction port, a stirrer, a condenser, a dropping funnel and a temperature gauge was charged with 130.2 parts of PGMEA and 60.0 parts of γ-butyrolactone in a nitrogen atmosphere. The flask was bathed. Then, the temperature of the bath was raised to 80° C. while stirring the content in the flask.

Then, a dropping solution containing the following monomer mixture, a solvent and a polymerization initiator was added dropwise at a fixed dropping rate in the flask by using the dropping funnel over 4 hours. Then, the flask was kept at 80° C. for 3 hours. The flask was cooled to ambient temperature to terminate the reaction 7 hours after the dropwise addition of the dropping solution was started.
  Monomer m-1: 85.00 parts (50 mol %);
  Monomer m-11: 93.60 parts (40 mol %);
  Monomer m-13: 49.60 parts (10 mol %);
  PGMEA: 242.3 parts;
  γ-butyrolactone: 100.0 parts; and
  Dimethyl-2,2'-azobisisobutylate: 4.60 parts (2.0 mol % of the total feed amount of the monomers).

First, 0.5 g of the polymerization reaction solution was sampled at each time when 0.5, 1, 2, 3, 4, 5, 6 and 7 hours passed after the dropwise addition of the above dropping solution was started. Then, the amounts of the monomers m-1, m-11, and m-13 were respectively measured quantitatively. Thus, the mass of each monomer left in a flask is determined. As a result, for example, the results obtained 3 hours and 4 hours after the dropwise addition is started are shown in Table 18.

TABLE 18

|  | After 3 hours (parts by weight) | After 4 hours (parts by weight) |
|---|---|---|
| Monomer m-1 (Mx) | 24.74 | 16.07 |
| Monomer m-11 (My) | 32.07 | 24.40 |
| Monomer m-13 (Mz) | 12.17 | 5.48 |

Then, the mass of each monomer was converted into the molar ratio (corresponding to Mx:My:Mz) of each monomer left in a flask at each time of sampling by using the molecular weight of each monomer.

As a result, for example, the results obtained 3 hours and 4 hours after the dropwise addition is started are shown in Table 19.

TABLE 19

|  | After 3 hours (mol %) | After 4 hours (mol %) |
|---|---|---|
| Monomer m-1 (Mx) | 47.39 | 45.05 |
| Monomer m-11 (My) | 44.62 | 49.69 |
| Monomer m-13 (Mz) | 8.00 | 5.26 |

The content ratio of the monomer units (polymer composition ratio) of a polymer produced in each reaction time was determined by the same process as in Reference Example B-1. The results are shown in Table 16.

Figure 16:
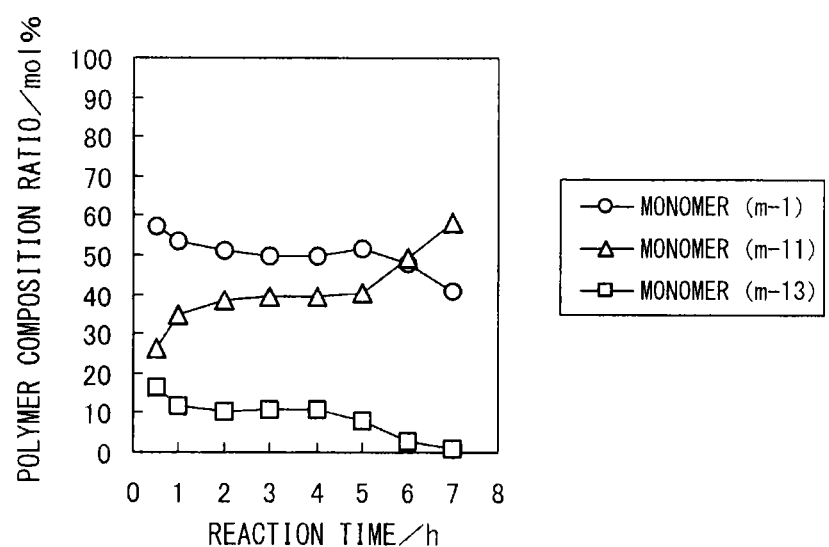
FIG. 16 is a chart showing results of Reference Example B-6.

As shown by the results in FIG. 16, the polymer composition ratio (Px:Py:Pz) in a polymer produced 3 hours to 4 hours after the dropwise addition was started was closest to the target composition ratio 50:40:10. The value of the polymer composition ratio was as follows: Px:Py:Pz=49.85: 39.28:10.87.

Using this value and the value (Table 19) Mx:My:Mz obtained 3 hours after the dropwise addition was started, the factors Fx, Fy and Fz were calculated according to Fx=Px/Mx, Fy=Py/My and Fz=Pz/Mz, to find that Fx=1.05, Fy=0.88, and Fz=1.36. Here, since Fz<Fx<Fy, Fy was substituted by 0.

The above factor and target composition ratio were used to find a composition ratio of Uc $x_0$:$y_0$:$z_0$.

$x_0$=50×$Fx$/(50×$Fx$+40×$Fy$+10×$Fz$)=50×1.05/(50× 1.05+40×0+10×1.36)=79.4 mol %

$y_0$=40×$Fy$/(50×$Fx$+40×$Fy$+10×$Fz$)=40×0/(50×1.05+ 40×0+10×1.36)=0 mol %

$z_0$=10×$Fz$/(50×$Fx$+40×$Fy$+10×$Fz$)=10×1.36/(50× 1.05+40×0+10×1.36)=20.6 mol %

Example B-6

In the present example, the reactor was charged with a solution containing monomers in the Sa composition in advance, and the later step of adding Uc dropwise was provided after the main step of adding Tb and the polymerization initiator solution dropwise.

The composition ratio obtained in Reference Example B-6 was used. The type of monomer, type of polymerization initiator, polymerization temperature, target composition ratio of the polymer and target value of the weight-average molecular weight in use are the same as those in Reference Example B-6. The monomer composition ratio of Sa was the same as the first composition ratio designed by a method using the above factor, and the monomer composition ratio of Tb was the same as the target composition.

(Design of First Composition Ratio of Sa)

The first composition ratio was obtained using the values of factors obtained in Reference Example B-6 (Fx=1.05, Fy=0.88, Fz=1.36) and the target composition, and was used as the monomer composition ratio of Sa.

$x_{00}$=50/$Fx$=50/1.05=approx. 47.6 mol %

$y_{00}$=40/$Fy$=40/0.88=approx. 45.5 mol %

$z_{00}$=10/$Fz$=10/1.36=approx. 7.4 mol %

A flask equipped with a nitrogen introduction port, a stirrer, a condenser, two dropping funnels and a temperature gauge was charged with the following Sa (S1) in a nitrogen atmosphere. The flask was bathed. Then, the temperature of the bath was raised to 80° C. while stirring the content in the flask.

Thereafter, feeding of the following Tb (T1) and the polymerization initiator was started simultaneously from separate dropping funnels, and Tb was added dropwise over 4 hours and the polymerization initiator was added dropwise over 20 minutes to the flask. Furthermore, immediately after completion of feeding of Tb, 80 mass % of Uc (U1) was added dropwise over 1 hour and the remaining 20 mass % (U2) was added dropwise over 1 hour, and the flask was kept at 80° C. for 1 hour. The flask was cooled to ambient temperature to terminate the reaction 7 hours after the dropwise addition of Tb solution was started.

In the present example, the total amount of monomers contained in Uc is 1.3 mass % of the total feed amount of monomers.

(Sa)

Monomer m-1: 8.10 parts (47.6 mol %);
Monomer m-11: 10.64 parts (45.5 mol %);
Monomer m-13: 3.65 parts (7.4 mol %);
PGMEA: 160.7 parts; and
γ-butyrolactone: 70.0 parts.

(Tb)

Monomer m-1: 76.50 parts (50 mol %);
Monomer m-11: 84.24 parts (40 mol %);
Monomer m-13: 44.64 parts (10 mol %);
PGMEA: 187.7 parts; and
γ-butyrolactone: 70.0 parts.
Dimethyl-2,2'-azobisisobutylate: 1.726 parts (0.75 mol % of the total amount of the monomers in Sa and Tb).

(Polymerization Initiator Solution)

PGMEA: 6.9 parts; and
Dimethyl-2,2'-azobisisobutylate: 1.726 parts (0.75 mol % of the total amount of the monomers in Sa and Tb).

(Uc)

Monomer m-1: 1.79 parts (79.4 mol %);
Monomer m-13: 1.35 parts (20.6 mol %);
PGMEA: 33.5 parts;
γ-butyrolactone: 10.0 parts; and
Dimethyl-2,2'-azobisisobutylate: 0.076 parts (2.2 mol % of the total amount of the monomers in Uc).

The content ratio (polymer composition ratio) of the monomer units of a polymer produced in each reaction time was determined by the same process as in Reference Example B-1. The results are shown in Table 17.

Figure 17:
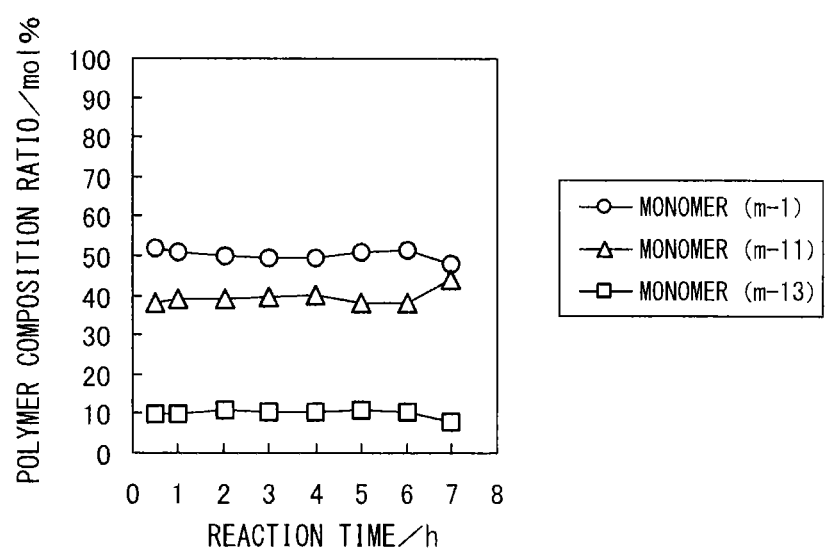
FIG. 17 is a chart showing results of Example B-6.

Comparing results of FIGS. 16 and 17, in Reference Example B-6 (FIG. 16), the polymer composition ratio of a polymer formed in an early stage of the main step is largely different from the target composition ratio. The polymer composition ratio of a polymer formed in a reaction time between 4 hours, corresponding to the end of the main step (end of the dropping solution), and 7 hours, corresponding to the end of the maintaining step, becomes more and more different from the target composition ratio over time.

Meanwhile, in Example B-6 (FIG. 17), by using Sa with the monomer composition ratio being designed using the above factors and Tb with the target composition ratio, and providing the later step of feeding Uc over 2 hours after the main step (completion of dropwise addition of Tb), polymer molecules having a composition ratio almost the same as the target composition ratio are formed immediately after the start of polymerization reaction and continue to be formed, and even after the completion of the main step (reaction time of 4 hours), the polymer composition ratio is substantially close to the target composition ratio, thereby alleviating variations in composition ratio depending on reaction times.

(Refining of a Polymer)

The mixture solvent of methanol and water (methanol/water=80/20 volume ratio) and (methanol/water=90/10 volume ratio) used in the polymer refining step of Example B-1 were altered to isopropylether. A polymer P6 was obtained from the polymerization reaction solution in the flask after the reaction was continued for 7 hours by the same procedures as in Example B-1 except for the above alteration. Mw and Mw/Mn, and also the solubility of the polymer P6 were evaluated. The results are shown in Table 21.

Comparative Examples B-2 to B-7

In Reference Examples B-1 to B-6, after the reaction time of 7 hours, using the polymerization reaction solution in the flask obtained by cooling the flask to ambient temperature to stop the reaction, comparative polymers were respectively obtained for: Reference Example B-1 by the same procedure as in the polymer refining step of Example B-1; Reference Example B-2 by the same procedure as in the polymer refining step of Example B-2; Reference Example B-3 by the same procedure as in the polymer refining step of Example B-3; Reference Example B-4 by the same procedure as in the polymer refining step of Example B-4; Reference Example B-5 by the same procedure as in the polymer refining step of Example B-5; and Reference Example B-6 by the same procedure as in the polymer refining step of Example B-6. With regard to the comparative polymers thus obtained, Mw and Mw/Mn were determined as in Example B-1 and solubility thereof was evaluated. Results for Comparative Examples 2 and 3 are shown in Table 20 and results for Comparative Examples 4 to 7 are shown in Table 21.

In Comparative Examples B-2 and B-3, resist compositions were prepared using the comparative polymers thus obtained, by the same procedures as in Example B-1. Then, the sensitivity of the resist composition was evaluated. The results are shown in Table 20.

TABLE 20

| | | | Evaluation Results | |
|---|---|---|---|---|
| | Mw | Mw/Mn | Solubility [Amount of heptan added (wt %)] | Sensitivity (mJ/cm$^2$) |
| Example B-1 | 10500 | 1.62 | 14.2 | 1.01 |
| Comparative Example B-1 | 10700 | 1.67 | 10.8 | 1.72 |
| Comparative Example B-2 (Reference Example B-1) | 10600 | 1.75 | 11.6 | 1.65 |
| Example B-2 | 8400 | 1.58 | 6.15 | 0.51 |
| Comparative Example B-3 (Reference Example B-2) | 7400 | 1.65 | 5.7 | 0.78 |

As obvious from the results shown in Table 20, the polymer obtained in Example B-1 (total amount of monomers contained in Uc added dropwise in the main step and the later step: 2.15 mass %) showed substantially increased solubility and increased sensitivity of a resist composition produced therefrom, compared to polymers obtained in Comparative Example B-1 (total amount of monomers contained in Uc added dropwise in the main step and the later step: 14.9 mass %) and Comparative Example B-2 (dropwise addition at a constant rate without discriminating between the main step and the later step). Comparative Example B-1, in which the total amount of monomers contained in the solution Uc added dropwise in the later step was not appropriately controlled, showed substantially reduced solubility compared to Example B-1.

The polymer obtained in Example B-2 (total amount of monomers contained in Uc added dropwise in the main step and the later step: 2.68 mass %) showed substantially increased solubility and increased sensitivity of a resist composition produced therefrom, compared to Comparative Example B-3 (dropwise addition at a constant rate).

TABLE 21

| | Mw | Mw/Mn | Evaluation Results Solubility (Amount of heptan added/wt %) |
|---|---|---|---|
| Example B-3 | 9700 | 1.71 | 9.91 |
| Comparative Erample B-4 (Reference Example B-3) | 10100 | 1.83 | 7.24 |
| Example B-4 | 12300 | 1.81 | 16.32 |
| Comparative Example B-5 (Reference Example B-4) | 12400 | 1.89 | 12.25 |
| Example B-5 | 11600 | 1.75 | 9.21 |
| Comparative Example B-6 (Reference Example B-5) | 11900 | 1.82 | 6.88 |
| Example B-6 | 6500 | 1.91 | 3.02 |
| Comparative Example B-7 (Reference Example B-6) | 6700 | 1.93 | Not dissolved in PGMEA |

As obvious from the results shown in Table 21, the polymer obtained in Example B-3 (total amount of monomers contained in Uc added dropwise in the main step and the later step: 1.99 mass %) showed substantially increased solubility compared to a polymer obtained in Comparative Example B-4 (dropwise addition at a constant rate without discriminating between the main step and the later step).

Also in Examples B-4 to B-6, the composition ratio of polymer formed as a result of polymerization reaction was constant through the entire reaction period, and generation of a component with a largely biased copolymer composition ratio was successfully suppressed. In addition, solubility was substantially increased compared to polymers obtained in Comparative Examples B-5 to B-7 (dropwise addition at a constant rate without discriminating between the main step and the later step).

The following examples relate to property evaluation based on randomness of chain structure by the method for evaluating copolymer of the present embodiment. However, the present embodiment is not limited to these evaluations of copolymer.

Synthesis Example C-1: Homopolymer C-A-1

First, 3.40 parts of the monomer (m-1), 1.38 parts of dimethyl-2,2'-azobisisobutylate (trade name: V601, manufactured by Wako Pure Chemical Industries Ltd.), and 13.6 parts of ethyl lactate were added in a Schlenk flask of 25 ml, and nitrogen was injected into the solution for 1 minute at a rate of 200 ml/min. The flask was then bathed at 80° C. while stirring the content for 3 hours.

Then, the reaction solution thus obtained was added dropwise to methanol having a volume twenty times that of the reaction solution while stirring, to obtain a white precipitate (homopolymer C-A-1). Then, the washed precipitate was separated by filtration to obtain a wet polymer powder. The wet polymer powder was dried at 40° C. under reduced pressure for about 40 hours to obtain a white powder (2.0 g).

Synthesis Examples C-2 and C-3: Homopolymers C-A-2 and C-A-3

In the present Synthesis Examples, the monomers used were altered from (m-1) to (m-2) and from (m-1) to (m-3) respectively. Homopolymers C-A-2 (2.4 g) and C-A-3 (1.8 g) were obtained by the same procedures as in Synthesis Example C-1 except for the above alteration.

Synthesis Examples C-4 and C-5: Homopolymers C-A-4 and C-A-5

In the present Synthesis Examples, the monomers used were altered from (m-1) to (m-4) and from (m-1) to (m-5) respectively, and the solvent was altered from 13.6 g of ethyl lactate to a mixture of ethyl lactate and PGMEA (ethyl lactate/PGMEA=50/50 volume ratio). Homopolymers C-A-4 (2.7 g) and C-A-5 (1.4 g) were obtained by the same procedures as in Synthesis Example C-1 except for the above alterations.

Synthesis Example C-6: Homopolymer C-A-6

In the present Synthesis Example, the monomer used were altered from (m-1) to (m-14) and the solvent was altered from 13.6 g of ethyl lactate to dimethylformamide. Homopolymer C-A-6 (2.7 g) was obtained by the same procedures as in Synthesis Example C-1 except for the above alterations.

[Chemical Formula 9]

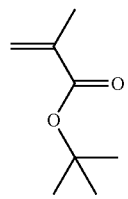

(m-14)

Synthesis Example C-7: Homopolymer C-B-1

Production of a Copolymer

In the present Synthesis Examples, the monomers (m-1), (m-2) and (m-3) were polymerized by the partial dropping method. The molar ratio of the monomers used is as follows: (m-1):(m-2):(m-3)=39.0:41.3:19.7

A flask equipped with a nitrogen introduction port, a stirrer, a condenser, a dropping funnel, and a temperature gauge was charged with: 79.0 parts of ethyl lactate; 2.72 parts of the monomer (m-1); 4.90 parts of the monomer (m-2); and 2.02 parts of the monomer (m-3) in a nitrogen atmosphere. The flask was bathed. Then, the temperature of the bath was raised to 80° C. while stirring the content in the flask.

A solution containing 3.6 parts of ethyl lactate and 1.196 parts of dimethyl-2,2'-azobisisobutylate (trade name: V601 mentioned above) was added dropwise at a fixed rate over 15 minutes in the flask from a dropping machine containing the solution, and a solution containing 23.80 parts of the monomer (m-1), 27.44 parts of the monomer (m-2), 16.52 parts of the monomer (m-3), 98.06 parts of ethyl lactate, and 0.643 parts of dimethyl-2,2'-azobisisobutylate (trade name: V601 mentioned above) was added dropwise at a fixed rate over 4 hours in the flask from a dropping machine containing the solution. The flask was kept at 80° C. for 3 hours.

Then, the polymerization reaction solution in the flask was added dropwise to a mixture solvent of methanol and water (methanol/water=80/20 ratio by volume) having a volume approximately ten times that of the reaction solution while stirring to obtain a white precipitate (copolymer C-B-1). The precipitate was separated by filtration. Then, the separated precipitate was again poured into a mixture solvent of methanol and water (methanol/water=90/10 ratio by volume) having the same amount as above. Then, the mixture was washed while stirring. Then, the washed precipitate was separated by filtration to obtain a wet polymer powder. The wet polymer powder was dried at 40° C. under reduced pressure for about 40 hours to obtain a white powder (66.0 g).

The obtained white powder was analyzed by $^1$H-NMR and GPC to find the average monomer composition ratio and Mw of all copolymers. Also, the solubility of the obtained copolymer C-B-1 was evaluated by the above method. The results are shown in Table 22. The molar ratio, molecular weight, the evaluation distance L (S) as an evaluated value, the time (minutes) showing solubility, and exposure dose as sensitivity of monomers m-1, m-2 and m-3 in respective compositions of copolymers C-B-1, C-B-2 and C-B-3 are shown in Table 22.

(Production of a Resist Composition)

2 parts of triphenylsulfonium triflate as a photoacid generator and 700 parts of PGMEA as a solvent were blended with 100 parts of the obtained copolymer C-B-1 to obtain a homogeneous solution. Then, this solution was filtered through a membrane filter having a pore size of 0.1 μm to prepare a resist composition solution. The sensitivity of the obtained resist composition was evaluated by the above method. The results are shown in Table 22.

Synthesis Example C-8: Homopolymer C-B-2

In Synthesis Example C-7, a copolymer was synthesized by the total dropping method without any monomer existing in advance in the flask. The molar ratio of the monomers used in this Synthesis Example is as follows:

(m-1):(m-2):(m-3)=40.0:40.0:20.0

Specifically, the same flask that was used in Synthesis Example C-7 was charged with 64.5 parts of ethyl lactate in a nitrogen atmosphere. The flask was bathed. Then, the temperature of the bath was raised to 80° C. while stirring the content in the flask.

A solution containing 27.20 parts of the monomer (m-1), 31.36 parts of the monomer (m-2), 18.88 parts of the monomer (m-3), 112.6 parts of ethyl lactate, and 2.576 parts of dimethyl-2,2'-azobisisobutylate (trade name: V601 mentioned above) was added dropwise at a fixed rate over 4 hours in the flask from a dropping machine containing the solution. The flask was kept at 80° C. for 3 hours.

After that, a white precipitate (copolymer C-B-2) was obtained by the same procedures as in Synthesis Example C-7. The precipitate was then separated by filtration. Then, the separated precipitate was washed. After being washed, the precipitate was separated by filtration. The obtained precipitate was dried to obtain a white powder (64.0 g).

The obtained copolymer C-B-2 was measured and evaluated by the same procedures as in Synthesis Example C-7. The results are shown in Table 22.

Synthesis Example C-9: Homopolymer C-B-3

In Synthesis Example C-7, a flask was charged with all of the monomers and a solvent in advance, and the copolymer was synthesized by the batch method. The molar ratio of the monomers used in this example is as follows:
(m-1):(m-2):(m-3)=40.0:40.0:20.0
15.5 parts of ethyl lactate, 1.36 parts of the monomer (m-1), 1.57 parts of the monomer (m-2), 0.94 parts of the monomer (m-3), and 1.15 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring the content for 3 hours.

Then, the reaction solution thus obtained was added dropwise to methanol having a volume approximately ten times that of the reaction solution while stirring, to obtain a white precipitate (copolymer C-B-3). Then, the washed precipitate was separated by filtration to obtain a wet polymer powder. The wet copolymer powder was dried at 40° C. under reduced pressure for about 40 hours to obtain a white powder C- (2.8 g).

The obtained copolymer C-B-3 was measured and evaluated by the same procedures as in Synthesis Example C-7. The results are shown in Table 22.

Synthesis Example C-10: Homopolymer C-B-4

In the present Synthesis Examples, the monomers (m-4), (m-5) and (m-3) were polymerized by the partial dropping method. The molar ratio of the monomers used is as follows:
(m-4):(m-5):(m-3)=35.5:34.3:30.2

A flask similar to that of Synthesis Example C-7 was charged with: 42.6 parts of ethyl lactate; 41.5 parts of PGMEA; 2.83 parts of the monomer (m-4); 8.68 parts of the monomer (m-5); and 3.52 parts of the monomer (m-3) in a nitrogen atmosphere. The flask was bathed. Then, the temperature of the bath was raised to 80° C. while stirring the content in the flask.

A solution containing 6.5 parts of ethyl lactate and 2.152 parts of dimethyl-2,2'-azobisisobutylate (trade name: V601 mentioned above) was added dropwise at a fixed rate over 20 minutes in the flask from a dropping machine containing the solution, and a solution containing 18.09 parts of the monomer (m-4), 20.83 parts of the monomer (m-5), 21.15 parts of the monomer (m-3), 38.6 parts of ethyl lactate, 45.1 parts of PGMEA, and 1.435 parts of dimethyl-2,2'-azobisisobutylate (trade name: V601 mentioned above) was added dropwise at a fixed rate over 4 hours in the flask from a dropping machine containing the solution. The flask was kept at 80° C. for 3 hours.

Then, the polymerization reaction solution in the flask was added dropwise to a mixture solvent of methanol and water (methanol/water=85/15 ratio by volume) having a volume approximately ten times that of the reaction solution while stirring to obtain a white precipitate (copolymer C-B-4). Then, the precipitate was separated by filtration. Then, the separated precipitate was again poured into a mixture solvent of methanol and water (methanol/water=95/5 ratio by volume) having the same amount as above. Then, the mixture was washed while stirring. Then, the washed precipitate was separated by filtration to obtain a wet polymer powder. The wet polymer powder was dried at 40° C. under reduced pressure for about 40 hours to obtain a white powder (54.1 g).

The obtained copolymer C-B-4 was measured and evaluated by the same procedures as in Synthesis Example C-7. The results are shown in Table 23. The molar ratio, molecular weight, the evaluation distance L (S) as an evaluated value, the time (minutes) showing solubility, and exposure dose as sensitivity of monomers m-4, m-5 and m-3 in respective compositions of copolymers C-B-4, C-B-5 and C-B-6 are shown in Table 23.

Synthesis Example C-11: Homopolymer C-B-5

In Synthesis Example C-10, a copolymer was synthesized by the total dropping method without any monomer existing in advance in the flask. The molar ratio of the monomers used in this Synthesis Example is as follows:
(m-4):(m-5):(m-3)=35.0:35.0:30.0

Specifically, the same flask that was used in Synthesis Example C-7 was charged with 54.5 parts of ethyl lactate and 23.3 parts of PGMEA in a nitrogen atmosphere. The flask was bathed. Then, the temperature of the bath was raised to 80° C. while stirring the content in the flask.

A solution containing 51.17 parts of the monomer (m-4), 37.32 parts of the monomer (m-5), 30.44 parts of the monomer (m-3), 98.0 parts of ethyl lactate, 16.4 parts of PGMEA, and 5.538 parts of dimethyl-2,2'-azobisisobutylate (trade name: V601 mentioned above) was added dropwise at a fixed rate over 4 hours in the flask from a dropping machine containing the solution. The flask was kept at 80° C. for 3 hours.

After that, a white precipitate (copolymer C-B-5) was obtained by the same procedures as in Synthesis Example C-10. The precipitate was then separated by filtration. Then, the separated precipitate was washed. After being washed, the precipitate was separated by filtration. The obtained precipitate was dried to obtain a white powder (51.0 g).

The obtained copolymer C-B-5 was measured and evaluated by the same procedures as in Synthesis Example C-7. The results are shown in Table 23.

Synthesis Example C-12: Homopolymer C-B-6

In Synthesis Example C-10, a flask was charged with all of the monomers and a solvent in advance, and the copolymer was synthesized by the batch method. The molar ratio of the monomers used in this Synthesis Example is as follows:

(m-4):(m-5):(m-3)=36.0:32.0:32.0

4.9 parts of ethyl lactate, 4.9 parts of PGMEA, 1.84 parts of the monomer (m-4), 2.38 parts of the monomer (m-5), 2.27 parts of the monomer (m-3), and 1.725 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring the content for 3 hours.

Then, the reaction solution thus obtained was added dropwise to methanol having a volume approximately ten times that of the reaction solution while stirring, to obtain a white precipitate (copolymer C-B-6). Then, the washed precipitate was separated by filtration to obtain a wet polymer powder. The wet polymer powder was dried at 40° C. under reduced pressure for about 40 hours to obtain a white powder (6.1 g).

The obtained copolymer C-B-6 was measured and evaluated by the same procedures as in Synthesis Example C-7. The results are shown in Table 23.

Synthesis Example C-13: Homopolymer C-B-7

In the present Synthesis Example, a copolymer was synthesized from the monomers (m-1), (m-14) and (m-3) by a method of not charging the flask with any monomer in advance (total dropping method). The molar ratio of the monomers used is as follows:

(m-1):(m-14):(m-3)=40.0:40.0:20.0

Specifically, the same flask that was used in Synthesis Example C-7 was charged with 43.1 parts of DMF in a nitrogen atmosphere. The flask was bathed. Then, the temperature of the bath was raised to 80° C. while stirring the content in the flask.

A solution containing 10.21 parts of the monomer (m-1), 8.53 parts of the monomer (m-14), 7.09 parts of the monomer (m-3), 60.3 parts of DMF, and 0.449 parts of dimethyl-2,2'-azobisisobutylate (trade name: V601 mentioned above) was added dropwise at a fixed rate over 3 hours in the flask from a dropping machine containing the solution. The flask was kept at 80° C. for 3 hours.

Then, the polymerization reaction solution in the flask was added dropwise to a mixture solvent of methanol and water (methanol/water=70/30 ratio by volume) having a volume approximately ten times that of the reaction solution while stirring to obtain a white precipitate (copolymer C-B-7). Then, the precipitate was separated by filtration. Then, the separated precipitate was again poured into a mixture solvent of methanol and water (methanol/water=70/30 ratio by volume) having the same amount as above. Then, the mixture was washed while stirring. Then, the washed precipitate was separated by filtration to obtain a wet polymer powder. The wet polymer powder was dried at 40° C. under reduced pressure for about 40 hours to obtain a white powder (20.1 g).

The obtained copolymer C-B-7 was measured and evaluated by the same procedures as in Synthesis Example C-7. The results are shown in Table 24. The molar ratio, molecular weight, the evaluation distance L (S) as an evaluated value, the time (minutes) showing solubility, and exposure dose as sensitivity of monomers m-1, m-14 and m-3 in respective compositions of polymers C-B-7 and C-B-8 are shown in Table 24.

Synthesis Example C-14: Homopolymer C-B-8

In Synthesis Example C-13, a flask was charged with all of the monomers and a solvent in advance, and the copolymer was synthesized by the batch method. The molar ratio of the monomers used in this Synthesis Example is as follows:

(m-1):(m-14):(m-3)=40.0:40.0:20.0

8.3 parts of DMF, 0.82 parts of the monomer (m-1), 0.68 parts of the monomer (m-14), 0.57 parts of the monomer (m-3), and 0.332 parts of dimethyl-2,2'-azobisisobutylate (abovementioned V601 (trade name)) were added in a Schlenk flask of 25 ml, and then nitrogen was injected into the solution for 1 minute at a rate of 200 ml/min. The flask was then bathed at 80° C. while stirring the content for 6 hours.

Then, the reaction solution thus obtained was added dropwise to a mixture solvent of methanol and water (methanol/water=80/20 ratio by volume) having a volume approximately ten times that of the reaction solution while stirring to obtain a white precipitate (copolymer C-B-8). Then, the washed precipitate was separated by filtration to obtain a wet polymer powder. The wet polymer powder was dried at 40° C. under reduced pressure for about 40 hours to obtain a white powder (1.5 g).

The obtained copolymer C-B-8 was measured and evaluated by the same procedures as in Synthesis Example C-7. The results are shown in Table 24.

Modification C-1

The $^{13}$C-NMR measurement was conducted for the homopolymers C-A-1 to C-A-3 obtained in Synthesis Examples C-1 to C-3 and the copolymers C-B-1 to C-B-3 obtained in Synthesis Examples C-7 to C-9 by the NMR measurement unit 350.

The NMR spectra of the samples were obtained by the NMR measurement unit 350. In the NMR measurement unit 350, the number of scans in the measurement was 5000; the broadening factor in the FID processing was 4.0 Hz; the base peak was dimethylsulfoxide (39.5 ppm); baseline correction was performed on the NMR spectra thus measured; and the FID data for the samples was output to the waveform processing unit 311.

Subsequently, in each of frequencies of the NMR spectra in the FID signal obtained, the waveform processing unit 311 integrated a range of 175 to 179 ppm derived from carbonyl carbon in the polymer at intervals of 0.25 ppm, and obtained 16 integral values.

The waveform processing unit 311 then assigned monomer identification information (for example, "A-1" to "A-3") to each of the homopolymers C-A-1 to C-A-3, and stores the NMR spectrum data for each homopolymer, corresponding to the monomer identification information, to the NMR data storage unit 315.

In addition, the waveform processing unit 311 assigned sample identification information (for example, "B-1" to "B-3") to each of the copolymers C-B-1 to C-B-3, and stores the NMR spectrum data for copolymer of each sample, corresponding to the sample identification information, to the NMR data storage unit 315.

Thereafter, the principal component analysis unit 312 used, for example, Sirius (registered trademark) manufactured by Pattern Recognition Systems as multivariate analysis software, to conduct the principal component analysis of the 16 integral values regarding carbonyl carbon based on the NMR spectrum data of 6 types of polymers: the homopolymers C-A-1 to C-A-3; and copolymers C-B-1 to C-B-3, thereby constructing the experimental model of the matrix G shown in (31).

As a result, the number of types of monomers in the composition of the copolymers was determined to be 3. Given this, the number of dimensions of the principal component space in which the samples to be evaluated are arranged was set to 3, in other words, the number of principal components was set to 3. The contribution ratios of the first principal component to the third principal component were 67.1%, 24.5%, and 7.9%, respectively, and residue was 0.5%.

The principal component scores of the first principal component (hereinafter referred to as PC1), the second principal component (hereinafter referred to as PC2), and the third principal component (hereinafter referred to as PC3) of each of the homopolymers C-A-1 to C-A-3 and copolymers C-B-1 to C-B-3 were as shown in Table 25. Respective principal component scores of the first principal component, the second principal component, and the third principal component of the homopolymers C-A-1 to C-A-3 and copolymers C-B-1 to C-B-3 calculated by the principal component analysis unit 312 are shown in Table 25.

Then, in the three-dimensional space composed of the first principal component axis PC1, the second principal component axis PC2, and the third principal component axis PC3 shown in FIG. 3, the numerical value conversion unit 313 calculated the evaluation distance L (S) from the two-dimensional space (two-dimensional plane) composed of the homopolymers C-A-1 to C-A-3 to respective coordinate points of the copolymers C-B-1 to C-B-3, based on the coordinate values of the homopolymers C-A-1 to C-A-3 and the copolymers C-B-1 to C-B-3 (positions represented by the principal component scores of axes in the principal component space).

Here, the numerical value conversion unit 313 expressed the coordinate points of the homopolymers C-A-1, C-A-2, C-A-3 and the copolymers C-B-1, C-B-2, C-B-3 as follows, using the coordinate value PC1 (X) of the first principal component axis PC1, the coordinate value PC2 (X) of the second principal component axis PC2, and the coordinate value PC3 (X) of the third principal component axis PC3. Note that X in parentheses indicates the sample identification information representing a sample of copolymer to be evaluated.

Coordinate value of homopolymer C-A-1:

$P(A\text{-}1)=(PC1(A\text{-}1),PC2(A\text{-}1),PC3(A\text{-}1))$

Coordinate value of homopolymer C-A-2:

$P(A\text{-}2)=(PC1(A\text{-}2),PC2(A\text{-}2),PC3(A\text{-}2))$

Coordinate value of homopolymer C-A-3:

$P(A\text{-}3)=(PC1(A\text{-}3),PC2(A\text{-}3),PC3(A\text{-}3))$

Coordinate value of copolymer C-B-1:

$P(B\text{-}1)=(PC1(B\text{-}1),PC2(B\text{-}1),PC3(B\text{-}1))$

Coordinate value of copolymer C-B-2:

$P(B\text{-}2)=(PC1(B\text{-}2),PC2(B\text{-}2),PC3(B\text{-}2))$

Coordinate value of copolymer C-B-3:

$P(B\text{-}3)=(PC1(B\text{-}3),PC2(B\text{-}3),PC3(B\text{-}3))$

Here, in the homopolymers C-A-1, C-A-2, and C-A-3, the same monomers as constitutional units are arranged and bound completely successively in the polymer chain. Therefore, the two-dimensional plane (two-dimensional comparative space) passing through all the coordinate values P (A-1), P (A-2), and P (A-3) is a two-dimensional space, which is one dimensional smaller than the three-dimensional principal component space, composed of an aggregate of copolymer with the highest consecutiveness of monomers as constitutional units, i.e. with the lowest randomness. As a result, as described above, the evaluation distance L (S) between the two-dimensional plane and the copolymer to be evaluated indicates a distance from the two-dimensional space representing characteristics of the lowest randomness and indicates randomness of arrangement of monomers in the chain in the copolymer.

The numerical value conversion unit 313 obtained numerical values a, b, c, d by the following equations.

$a=(PC2(A\text{-}2)-PC2(A\text{-}1))\times(PC3(A\text{-}3)-PC3(A\text{-}1))-(PC2(A\text{-}3)-PC2(A\text{-}1))\times(PC3(A\text{-}2)-PC3(A\text{-}1))$ $b=(PC3(A\text{-}2)-PC3(A\text{-}1))\times(PC1(A\text{-}3)-PC1(A\text{-}1))-(PC3(A\text{-}3)-PC3(A\text{-}1))\times(PC1(A\text{-}2)-PC1(A\text{-}1))$ $c=(PC1(A\text{-}2)-PC1(A\text{-}1))\times(PC2(A\text{-}3)-PC2(A\text{-}1))-(PC1(A\text{-}3)-PC1(A\text{-}1))\times(PC2(A\text{-}2)-PC2(A\text{-}1))$ $d=-(PC2(A\text{-}2)-PC2(A\text{-}1))\times(PC3(A\text{-}3)-PC3(A\text{-}1))-(PC2(A\text{-}3)-PC2(A\text{-}1))\times(PC3(A\text{-}2)-PC3(A\text{-}1))\times PC1(A\text{-}1)-(PC3(A\text{-}2)-PC3(A\text{-}1))\times(PC1(A\text{-}3)-PC1(A\text{-}1))-(PC3(A\text{-}3)-PC3(A\text{-}1))\times(PC1(A\text{-}2)-PC1(A\text{-}1))\times PC1(A\text{-}2)-(PC1(A\text{-}2)-PC1(A\text{-}1))\times(PC2(A\text{-}3)-PC2(A\text{-}1))-(PC1(A\text{-}3)-PC1(A\text{-}1))\times(PC2(A\text{-}2)-PC2(A\text{-}1))\times PC1(A\text{-}3)$ Next, the numerical value conversion unit 313 calculated the evaluation distance L (S) between the two-dimensional plane passing through all the coordinate points P (A-1), P (A-2), and P (A-3) and the coordinate point P (PC1, PC2, PC3) of the copolymer to be evaluated by the following equation, using the numerical values a, b, and c thus obtained.

$L=|a\times SPC1+b\times SPC2+c\times SPC3+d|/(a^2+b^2+c^2)^{1/2}$

In this equation, SPC1 is a coordinate value of the copolymer to be evaluated in the first principal component axis (principal component score of the first principal component); SPC2 is a coordinate value of the copolymer to be evaluated in the second principal component axis (principal component score of the second principal component); and SPC3 is a coordinate value of the copolymer to be evaluated in the third principal component axis (principal component score of the third principal component).

As described above, the evaluation distances L (S) between the coordinate points representing positions of characteristics of the copolymer to be evaluated in the principal component space and the two-dimensional plane passing through all the coordinate points P (A-1), P (A-2), and P (A-3) of homopolymers composed of respective monomers constituting the copolymer are shown in Table 22.

As is obvious from Table 22, larger evaluation distance L (S) indicates higher randomness of copolymer chain, providing superior lithography characteristics: solubility and photosensitivity. As is obvious from Table 22, the evaluation distance L (S) gets larger in an order of: copolymer C-B-3, copolymer C-B-2, and copolymer C-B-1. The lithography characteristics (solubility and photosensitivity) of compositions for resist prepared using the copolymers get better in the order of: copolymer C-B-3, copolymer C-B-2, and copolymer C-B-1, an ascending order of the evaluation distance L (S). As described above, by obtaining the evaluation distance L (S) of the copolymer used for preparing a composition for resist, the lithography characteristics of the composition for resist prepared using the copolymer can be estimated without actually preparing the composition for resist and performing lithography. Here, the copolymer C-B-3 showed photosensitivity that is immeasurably low, and was not completely dissolved within a measurable period of time.

Modification C-2

The $^{13}$C-NMR measurement was conducted for the homopolymers C-A-3 to C-A-5 obtained in Synthesis Examples C-3 to C-5 and the copolymers C-B-4 to C-B-6 obtained in Synthesis Examples C-10 to C-12 to thereby obtaining spectra. The number of scans in the measurement was 5000; the broadening factor in the FID processing was 4.0 Hz; the base peak was dimethylsulfoxide (39.5 ppm); and the baseline correction was performed.

In each of the spectra thus obtained, a range of 173 to 179 ppm derived from carbonyl carbon in the polymer was integrated at intervals of 0.25 ppm, and 20 integral values were obtained.

The evaluation distance L (S) from a plane passing through the points of the principal component scores of all the homopolymers was obtained by the same procedures as Modification C-1.

The principal component scores of the principal components that represent coordinate values of the first principal component axis PC1, the second principal component axis PC2, and the third principal component axis PC3 are shown in Table 26. Results of the evaluation distance L (S) are shown in Table 23. Respective principal component scores of the first principal component, the second principal component, and the third principal component of the homopolymers C-A-3 to C-A-5 and copolymers C-B-4 to C-B-6 calculated by the principal component analysis unit 312 are shown in Table 26.

As is obvious from Table 23, the evaluation distance L (S) gets larger in an order of: copolymer C-B-6, copolymer C-B-5, and copolymer C-B-4. The lithography characteristics (solubility and photosensitivity) of compositions for resist prepared using the copolymers get better in the order of: copolymer C-B-6, copolymer C-B-5, and copolymer C-B-4, an ascending order of the evaluation distance L (S). As described above, by obtaining the evaluation distance L (S) of the copolymer used for preparing a composition for resist, the lithography characteristics of the composition for resist prepared using the copolymer can be estimated without actually preparing the composition for resist and performing lithography. Here, the copolymer C-B-6 showed photosensitivity that is immeasurably low, and was not completely dissolved within a measurable period of time.

Modification C-3

The $^{13}$C-NMR measurement was conducted for the homopolymers C-A-1, C-A-3, C-A-6 obtained in Synthesis Examples C-1, C-3, C-6 and the copolymers C-B-7 and C-B-8 obtained in Synthesis Examples C-13 to C-14 to thereby obtain spectra. The number of scans in the measurement was 5000; the broadening factor in the FID processing was 3.0 Hz; the base peak was dimethylsulfoxide (39.5 ppm); and the baseline correction was performed.

As described above, in each of the NMR spectra thus obtained, a range of 174 to 179 ppm derived from carbonyl carbon in the polymer was integrated at intervals of 0.25 ppm, and 16 integral values were obtained.

The principal component analysis was performed on the NMR spectrum data obtained from the NMR spectrum signals, and the evaluation distance L (S) from a plane passing through the points of the principal component scores of all the homopolymers was obtained by the same procedures as Modification C-1.

The principal component scores of the principal components that represent coordinate values of the first principal component axis PC1, the second principal component axis PC2, and the third principal component axis PC3 are shown in Table 27. Results of the evaluation distance L (S) are shown in Table 24. Respective principal component scores of the first principal component, the second principal component, and the third principal component of the homopolymers C-A-1, C-A-3, C-A-6 and copolymers C-B-7 and C-B-8 calculated by the principal component analysis unit 312 are shown in Table 27.

As is obvious from Table 24, the evaluation distance L (S) gets larger in an order of: copolymer C-B-8, copolymer C-B-7. The lithography characteristics (solubility and photosensitivity) of compositions for resist prepared using the copolymers get better in the order of: copolymer C-B-8, copolymer C-B-7, an ascending order of the evaluation distance L (S). As described above, by obtaining the evaluation distance L (S) of the copolymer used for preparing a composition for resist, the lithography characteristics of the composition for resist prepared using the copolymer can be estimated without actually preparing the composition for resist and performing lithography.

TABLE 22

| Polymer | Average monomer composition ratio (mol %) | | | Molecular weight Mw | L (S) | Solubility (min) | Senstivity (mJ/cm$^2$) |
| | α-GBLMA (m-1) | ECHMA (m-2) | HAdMA (m-3) | | | | |
|---|---|---|---|---|---|---|---|
| C-B-1 | 40 | 41 | 19 | 10000 | 19.5 | 17 | 1.32 |
| C-B-2 | 41 | 39 | 20 | 10600 | 19.1 | 31 | 1.61 |
| C-B-3 | 46 | 40 | 14 | 10000 | 18.5 | Not completely dissolved | Evaluation not possible |

TABLE 23

| Polymer | Average monomer composition ratio (mol %) | | | Molecular weight Mw | L (S) | Solubility (min) | Senstivity (mJ/cm$^2$) |
|---|---|---|---|---|---|---|---|
| | HGBMA (m-4) | EAdMA (m-5) | HAdMA (m-3) | | | | |
| C-B-4 | 37 | 32 | 31 | 8200 | 17.3 | 12 | 0.54 |
| C-B-5 | 37 | 33 | 30 | 6900 | 17.1 | 18 | 0.78 |
| C-B-6 | 37 | 35 | 28 | 7500 | 15.7 | Not completely dissolved | Evaluation not possible |

TABLE 24

| Polymer | Average monomer composition ratio (mol %) | | | Molecular weight Mw | L (S) | Solubility (min) | Sensitivity (mJ/cm$^2$) |
|---|---|---|---|---|---|---|---|
| | α-GBLMA (m-1) | TBMA (m-14) | HAdMA (m-3) | | | | |
| C-B-7 | 40 | 40 | 20 | 10400 | 6.01 | 33 | 9.8 |
| C-B-8 | 40 | 38 | 22 | 13200 | 5.78 | 42 | 13.2 |

TABLE 25

| Polymer | Principal component score | | |
|---|---|---|---|
| | PC1 | PC2 | PC3 |
| C-A-1 | −28.621 | −16.785 | 13.318 |
| C-A-2 | 8.709 | 28.651 | 9.501 |
| C-A-3 | 47.728 | −14.793 | 1.579 |
| C-B-1 | −8.455 | 1.716 | −8.767 |
| C-B-2 | −7.852 | 1.251 | −8.458 |
| C-B-3 | −11.509 | −0.040 | −7.173 |

TABLE 26

| Polymer | Principal component score | | |
|---|---|---|---|
| | PC1 | PC2 | PC3 |
| C-A-4 | −3.740 | 16.860 | 12.010 |
| C-A-5 | −12.760 | −17.390 | 8.390 |
| C-A-3 | 27.110 | −5.300 | 2.380 |
| C-B-4 | −3.460 | 1.850 | −8.270 |
| C-B-5 | −3.72 | 1.98 | −7.95 |
| C-B-6 | −3.810 | 1.980 | −6.560 |

TABLE 27

| Polymer | Principal component score | | |
|---|---|---|---|
| | PC1 | PC2 | PC3 |
| C-A-1 | −12.653 | 0.294 | 4.656 |
| C-A-6 | 11.700 | −9.570 | 1.742 |
| C-A-3 | 10.894 | 10.306 | 1.229 |
| C-B-7 | −2.840 | −0.332 | −2.692 |
| C-B-8 | −3.607 | −0.253 | −2.358 |

In the present embodiment, from the results shown in Tables 22, 23 and 24, it has been confirmed that: the value of the evaluation distance L (S) is correlated with the solubility leading to development defect or Eth representing sensitivity; and the lithography characteristics can be evaluated indirectly based on the value of L (S). It has been confirmed that the method of the present embodiment can evaluate the lithography characteristics indirectly with a high degree of accuracy.

The equation for the numerical value conversion unit 313 obtaining the evaluation distance L (S) in a case in which there are n monomers constituting a copolymer is shown hereinafter. In this case, the number of types of monomers is n; the principal component space is n-dimensional; the number of coordinate points of homopolymers composed only of each monomer is n; and the space including all the n coordinate points is (n−1)-th dimensional. Given this, the evaluation distance L (S) to be obtained is a distance between the coordinate point of the sample to be evaluated and the abovementioned (n−1)-th dimensional space.

The evaluation distance L (S) between a given coordinate point in the n-th dimensional space and the (n−1)-th dimensional space is obtained by: projecting the given coordinate point to the (n−1)-th dimensional space; and obtaining a length of a geodesic line connecting a coordinate point representing a projected position in the (n−1)-th dimensional space to the given coordinate point.

For example, in the n-th dimensional space composed of the first principal component axis PC1 to a n-th principal component axis PCn, the (n−1)-th dimensional space including all the coordinate points (positions of n principal component scores) of samples of homopolymer is obtained.

Here, with respect to the polymers C-A-1 to C-A-n composed of respective single-type constitutional units, the numerical value conversion unit 313 defines coordinate points P (A-1) to P (A-n), which are coordinate points composed of: a coordinate value (principal component score) on the first principal component axis PC1, . . . and a coordinate value (principal component score) on the n-th principal component axis PCn.

Next, the numerical value conversion unit 313 calculates the evaluation distance L (S) between the (n−1)-th dimensional space passing through all the coordinate points P (A-1) to P (A-n) and the coordinate point P (PC1, PC2, . . . PCn) of the copolymer to be evaluated by the following equation.

$$L(S) = |a_1 \times SPC1 + a_2 \times SPC2 + \ldots + a_n \times SPCn + a_{n+1}| / (a_1^2 + a_2^2 + \ldots + a_n^2)^{1/2}$$

In this equation, SPC1 is a coordinate value of the copolymer to be evaluated in the first principal component axis (principal component score of the first principal component); SPC2 is a coordinate value of the copolymer to be evaluated in the second principal component axis (principal component score of the second principal component); . . . and SPCn is a coordinate value of the copolymer to be evaluated in the n-th principal component axis (principal component score of the n-th principal component).

It should be noted that the (n−1)-th dimensional comparative space (one dimension smaller than the principal component space) represented by a relationship $a_1 \times SPC1 + a_2 \times SPC2 + \ldots + a_n \times SPCn + a_{n+1} = 0$ in the above equation for calculating the evaluation distance L (S) in the n-dimensional space passes through all the n coordinate points P (A-1) to P (A-n).

Here, the numerical value conversion unit 313 calculates the values (coefficients) $a_1$ to $a_{n+1}$ in the above equation by solving a n-th dimensional simultaneous equation in which each coordinate of the coordinate point P (A-1) assigned to an equation of the (n−1)-th dimensional comparative space.

As described above, in the processing by the principal component analysis unit 312, in a case in which a copolymer for resist S is composed of n constitutional units (monomers) (n denoting an integer of at least 2), the principal component analysis is conducted with respect to the chemical shift and the signal intensity in the NMR measurement of the copolymer for resist S and a homopolymer C-A-j composed only of single-type monomers as constitutional units (j=1 to n) to thereby calculate the principal component score Pj of each principal component. Since there are n types of monomers constituting the copolymer for resist S, n principal components (first principal component to n-th principal component) are used. Therefore, n principal component axes are formed.

Then, in the n-dimensional principal component space composed of n principal component axes (orthogonal coordinate axes), the numerical value conversion unit 313 forms coordinate points in the principal component space by using each of the principal component scores of the homopolymer C-A-j as a coordinate value on each of the principal component axes.

Subsequently, the numerical value conversion unit 313 considers: a coordinate point composed of the principal component score Pi (S) of the copolymer for resist to be evaluated as P(S); and a coordinate point composed of the principal component score Pi (A-j) of the homopolymer C-A-j as P (A-j), and calculates a distance between the (n−1)-th dimensional space passing through all the coordinate points P (A-j) and the coordinate point P(S) as the evaluation distance L (S).

Finally, the property evaluation unit 314 performs evaluation processing of lithography characteristics of the copolymer for resist to be evaluated, based on the evaluation distance L (S) calculated by the numerical value conversion unit 313 (i.e. evaluates lithography characteristics of the composition for resist produced from the copolymer, using the threshold described above).

In the present embodiment, evaluation of a copolymer for resist has been described as an example of a copolymer composed of a plurality (at least 2) of monomers; however, any copolymer composed of a plurality of monomers including a copolymer for lithography can be an evaluation target, and an alignment state of monomers in the composition of such a copolymer can also be qualitatively evaluated.

By determining a correlation between an alignment state of monomers in the composition of a copolymer and characteristics of the copolymer including physical properties, the characteristics of the copolymer can be estimated from the evaluation distance L (S) without actually conducting an experiment using the copolymer, as in the case of the copolymer for resist.

An analysis process of copolymer composition can be performed by storing programs providing functions of the waveform processing unit 311, the principal component analysis unit 312, the numerical value conversion unit 313, and the property evaluation unit 314 in FIG. 2 into a computer-readable storage medium, and making a computer system read and execute the programs stored in the storage medium. As used herein, the "computer system" is the same as the abovementioned matter, and includes an OS and hardware such as peripherals.

The embodiment of the present invention has been described in detail with reference to the drawings; however, the specific configuration of the present invention is not limited thereto and can include design and the like not departing from a scope of the present invention.

DENOTATION OF REFERENCE NUMERALS

11 Target variable analysis unit
12 Waveform processing unit
13 Explanatory variable analysis unit
14 Model generation unit
15 Sample analysis unit
16 Storage unit
17 Display unit
18 Control unit
31 Copolymer composition analysis apparatus
311 Waveform processing unit
312 Principal component analysis unit
313 Numerical value conversion unit
314 Property evaluation unit
315 NMR data storage unit
316 Principal component data storage unit
350 NMR measurement unit

The invention claimed is:

1. A method for producing a polymer by copolymerization of at least two monomers $\alpha_1$ to $\alpha_n$ having different copolymerization reactivities to obtain a polymer (P) comprising at least two monomer units $\alpha'_1$ to $\alpha'_n$ in a target composition having a content ratio of the monomer units $\alpha'_1$ to $\alpha'_n$ of (P) according to $\alpha'_1:\alpha'_2: \ldots :\alpha'_n$;

the method comprising:

first feeding dropwise to a polymerization reactor at least one solution Sa comprising the at least two monomers $\alpha_1$ to $\alpha_n$ in a first composition ratio such that a proportion of a monomer having the lowest copolymerization reaction rate among the at least two monomers $\alpha_1$ to $\alpha_n$ is greater than in the target composition;

adding to the reactor dropwise a polymerization initiator either after the addition of the at least one solution Sa or simultaneous with the addition of Sa, feeding to the reactor at least one solution Tb comprising the at least two monomers $\alpha_1$ to $\alpha_n$ in a second composition ratio equal to the target composition either simultaneous with the start of the solution Sa or after the addition of Sa wherein the addition of Sa is complete before the addition of Tb; and after completion of the addition of solution Tb, feeding at least one solution Uc comprising the at least two monomers $\alpha_1$ to $\alpha_n$ monomers in a third composition such that a proportion of the monomer having the lowest copolymerization reaction rate is smaller than in the target composition, wherein when a period of time between the start and completion of dropwise addition of the solution Uc is defined as a later dropping time; a value obtained by dividing the total feed amount of monomers in the later step by the later dropping time is defined as an average feed rate, 50 to 95% of the monomers of $U_c$ are fed in a higher rate than the average feed rate during a high rate feed period of time between 0% to k % of the later dropping time wherein k is 5 to 95%;

wherein n is an integer of at least 2, when a standard time is defined as a time elapsed from the start of the addition of the polymerization initiator to completion of the addition of Tb, the polymerization initiator is added at such rate that 30 to 90% of the total feed of the polymerization initiator is added during the initial 5 to 20% of the standard time, and a total amount of the monomers in the at least one solution Uc is from 0.1 to 10 mass % of a total feed amount of the monomers.

2. The method according to claim 1, wherein content ratios of the monomer units in the first solution Sa are from 0.8 to 1.2 times of respective values of the content ratios of the monomer units in a target solution S'a which are obtained by a method comprising:

(i) obtaining compositions $M_1:M_2: \ldots :M_n$ of the at least two monomers $\alpha_1$ to $\alpha_n$ remaining in the reactor after respective passages of time $t_1, t_2, t_3 \ldots$, from a start of dropwise addition of a dropping solution at a constant rate into a reactor containing only a solvent and a ratio $P_1:P_2: \ldots :P_n$ of the at least two monomer units $\alpha'_1$ to $\alpha'_n$ in polymers respectively formed between time zone $t_1$ and $t_2$, between time zone $t_2$ and $t_3, \ldots$, wherein the dropping solution comprises:

100 mass parts of a monomer mixture with the same monomer composition ratio as the target composition $\alpha'_1:\alpha'_2: \ldots :\alpha'_n$;

a polymerization initiator; and a solvent;

(ii) determining a time zone from $t_m$ to $t_{m+1}$ wherein m is an integer of at least 1 in which the ratio $P_1:P_2: \ldots :P_n$ is closest to the target composition $\alpha'_1:\alpha'_2: \ldots :\alpha'_n$;

(iii) obtaining factors $F_1, F_2 \ldots F_n$ based on a value of $P_1:P_2: \ldots :P_n$ in the time zone from $t_m$ to $t_{m+1}$ and a value of $M_1:M_2: \ldots :M_n$ at the passage of time $t_m$, with equation:

$$F_1=P_1/M_1, F_2=P_2/M_2, \ldots F_n=P_n/M_n; \text{ and}$$

(iv) obtaining $\alpha_{11}=\alpha'_1/F_1, \alpha_{12}=\alpha'_2/F_2, \ldots \alpha_{1n}=\alpha'_n/F_n$, when compositions of S'a are represented by $\alpha_{11}:\alpha_{12}: \ldots :\alpha_{1n}$ and the factors obtained in above (iii) are represented by $F_1, F_2 \ldots F_n$.

3. The method according to claim 1, wherein content ratios of the monomer units in the third solution Uc are from 0.8 to 1.2 times of respective values of the content ratios of the monomer units in a target solution U'c which are obtained by a method comprising:

(v) obtaining compositions $M_1:M_2: \ldots :M_n$ of the at least two monomers $\alpha_1$ to $\alpha_n$ remaining in the reactor after respective passages of time $t_1, t_2, t_3 \ldots$, from a start of dropwise addition of a dropping solution at a constant rate into a reactor containing only the solvent and a ratio $P_1:P_2: \ldots :P_n$ of the monomer units $\alpha'_1$ to $\alpha'_n$ in polymers respectively formed between time zone $t_1$ and $t_2$, between time zone $t_2$ and $t_3, \ldots$ wherein the dropping solution comprises:

100 mass parts of a monomer mixture with the same monomer composition ratio as the target composition $\alpha'_1:\alpha'_2: \ldots :\alpha'_n$;

a polymerization initiator; and a solvent;

(vi) determining a time zone from $t_m$ to $t_{m+1}$ wherein m is an integer of at least 1 in which the ratio $P_1:P_2: \ldots :P_n$ is closest to the target composition $\alpha'_1:\alpha'_2: \ldots :\alpha'_n$;

(vii) obtaining factors $F_1, F_2 \ldots F_n$ based on a value of $P_1:P_2: \ldots :P_n$ in the time zone from $t_m$ to $t_{m+1}$ and a value of $M_1:M_2: \ldots :M_n$ at the passage of time $t_m$, with equation:

$$F_1=P_1/M_1, F_2=P_2/M_2, \ldots F_n=P_n/M_n; \text{ and}$$

(viii) obtaining $\alpha_{31}=\alpha'_1 \times F_1/(\alpha'_1 \times F_1+\alpha'_2 \times F_2+ \ldots +\alpha'_n \times F_n)$, $\alpha_{32}=\alpha'_2 \times F_2/(\alpha'_1 \times F_1+\alpha'_2 \times F_2+ \ldots +\alpha'_n \times F_n)$, . . . and $\alpha_{3n}=\alpha'_n \times F_n/(\alpha'_1 \times F_1+\alpha'_2 \times F_2+ \ldots +\alpha'_n \times F_n)$ when compositions of U'c are represented by $\alpha_{31}:\alpha_{32}: \ldots :\alpha_{3n}$ and the factors obtained in above (vii) are represented by $F_1, F_2 \ldots F_n$, and wherein a smallest factor among $F_1$ to $F_n$ is substituted by 0.

4. A polymer for lithography, wherein the polymer is obtained by the method according to claim 1.

5. A resist composition, comprising:

the polymer obtained according to claim 1; and a compound, wherein the compound generates an acid when the compound is irradiated with an active ray or a radial ray.

6. A method for producing a substrate having a pattern formed thereon, the method comprising:

applying the resist composition according to claim 5 to a working surface of the substrate, thereby forming a resist film;

exposing the resist film to light, thereby forming an exposed resist film; and developing the exposed resist film with a developing solution.

* * * * *